US009550979B2

(12) United States Patent
Koepke et al.

(10) Patent No.: US 9,550,979 B2
(45) Date of Patent: Jan. 24, 2017

(54) ENZYME-ALTERED METABOLITE ACTIVITY

(71) Applicant: LANZATECH NEW ZEALAND LIMITED, Auckland (NZ)

(72) Inventors: Michael Koepke, Auckland (NZ); Wayne Michael Patrick, Auckland (NZ); Danielle Joan Maddock, Auckland (NZ); Monica Gerth, Roselle, IL (US)

(73) Assignee: Lanza Tech New Zealand Limited, Auckland (NZ)

( * ) Notice: Subject to any disclaimer, the term of this patent is extended or adjusted under 35 U.S.C. 154(b) by 61 days.

(21) Appl. No.: 13/857,375

(22) Filed: Apr. 5, 2013

(65) Prior Publication Data

US 2013/0267006 A1    Oct. 10, 2013

Related U.S. Application Data

(60) Provisional application No. 61/620,538, filed on Apr. 5, 2012.

(51) Int. Cl.
*C12N 9/04* (2006.01)

(52) U.S. Cl.
CPC ..... *C12N 9/0006* (2013.01); *C12Y 101/01001* (2013.01); *C12Y 101/01002* (2013.01); *Y02E 50/17* (2013.01)

(58) Field of Classification Search
CPC ............. C12N 9/0006; C12Y 101/01001; C12Y 101/01002
See application file for complete search history.

(56) References Cited

U.S. PATENT DOCUMENTS

| | | | |
|---|---|---|---|
| 8,455,239 B2 | 6/2013 | Feldman et al. | |
| 2002/0064847 A1 | 5/2002 | Yamamoto et al. | |
| 2005/0084921 A1* | 4/2005 | Cranley et al. | 435/25 |
| 2011/0177579 A1 | 7/2011 | Ma et al. | |
| 2011/0236941 A1 | 9/2011 | Koepke et al. | |
| 2011/0250629 A1* | 10/2011 | Heijstra | 435/29 |
| 2012/0252083 A1 | 10/2012 | Koepke et al. | |
| 2013/0102044 A1* | 4/2013 | Reeves | C12N 15/52 435/161 |

FOREIGN PATENT DOCUMENTS

WO    2004013332    2/2004
WO    2008035187    3/2008

OTHER PUBLICATIONS

Burdette et al., Biochem J. 326, 717-724 (1997).*
Hassler et al., Appl. Biochem. Biotechnol. 143, 1-15 (2007).*
Lee YK et al. International Journal of Systematic Bacteriology. 1993. vol. 43, No. 1. p. 41-51.*
Abrini, J., Naveau, H., & Nyns, E. J. Clostridium autoethanogenum, sp. nov., an anaerobic bacterium that produces ethanol from carbon monoxide. Archives of microbiology, 161(4), 345-351(1994).
Bennett, G. N., & San, K. Systems Biology and Biotechnology of Escherichia coli. In S. Y. Lee (Ed.), Systems Biology and Biotechnology of Escherichia coli; pp. 351-376(2009). Dordrecht: Springer Netherlands. doi:10.1007/978-1-4020-9394-4.
Berzin, V., Kiriukhin, M., & Tyurin, M. Selective production of acetone during continuous synthesis gas fermentation by engineered biocatalyst Clostridium sp. MAceT113. Letters in applied microbiology; vol. 55(2), pp. 149-152 (2012). doi:10.1111/j.1472-765X.2012.03272.x.
Collins, M. D., Lawson, P. A., Willems, A., Cordoba, J. J., Fernandez-Garayzabal, J., Garcia, R, Cai, J., et al. The phylogeny of the genus Clostridium: proposal of five new genera and eleven new species combinations. International Journal of Systematic Bacteriology, 44(4), 812-26 (1994). Retrieved from http://www.ncbi.nlm.nih.gov/pubmed/7981107.
Drake, H. L., Küsel, K., Matthies, C., Wood, H. G., & Ljungdahl, L. G. Acetogenic Prokaryotes. In M. Dworkin, S. Falkow, E. Rosenberg, K.-H. Schleifer, & E. Stackebrandt (Eds.), The Prokaryotes (3rd Edition, pp. 354-420(2006)). New York, NY: Springer. doi:10.1007/0-387-30742-7.
Heap, J. T., Pennington, O. J., Cadman, S. T., & Minton, N. P. A modular system for Clostridium shuttle plasmids. Journal of Microbiological Methods, 78(1), 79-85(2009). doi:10.1016/j.mimet.2009.05.004.
Ismaiel, a a, Zhu, C. X., Colby, G. D., & Chen, J. S. Purification and characterization of a primary-secondary alcohol dehydrogenase from two strains of Clostridium beijerinckii. Journal of bacteriology, 175(16), 5097-105(1993).
Keis, S., Shaheen, R., & Jones, D. T. Emended descriptions of Clostridium acetobutylicum and Clostridium beijerinckii , and descriptions of Clostridium saccharoperbutylacetonicum sp . nov . and. International Journal of Systematic and Evolutionary Microbiology, 2095-2103 (2001).
Kita, A., Iwasaki, Y., Sakai, S., Okuto, S., Takaoka, K., Suzuki, T., Yano, S., et al. Development of genetic transformation and heterologous expression system in carboxydotrophic thermophilic acetogen Moorella thermoacetica. Journal of Bioscience and Bioengineering, vol. 115(4), pp. 347-352 (2013). doi:10.1016/j.jbiosc.2012.10.013.
Köpke, M., & Dürre, P. . Biochemical production of biobutanol. In R. Luque, J. Campelo, & J. H. Clark (Eds.), Handbook of Biofuels Production: Processes and Technologies pp. 221-257 (2011). Woodhead Publishing Ltd. Camebridge, UK.
Köpke, M., Held, C., Hujer, S., Liesegang, H., Wiezer, A., Wollherr, A., Ehrenreich, A., et al. Clostridium ljungdahlii represents a microbial production platform based on syngas. Proceedings of the National Academy of Sciences of the United States of America, 107(29), 13087-92(2010). doi:10.1073/pnas.1004716107.
Köpke, M., Mihalcea, C., Liew, F., Tizard, J. H., Ali, M. S., Conolly, J. J., Al-Sinawi, B., et al. 2,3-Butanediol Production by Acetogenic Bacteria, an Alternative Route to Chemical Synthesis, Using Industrial Waste Gas. Applied and Environmental Microbiology, 77(15), 5467-75 (2011). doi:10.1128/AEM.00355-11.

(Continued)

*Primary Examiner* — Paul Holland
(74) *Attorney, Agent, or Firm* — Andrea E. Schoen

(57) ABSTRACT

The present invention relates to mutant alcohol dehydrogenase enzymes, microorganisms comprising the mutant alcohol dehydrogenase enzymes, and methods for the production of products by microbial fermentation using the microorganisms.

21 Claims, 8 Drawing Sheets

(56) References Cited

OTHER PUBLICATIONS

Leang, C., Ueki, T., & Lovley, D. R. Development of Genetic Systems for Clostridium ljungdahlii. Poster presented at the American Society for Microbiology meeting May 21-24, 2011.

Mermelstein, L. D., & Papoutsakis, E. T. In vivo methylation in *Escherichia coli* by the Bacillus subtilis phage phi 3T I methyltransferase to protect plasmids from restriction upon transformation of Clostridium acetobutylicum ATCC 824. Applied and Environmental Microbiology, 59(4), 1077-81(1993).

Perez, J. M., Richter, H., Loftus, S. E., & Angenent, L. T. Biocatalytic reduction of short-chain carboxylic acids into their corresponding alcohols with syngas fermentation. Biotechnology and Bioengineering, 1-30(2012). doi:10.1002/bit.24786.

Tanner, R. S., Miller, L. M., & Yang, D. *Clostridium ljungdahlii* sp. nov., an acetogenic species in clostridial rRNA homology group I. International Journal of Systematic Bacteriology, 43(2), 232(1993).

Tyurin, M., & Kiriukhin, M. Electrofusion of cells of Acetogen *Clostridium* sp. MT 351 with erm (B) or cat in the chromosome. Journal of Biotech, 1-12 (2012).

Pace, C. N., F. Vajdos, et al. How to measure and predict the molar absorption coefficient of a protein. Protein Sci. 4 (11): 2411-2423(1995).

Bachovchin, W. W., Eagar, R. G., Moore, K. W., & Richards, J. H. Mechanism of action of adenosylcobalamin: glycerol and other substrate analogues as substrates and inactivators for propanediol dehydratase—kinetics, stereospecificity, and mechanism. Biochemistry, 16(6), 1082-92(1977).

Toraya T, Shirakashi T, Kosuga T, F. S. Substrate Specificity of Coenzyme B12-Dependent Diol Dehydratase. Biochemical and biophysical research communications, 69(2), 475-480(1976).

Steen, E. J., Chan, R., Prasad, N., Myers, S., Petzold, C. J., Redding, A., Ouellet, M., et al. ( Metabolic engineering of *Saccharomyces cerevisiae* for the production of n-butanol. Microbial cell factories, 7, 362008). doi:10.1186/1475-2859-7-36.

Romano, P., Suzzi, G., Mortimer, R., & Polsinelli, M. Production of high levels of acetoin in *Saccharomyces cerevisiae* wine yeasts is a recessive trait. The Journal of Applied Bacteriology, 78(2), 169-74(1995).

Abrini, *Clostridium autoethanogenum*, sp. nov., an anaerobic bacterium that produces ethanol from carbon monoxide, Arch Microbiol, 161: 345-351, 1994.

Bennett, Engineering *E. coli* central metabolism for enhanced primary metabolite production, Systems Biology and Biotechnology of *Escherichia coli*, 351-376, 2009.

Berzin, Selective production of acetone during continuous synthesis gas fermentation by engineered biocatalyst *Clostridium* sp. MAceT113, Lett Appl Microbiol, 55: 149-154, 2012.

Collins, The phylogeny of the genus *Clostridium*: proposal of five new genera and eleven new species combinations, Int J Systemic Evolutionary Microbiol, 44: 812-826, 1994.

Drake, Acetogenic prokaryotes, The Prokaryotes, 354-420, 2006.

Heap, A modular system for Clostridium shuttle plasmids, J Microbiol Meth, 78: 79-85, 2009.

Ismaiel, Purification and characterization of a primary-secondary alcohol dehydrogenase from two strains of Clostridium beijerinckii, J Bacteriol, 175: 5097-5105, 1993.

Keis, Emended descriptions of Clostridium acetobutylicum and Clostridium beijerinckii , and descriptions of *Clostridium saccharoperbutylacetonicum* sp. nov., Int J Systemic Evolutionary Microbiol, 51: 2095-2103, 2001.

Kita, Development of genetic transformation and heterologous expression system in carboxydotrophic thermophilic acetogen Moorella thermoacetica, J Biosci Bioeng, 115: 347-352, 2013.

Kopke, Biochemical production of biobutanol, Handbook of Biofuels Production: Processes and Technologies, 221-257, 2011.

Kopke, Clostridium ljungdahlii represents a microbial production platform based on syngas, PNAS, 107: 13087-13092, 2010.

Kopke, 2,3-Butanediol production by acetogenic bacteria, an alternative route to chemical synthesis, using industrial waste gas, Appl Environ Microbiol, 77: 5467-5475, 2011.

Leang, Development of genetic systems for Clostridium ljungdahlii, poster presented at the American Society for Microbiology Meeting, May 21-24, 2011.

Mermelstein, In vivo methylation in *Escherichia coli* by the Bacillus subtilis phage phi 3T I methyltransferase to protect plasmids from restriction upon transformation of Clostridium acetobutylicum ATCC 824, Appl Environ Microbiol, 59: 1077-1081, 1993.

Perez, Biocatalytic reduction of short-chain carboxylic acids into their corresponding alcohols with syngas fermentation, Biotechnol Bioeng, 110: 1066-1077, 2013.

Tanner, *Clostridium ljungdahlii* sp. nov., an acetogenic species in clostridial rRNA homology group I, Int J Systematic Bacteriol, 43: 232-236, 1993.

Tyurin, Electrofusion of cells of Acetogen *Clostridium* sp. MT 351 with erm (B) or cat in the chromosome, J Biotech Res, 4: 1-12, 2012.

Pace, How to measure and predict the molar absorption coefficient of a protein, Protein Sci, 4: 2411-2423, 1995.

Bachovchin, Mechanism of action of adenosylcobalamin: glycerol and other substrate analogues as substrates and inactivators for propanediol dehydratase—kinetics, stereospecificity, and mechanism, Biochem, 16:1082-1092, 1977.

Toraya, Substrate specificity of coenzyme B12-dependent diol dehydratase, Biochem Biophys Res Comm, 69: 475-480, 1976.

Steen, Metabolic engineering of *Saccharomyces cerevisiae* for the production of n-butanol, Microbial Cell Factories, 7: 36, 2008.

Romano, Production of high levels of acetoin in *Saccharomyces cerevisiae* wine yeasts is a recessive trait, J Appl Bacteriol, 78: 169-174, 1995.

GenBank AGY74782.1, Alcohol dehydrogenase zinc-binding protein [Clostridium autoethanogenum DSM 10061], 351 aa, Jun. 11, 2014.

European Search Report for Patent Application 13772074.4, European Patent Office, Aug. 26, 2015.

Korkhin Y et al., NADP-dependent bacterial alcohol dehydrogenases: crystal structure, cofactor-binding and cofactor specificity of the ADHs of Clostridium beijerinckii and Thermoanaerobacter brockii, Journal of Molecular Biology, May 22, 1998, pp. 967-981, vol. 278, No. 5.

Maddock, Danielle J., et al., Substitutions at the cofactor phosphate-binding site of a clostridial alcholo dehydrogenase lead to unexpected changes in substrate specificity, Protein Engineering Design and Selection, Aug. 10, 2015, pp. 251-258, vol. 28, No. 8.

Koepke, M.. et al., Reconstruction of an Acetongenic 2,3-Butanediol Pathway Involving a Novel NADPH-Dependent Primary-Secondary Alcohol Dehydrogenase, Applied and Environmental Microbiology, Jun. 1, 2014, vol. 80, No. 11.

Database Geneseq, C. autoethanogenum.C.Ljungdahlii/C. ragsdalei ADS protein, SEQ ID 1.

New Zealand Intellectual Property Office, First Examination Report NZ 700609, Jul. 23, 2015.

\* cited by examiner

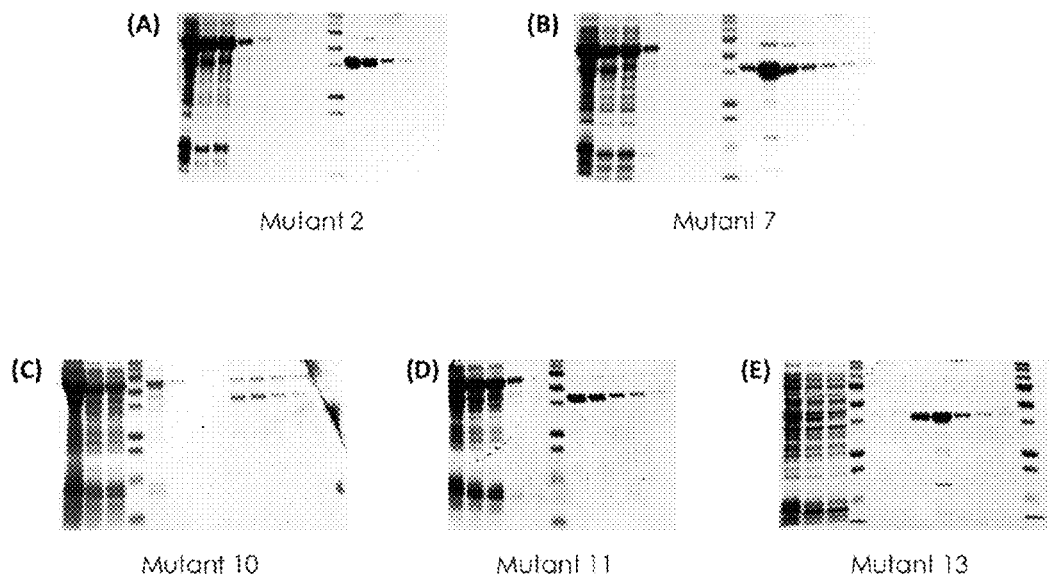
FIG 5
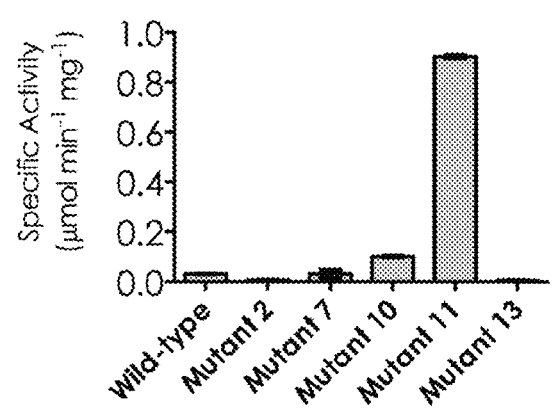
FIG 6    note: 5 mM acetone was the substrate in all assays.

| | $K_{cat}$ [sec$^{-1}$] | $K_M$ [mM] | $K_{cat}/K_M$ [sec$^{-1}$ mM$^{-1}$] |
|---|---|---|---|
| Primary Adh | | | |
| Acetaldehyde to Ethanol | 93 ± 6 | 5.5 ± 1.4 | 1.7 x 10$^4$ |
| Secondary Adh | | | |
| Acetone to Isopropanol | 51.4 ± 0.8 | 0.60 ± 0.02 | 8.6 x 10$^4$ |
| Acetoin to 2,3-Butanediol | 41.8 ± 0.7 | 5.7 ± 1.4 | 7.4 x 10$^3$ |
| MEK (2-Butanone) to 2-Butanol | 44 ± 2 | 1.2 ± 0.1 | 3.8 x 10$^4$ |

SEQUENCE LISTING

```
<160> NUMBER OF SEQ ID NOS: 70

<210> SEQ ID NO 1
<211> LENGTH: 37
<212> TYPE: DNA
<213> ORGANISM: Artificial sequence
<220> FEATURE:
<223> OTHER INFORMATION: synthetic primer

<400> SEQUENCE: 1
ggtaatcatg aaaggttttg caatgttagg tattaac                          37

<210> SEQ ID NO 2
<211> LENGTH: 45
<212> TYPE: DNA
<213> ORGANISM: Artificial sequence
<220> FEATURE:
<223> OTHER INFORMATION: synthetic primer

<400> SEQUENCE: 2
tctagaagct tagaatgtaa ctactgattt aattaaatct tttgg                 45

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
atgccatagc atttttatcc                                             20

<210> SEQ ID NO 4
<211> LENGTH: 56
<212> TYPE: DNA
<213> ORGANISM: Artificial sequence
<220> FEATURE:
<223> OTHER INFORMATION: Synthetic primer

<400> SEQUENCE: 4
caggtaccga gaacctgtat ttccaaggaa aaggttttgc aatgttaggt attaac     56

<210> SEQ ID NO 5
<211> LENGTH: 26
<212> TYPE: DNA
<213> ORGANISM: Artificial sequence
<220> FEATURE:
<223> OTHER INFORMATION: synthetic primer
```

```
<400> SEQUENCE: 5
cacaaacagg ttcgcttcca acaccg                                          26

<210> SEQ ID NO 6
<211> LENGTH: 26
<212> TYPE: DNA
<213> ORGANISM: Artificial sequence
<220> FEATURE:
<223> OTHER INFORMATION: Synthetic primer

<400> SEQUENCE: 6
cggtgttgga agcgaacctg tttgtg                                          26

<210> SEQ ID NO 7
<211> LENGTH: 24
<212> TYPE: DNA
<213> ORGANISM: Artificial sequence
<220> FEATURE:
<223> OTHER INFORMATION: synthetic primer

<400> SEQUENCE: 7
caaacaggtc tttctccaac accg                                            24

<210> SEQ ID NO 8
<211> LENGTH: 24
<212> TYPE: DNA
<213> ORGANISM: Artificial sequence
<220> FEATURE:
<223> OTHER INFORMATION: synthetic primer

<400> SEQUENCE: 8
cggtgttgga gaaagacctg tttg                                            24

<210> SEQ ID NO 9
<211> LENGTH: 26
<212> TYPE: DNA
<213> ORGANISM: Artificial sequence
<220> FEATURE:
<223> OTHER INFORMATION: synthetic primer

<400> SEQUENCE: 9
cacaaacagg ctgttctcca acaccg                                          26

<210> SEQ ID NO 10
<211> LENGTH: 26
<212> TYPE: DNA
<213> ORGANISM: Artificial sequence
<220> FEATURE:
<223> OTHER INFORMATION: synthetic primer

<400> SEQUENCE: 10
cggtgttgga gaacagcctg tttgtg                                          26

<210> SEQ ID NO 11
<211> LENGTH: 24
<212> TYPE: DNA
<213> ORGANISM: Artificial sequence
<220> FEATURE:
<223> OTHER INFORMATION: synthetic primer

<400> SEQUENCE: 11
caaacaggtc tgtctccaac accg                                            24

<210> SEQ ID NO 12
<211> LENGTH: 24
```

```
<212> TYPE: DNA
<213> ORGANISM: Artificial sequence
<220> FEATURE:
<223> OTHER INFORMATION: synthetic primer

<400> SEQUENCE: 12
cggtgttgga gacagacctg tttg                                    24

<210> SEQ ID NO 13
<211> LENGTH: 26
<212> TYPE: DNA
<213> ORGANISM: Artificial sequence
<220> FEATURE:
<223> OTHER INFORMATION: synthetic primer

<400> SEQUENCE: 13
cggtgttgga agccagcctg tttgtg                                  26

<210> SEQ ID NO 14
<211> LENGTH: 26
<212> TYPE: DNA
<213> ORGANISM: Artificial sequence
<220> FEATURE:
<223> OTHER INFORMATION: synthetic primer

<400> SEQUENCE: 14
cacaaacagg ctggcttcca acaccg                                  26

<210> SEQ ID NO 15
<211> LENGTH: 26
<212> TYPE: DNA
<213> ORGANISM: Artificial sequence
<220> FEATURE:
<223> OTHER INFORMATION: synthetic primer

<400> SEQUENCE: 15
gttcatatga aagaagttgt aatagc                                  26

<210> SEQ ID NO 16
<211> LENGTH: 25
<212> TYPE: DNA
<213> ORGANISM: Artificial sequence
<220> FEATURE:
<223> OTHER INFORMATION: synthetic primer

<400> SEQUENCE: 16
caagaattcc tagcactttt ctagc                                   25

<210> SEQ ID NO 17
<211> LENGTH: 26
<212> TYPE: DNA
<213> ORGANISM: Artificial sequence
<220> FEATURE:
<223> OTHER INFORMATION: synthetic primer

<400> SEQUENCE: 17
ctaggtacca gggagatatt aaaatg                                  26

<210> SEQ ID NO 18
<211> LENGTH: 26
<212> TYPE: DNA
<213> ORGANISM: Artificial sequence
<220> FEATURE:
<223> OTHER INFORMATION: synthetic primer

<400> SEQUENCE: 18
```
cgtggatcct ctatattgct tttatt                                    26

<210> SEQ ID NO 19
<211> LENGTH: 29
<212> TYPE: DNA
<213> ORGANISM: Artificial sequence
<220> FEATURE:
<223> OTHER INFORMATION: synthetic primer

<400> SEQUENCE: 19
aagcggccgc agatagtcat aatagttcc                                 29

<210> SEQ ID NO 20
<211> LENGTH: 29
<212> TYPE: DNA
<213> ORGANISM: Artificial sequence
<220> FEATURE:
<223> OTHER INFORMATION: synthetic primer

<400> SEQUENCE: 20
ttccatatga ataattccct ccttaaagc                                 29

<210> SEQ ID NO 21
<211> LENGTH: 34
<212> TYPE: DNA
<213> ORGANISM: Artificial sequence
<220> FEATURE:
<223> OTHER INFORMATION: synthetic primer

<400> SEQUENCE: 21
tatttgtcga cttaggaggt tctattatga aagg                           34

<210> SEQ ID NO 22
<211> LENGTH: 30
<212> TYPE: DNA
<213> ORGANISM: Artificial sequence
<220> FEATURE:
<223> OTHER INFORMATION: synthetic primer

<400> SEQUENCE: 22
aaaactcgag acattttttt aatgcgacag                                30

<210> SEQ ID NO 23
<211> LENGTH: 33
<212> TYPE: DNA
<213> ORGANISM: Artificial sequence
<220> FEATURE:
<223> OTHER INFORMATION: synthetic primer

<400> SEQUENCE: 23
gcattattgg cgttgaggtt cgtgaggtct gcg                            33

<210> SEQ ID NO 24
<211> LENGTH: 33
<212> TYPE: DNA
<213> ORGANISM: Artificial sequence
<220> FEATURE:
<223> OTHER INFORMATION: synthetic primer

<400> SEQUENCE: 24
cgcagacctc acgaacctca acgccaataa tgc                            33

<210> SEQ ID NO 25
<211> LENGTH: 35
<212> TYPE: DNA
<213> ORGANISM: Artificial sequence

```
<220> FEATURE:
<223> OTHER INFORMATION: synthetic primer

<400> SEQUENCE: 25
gggtcgcatt attggcgttg atcttcgtga ggtct                                 35

<210> SEQ ID NO 26
<211> LENGTH: 35
<212> TYPE: DNA
<213> ORGANISM: Artificial sequence
<220> FEATURE:
<223> OTHER INFORMATION: synthetic primer

<400> SEQUENCE: 26
agacctcacg aagatcaacg ccaataatgc gaccc                                 35

<210> SEQ ID NO 27
<211> LENGTH: 37
<212> TYPE: DNA
<213> ORGANISM: Artificial sequence
<220> FEATURE:
<223> OTHER INFORMATION: synthetic primer

<400> SEQUENCE: 27
ccacggacat cgtcaatttc aaaaatggcg acattgt                               37

<210> SEQ ID NO 28
<211> LENGTH: 37
<212> TYPE: DNA
<213> ORGANISM: Artificial sequence
<220> FEATURE:
<223> OTHER INFORMATION: synthetic primer

<400> SEQUENCE: 28
acaatgtcgc cattttgaa attgacgatg tccgtgg                                37

<210> SEQ ID NO 29
<211> LENGTH: 42
<212> TYPE: DNA
<213> ORGANISM: Artificial sequence
<220> FEATURE:
<223> OTHER INFORMATION: synthetic primer

<400> SEQUENCE: 29
gtgccacgga catcgtcaat gccaaaaatg gcgacattgt tg                         42

<210> SEQ ID NO 30
<211> LENGTH: 42
<212> TYPE: DNA
<213> ORGANISM: Artificial sequence
<220> FEATURE:
<223> OTHER INFORMATION: synthetic primer

<400> SEQUENCE: 30
caacaatgtc gccatttttg gcattgacga tgtccgtggc ac                         42

<210> SEQ ID NO 31
<211> LENGTH: 35
<212> TYPE: DNA
<213> ORGANISM: Artificial sequence
<220> FEATURE:
<223> OTHER INFORMATION: synthetic primer

<400> SEQUENCE: 31
cattattggc gttgatgatc gtgaggtctg cgtcg                                 35
```

<210> SEQ ID NO 32
<211> LENGTH: 35
<212> TYPE: DNA
<213> ORGANISM: Artificial sequence
<220> FEATURE:
<223> OTHER INFORMATION: synthetic primer

<400> SEQUENCE: 32
cgacgcagac ctcacgatca tcaacgccaa taatg					35

<210> SEQ ID NO 33
<211> LENGTH: 48
<212> TYPE: DNA
<213> ORGANISM: Artificial sequence
<220> FEATURE:
<223> OTHER INFORMATION: synthetic primer

<400> SEQUENCE: 33
atggagcaac tgatattgta aatgctaaaa atggtgatat agttgaac					48

<210> SEQ ID NO 34
<211> LENGTH: 48
<212> TYPE: DNA
<213> ORGANISM: Artificial sequence
<220> FEATURE:
<223> OTHER INFORMATION: synthetic primer

<400> SEQUENCE: 34
gttcaactat atcaccattt ttagcattta caatatcagt tgctccat					48

<210> SEQ ID NO 35
<211> LENGTH: 1056
<212> TYPE: DNA
<213> ORGANISM: Clostridium autoethanogenum

<400> SEQUENCE: 35
atgaaaggtt ttgcaatgtt aggtattaac aaattaggat ggattgaaaa gaaaaaccca					60 gtgccaggtc cttatgatgc gattgtacat cctctagctg tatccccatg tacatcagat					120 atacatacgg tttttgaagg agcacttggt aatagggaaa atatgatttt aggccatgaa					180 gctgtaggtg aaatagccga agttggcagc gaagttaaag attttaaagt tggcgataga					240 gttatcgtac catgcacaac acctgactgg agatctttag aagtccaagc tggttttcag					300 cagcattcaa acggtatgct tgcaggatgg aagttttcca attttaaaga tggtgtattt					360 gcagattact tcatgtaaa cgatgcagat atgaatcttg ccatactccc agatgaaata					420 cctttagaaa gtgcagttat gatgacagac atgatgacta ctggttttca tggagcagaa					480 cttgcagaca taaaaatggg ctccagcgtt gtagtaattg gtataggagc tgttggatta					540 atgggaatag ccggttccaa acttcgagga gcaggcagaa ttatcggtgt tggaagcaga					600 cctgtttgtg ttgaaacagc taaatttat ggagcaactg atattgtaaa ttataaaaat					660 ggtgatatag ttgaacaaat catggactta actcatggta aaggtgtaga ccgtgtaatc					720 atggcaggcg gtggtgctga aacactagca caagcagtaa ctatggttaa acctggcggc					780 gtaatttcta acatcaacta ccatggaagc ggtgatactt taccaatacc tcgtgttcaa					840 tggggctgcg gcatggctca caaaactata agaggaggat tatgccccgg cggacgtctt					900 agaatggaaa tgctaagaga tcttgttcta tataaacgtg ttgatttgag taaacttgtt					960 actcatgtat ttgatggtgc agaaaatatt gaaaaggccc ttttgcttat gaaaaataag					1020 ccaaaagatt taattaaatc agtagttaca ttctaa					1056

<210> SEQ ID NO 36
<211> LENGTH: 351
<212> TYPE: PRT
<213> ORGANISM: Clostridium autoethanogenum

<400> SEQUENCE: 36

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
    195                 200                 205

Phe Tyr Gly Ala Thr Asp Ile Val Asn Tyr Lys Asn Gly Asp Ile Val
210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
    275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 37
<211> LENGTH: 1056
<212> TYPE: DNA

<213> ORGANISM: Clostridium autoethanogenum

<400> SEQUENCE: 37

```
atgaaaggtt ttgcaatgtt aggtattaac aaattaggat ggattgaaaa gaaaaaccca      60
gtgccaggtc cttatgatgc gattgtacat cctctagctg tatccccatg tacatcagat     120
atacatacgg tttttgaagg agcacttggt aatagggaaa atatgatttt aggccatgaa     180
gctgtaggtg aaatagccga agttggcagc gaagttaaag attttaaagt tggcgataga     240
gttatcgtac catgcacaac acctgactgg agatctttag aagtccaagc tggttttcag     300
cagcattcaa acggtatgct tgcaggatgg aagttttcca attttaaaga tggtgtattt     360
gcagattact ttcatgtaaa cgatgcagat atgaatcttg ccatactccc agatgaaata     420
cctttagaaa gtgcagttat gatgacagac atgatgacta ctggttttca tggagcagaa     480
cttgcagaca taaaaatggg ctccagcgtt gtagtaattg gtataggagc tgttggatta     540
atgggaatag ccggttccaa acttcgagga gcaggcagaa ttatcggtgt tggagacaga     600
cctgtttgtg ttgaaacagc taaattttat ggagcaacta tattgtaaa ttataaaaat      660
ggtgatatag ttgaacaaat catggactta actcatggta aggtgtaga ccgtgtaatc      720
atggcaggcg gtggtgctga acactagca caagcagtaa ctatggttaa acctggcggc     780
gtaatttcta acatcaacta ccatggaagc ggtgatactt taccaatacc tcgtgttcaa     840
tggggctgcg gcatggctca aaaactata agaggaggat tatgccccgg cggacgtctt     900
agaatggaaa tgctaagaga tcttgttcta tataaacgtg ttgatttgag taaacttgtt     960
actcatgtat ttgatggtgc agaaaatatt gaaaaggccc ttttgcttat gaaaaataag   1020
ccaaaagatt taattaaatc agtagttaca ttctaa                              1056
```

<210> SEQ ID NO 38
<211> LENGTH: 351
<212> TYPE: PRT
<213> ORGANISM: Clostridium autoethanogenum

<400> SEQUENCE: 38

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
```

```
                   165                 170                 175
Ala Val Gly Leu Met Gly Ile Ala Gly Ser Lys Leu Arg Gly Ala Gly
                180                 185                 190

Arg Ile Ile Gly Val Gly Asp Arg Pro Val Cys Val Glu Thr Ala Lys
            195                 200                 205

Phe Tyr Gly Ala Thr Asp Ile Val Asn Tyr Lys Asn Gly Asp Ile Val
        210                 215                 220

Glu Gln Ile Met Asp Leu Thr His Gly Lys Gly Val Asp Arg Val Ile
225                 230                 235                 240

Met Ala Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
                260                 265                 270

Thr Leu Pro Ile Pro Arg Val Gln Trp Gly Cys Gly Met Ala His Lys
            275                 280                 285

Thr Ile Arg Gly Gly Leu Cys Pro Gly Gly Arg Leu Arg Met Glu Met
        290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
                340                 345                 350

<210> SEQ ID NO 39
<211> LENGTH: 560
<212> TYPE: DNA
<213> ORGANISM: Clostridium autoethanogenum

<400> SEQUENCE: 39
agatagtcat aatagttcca gaatagttta atttagcatt tggattaaat tcccatatgt    60
ttgttaaata tataccaaac tagtatagat atttttaaaa tactgtactt aaacagtagt   120
aatttacgta aaaaaatttt ttgatttttt taaaaaagtc cttttcaagt tgtacattat   180
tatggtaata tgtaattgaa gaagttgtgt agtaatattg taaacgtttc ttaatttatt   240
ttcatccatg tagtgcttaa aaaaccaaaa tatgtcacac gcaattgcat atttcaaaca   300
ataatattta ttttctcgtt aaattcacaa ataatttatt aataatatca ataaccaaga   360
ttatacttaa atggatgttt atttttttaac atttttttata gtaaatatat ttattttatg   420
tagtaaaaag gttataatta taattgtatt tattacaatt aattaaaata aaaaaatagg   480
gttttaggta aaattaagtt attttaagaa gtaattacaa caaaaattga agttatttct   540
ttaaggaggg aattattaaa                                               560

<210> SEQ ID NO 40
<211> LENGTH: 7922
<212> TYPE: DNA
<213> ORGANISM: Artificial sequence
<220> FEATURE:
<223> OTHER INFORMATION: synthetic plasmid

<400> SEQUENCE: 40
tcgaggcctg cagacatgca agcttggcac tggccgtcgt tttacaacgt cgtgactggg    60
aaaaccctgg cgttacccaa cttaatcgcc ttgcagcaca tccccctttc gccagctggc   120
gtaatagcga agaggcccgc accgatcgcc cttcccaaca gttgcgcagc ctgaatggcg   180
```

```
aatggcgcta gcataaaaat aagaagcctg catttgcagg cttcttattt ttatggcgcg      240
ccgcattcac ttcttttcta tataaatatg agcgaagcga ataagcgtcg gaaaagcagc      300
aaaaagtttc cttttgctg ttggagcatg ggggttcagg gggtgcagta tctgacgtca       360
atgccgagcg aaagcgagcc gaagggtagc atttacgtta gataaccccc tgatatgctc      420
cgacgcttta tatagaaaag aagattcaac taggtaaaat cttaatatag gttgagatga      480
taaggtttat aaggaatttg tttgttctaa ttttcactc atttgttct aatttctttt        540 aacaaatgtt cttttttttt tagaacagtt atgatatagt tagaatagtt taaaataagg      600
agtgagaaaa agatgaaaga aagatatgga acagtctata aaggctctca gaggctcata      660
gacgaagaaa gtggagaagt catagaggta gacaagttat accgtaaaca aacgtctggt      720
aacttcgtaa aggcatatat agtgcaatta ataagtatgt tagatatgat tggcggaaaa      780
aaacttaaaa tcgttaacta tatcctagat aatgtccact taagtaacaa tacaatgata      840
gctacaacaa gagaaatagc aaaagctaca ggaacaagtc tacaaacagt aataacaaca      900
cttaaaatct tagaagaagg aaatattata aaaagaaaaa ctggagtatt aatgttaaac      960
cctgaactac taatgagagg cgacgaccaa aaacaaaaat acctcttact cgaatttggg     1020
aactttgagc aagaggcaaa tgaaatagat tgacctccca ataacaccac gtagttattg     1080
ggaggtcaat ctatgaaatg cgattaaggg ccggccagtg ggcaagttga aaaattcaca     1140
aaaatgtggt ataatatctt tgttcattag agcgataaac ttgaatttga gagggaactt     1200
agatggtatt tgaaaaaatt gataaaaata gttggaacag aaaagagtat tttgaccact     1260
actttgcaag tgtaccttgt acctacagca tgaccgttaa agtggatatc acacaaataa     1320
aggaaaaggg aatgaaacta tatcctgcaa tgctttatta tattgcaatg attgtaaacc     1380
gccattcaga gtttaggacg gcaatcaatc aagatggtga attggggata tatgatgaga     1440
tgataccaag ctatacaata tttcacaatg atactgaaac attttccagc ctttggactg     1500
agtgtaagtc tgactttaaa tcatttttag cagattatga aagtgatacg caacggtatg     1560
gaaacaatca tagaatggaa ggaaagccaa atgctccgga aaacatttt aatgtatcta      1620 tgataccgtg tcaaccttc gatggcttta atctgaattt gcagaaagga tatgattatt     1680
tgattcctat ttttactatg gggaaatatt ataaagaaga taacaaaatt atacttcctt    1740
tggcaattca agttcatcac gcagtatgtg acggatttca catttgccgt tttgtaaacg     1800
aattgcagga attgataaat agttaacttc aggtttgtct gtaactaaaa acaagtattt     1860
aagcaaaaac atcgtagaaa tacggtgttt tttgttaccc taagtttaaa ctcctttttg    1920
ataatctcat gaccaaaatc ccttaacgtg agttttcgtt ccactgagcg tcagaccccg     1980
tagaaaagat caaaggatct tcttgagatc cttttttct gcgcgtaatc tgctgcttgc      2040
aaacaaaaaa accaccgcta ccagcggtgg tttgtttgcc ggatcaagag ctaccaactc     2100 ttttccgaa ggtaactggc ttcagcagag cgcagatacc aaatactgtt cttctagtgt      2160
agccgtagtt aggccaccac ttcaagaact ctgtagcacc gcctacatac ctcgctctgc     2220
taatcctgtt accagtggct gctgccagtg gcgataagtc gtgtcttacc gggttggact     2280
caagacgata gttaccggat aaggcgcagc ggtcgggctg aacggggggt tcgtgcacac     2340
agcccagctt ggagcgaacg acctacaccg aactgagata cctacagcgt gagctatgag     2400
aaagcgccac gcttcccgaa gggagaaagg cggacaggta tccggtaagc ggcagggtcg     2460
gaacaggaga gcgcacgagg gagcttccag ggggaaacgc ctggtatctt tatagtcctg     2520
tcgggtttcg ccacctctga cttgagcgtc gatttttgtg atgctcgtca gggggggcgga    2580
```

```
gcctatggaa aaacgccagc aacgcggcct ttttacggtt cctggccttt tgctggcctt    2640
ttgctcacat gttctttcct gcgttatccc ctgattctgt ggataaccgt attaccgcct    2700
ttgagtgagc tgataccgct cgccgcagcc gaacgaccga gcgcagcgag tcagtgagcg    2760
aggaagcgga gagcgccca atacgcaggg ccccctgcag gataaaaaaa ttgtagataa    2820 atttttataaa atagttttat ctacaatttt tttatcagga aacagctatg accgcggccg    2880
cagatagtca taatagttcc agaatagttc aatttagaaa ttagactaaa cttcaaaatg    2940
tttgttaaat ataccaaa ctagtataga tattttttaa atactggact taaacagtag    3000
taatttgcct aaaaaatttt ttcaattttt tttaaaaaat cctttcaag ttgtacattg    3060 ttatggtaat atgtaattga agaagttatg tagtaatatt gtaaacgttt cttgattttt    3120
ttacatccat gtagtgctta aaaaaccaaa atatgtcaca tgcaattgta tatttcaaat    3180
aacaatattt attttctcgt taaattcaca ataatttat taataatatc aataaccaag    3240
attatactta aatggatgtt tattttttaa cacttttata gtaaatatat ttattttatg    3300
tagtaaaaag gttataatta taattgtatt tattacaatt aattaaaata aaaaatagggg   3360 ttttaggtaa aattaagtta ttttaagaag taattacaat aaaaattgaa gttatttctt    3420
taaggaggga attattcata tgaaagaagt tgtaatagct agtgcagtaa gaacagcgat    3480
tggatcttat ggaaagtctc ttaaggatgt accagcagta gatttaggag ctacagctat    3540
aaaggaagca gttaaaaaag caggaataaa accagaggat gttaatgaag tcattttagg    3600
aaatgttctt caagcaggtt taggacagaa tccagcaaga caggcatctt ttaaagcagg    3660
attaccagtt gaaattccag ctatgactat taataaggtt tgtggttcag gacttagaac    3720
agttagctta gcagcacaaa ttataaaagc aggagatgct gacgtaataa tagcaggtgg    3780
tatggaaaat atgtctagag ctccttactt agcgaataac gctagatggg gatatagaat    3840
gggaaacgct aaatttgttg atgaaatgat cactgacgga ttgtgggatg catttaatga    3900
ttaccacatg ggaataacag cagaaaacat agctgagaga tggaacattt caagagaaga    3960
acaagatgag tttgctcttg catcacaaaa aaaagctgaa gaagctataa aatcaggtca    4020
atttaaagat gaaatagttc ctgtagtaat taaaggcaga aagggagaaa ctgtagttga    4080
tacagatgag caccctagat ttggatcaac tatagaagga cttgcaaaat taaaacctgc    4140
cttcaaaaaa gatggaacag ttacagctgg taatgcatca ggattaaatg actgtgcagc    4200
agtacttgta atcatgagtg cagaaaaagc taaagagctt ggagtaaaac cacttgctaa    4260
gatagtttct tatggttcag caggagttga cccagcaata atgggatatg gacctttcta    4320
tgcaacaaaa gcagctattg aaaaagcagg ttggacagtt gatgaattag atttaataga    4380
atcaaatgaa gcttttgcag ctcaaagttt agcagtagca aaagatttaa aatttgatat    4440
gaataaagta aatgtaaatg gaggagctat tgcccttggt catccaattg gagcatcagg    4500
tgcaagaata ctcgttactc ttgtacacgc aatgcaaaaa agagatgcaa aaaaaggctt    4560
agcaacttta tgtataggtg gcggacaagg aacagcaata ttgctagaaa agtgctagga    4620
attcgagctc ggtaccaggg agatattaaa atgaataaat tagtaaaatt aacagattta    4680
aagcgcattt tcaaagatgg catgacaatt atggttgggg gttttttaga ttgtggaact    4740
cctgaaaata ttatagatat gctagttgat ttaaatataa aaaatctgac tattataagc    4800
aatgatacag cttttcctaa taaggaata ggaaaactta ttgtaaatgg tcaagtttct    4860
aaagtaattg cttcacatat tggaactaat cctgaaactg gaaaaaaat gagctctgga    4920
```

```
gaacttaaag ttgagctttc cccacaagga acactgattg aaagaattcg tgcagctgga    4980
tctggactcg gaggtgtatt aactccaact ggacttggaa ctatcgttga agaaggtaag    5040
aaaaaagtta ctatcgatgg caaagaatat ctattagaac ttcctttatc tgctgatgtt    5100
tcattaataa aaggtagcat tgtagatgaa tttggaaata ccttctatag ggctgctact    5160
aaaaatttca atccatatat ggcaatggct gcaaaaacag ttatagttga agcagaaaat    5220
ttagttaaat gtgaagattt aaaaagagat gccataatga ctcctggcgt attagtagat    5280
tatatcgtta aggaggcggc ttaattgatt gtagataaag ttttagcaaa agagataatt    5340
gccaaaagag ttgcaaaaga actaaaaaaa gaccaactcg taaaccttgg aataggactt    5400
ccaactttag tagcaaatta tgtaccaaaa gaaatgaaca ttacttttga atcagaaaat    5460
ggcatggttg gtatggcaca aatggcatca tcaggtgaaa atgacccaga tataataaat    5520
gctggcgggg aatatgtaac attattacct caaggttcat tttttgatag ttcaatgtct    5580
ttcgcactaa tacgaggagg acatgttgat gttgctgttc ttggtgctct agaagttgat    5640
gaaaaaggta atttagctaa ctggattgtt ccaataaaaa ttgtcccagg tatgggtggc    5700
gctatggatt tagcaatagg cgcaaaaaaa ataatagtgg caatgcaaca tacaggaaaa    5760
agtaaaccta aaatcgttaa aaaatgtact ctcccactta ctgctaaggc tcaagtggat    5820
ttaattgtca cagaactttg tgtaattgat gtaacaaatg acggcttact tttaaaagaa    5880
attcataaag atacaactat tgatgaaatt aaattttttaa cagatgcaga tttaattatt    5940
ccagataact taaagattat ggatatatga atcattctat tttaaatata taactttaaa    6000
aatcttatgt attaaaaact aagaaaagag gttgattgtt ttatgttaga aagtgaagta    6060
tctaaacaaa ttacaactcc acttgctgct ccagcgtttc ctagaggacc atataggttt    6120
cacaatagag aatatctaaa cattatttat cgaactgatt tagatgctct tcgaaaaata    6180
gtaccagagc cacttgaatt agatagagca tatgttagat ttgaaatgat ggctatgcct    6240
gatacaaccg gactaggctc atatacgaaa tgtggtcaag ctattccagt aaaatatatat    6300 ggtgttaagg gtgactactt gcatatgatg tatctagata tgaacctgc tattgctgtt    6360 ggaagagaaa gtagcgctta tccaaaaaag cttggctatc caaagctatt tgttgattca    6420
gatactttag ttgggacact taaatatggt acattaccag tagctactgc aacaatggga    6480
tataagcacg agcctctaga tcttaaagaa gcctatgctc aaattgcaag acccaattt    6540 atgctaaaaa tcattcaagg ttacgatggt aagccaagaa tttgtgaact aatatgtgca    6600
gaaaatactg atataactat tcacggtgct tggactggaa gtgcacgtct acaattattt    6660
agccatgcac tagctcctct tgctgattta cctgtattag agattgtatc agcatctcat    6720
atcctcacag atttaactct tggaacacct aaggttgtac atgattatct ttcagtaaaa    6780
taaaagcaat atagaggatc ctctagagtc gacttaggag gttctattat gaaaggtttt    6840
gcaatgttag gtattaacaa attaggatgg attgaaaaga aaacccagt gccaggtcct    6900 tatgatgcga ttgtacatcc tctagctgta tcccatgta catcagatat acatacggtt    6960
tttgaaggag cacttggtaa tagggaaaat atgattttag ccatgaagc tgtaggtgaa    7020 atagccgaag ttggcagcga agttaaagat tttaaagttg gcgatagagt tatcgtacca    7080
tgcacaacac ctgactggag atctttagaa gtccaagctg ttttcagca gcattcaaac    7140 ggtatgcttg caggatggaa gttttccaat tttaaagatg gtgtatttgc agattacttt    7200
catgtaaacg atgcagatat gaatcttgcc atactcccag atgaaatacc tttagaaagt    7260
gcagttatga tgacagacat gatgactact ggttttcatg gagcagaact tgcagacata    7320
```

```
aaaatgggct ccagcgttgt agtaattggt ataggagctg ttggattaat gggaatagcc    7380
ggttccaaac ttcgaggagc aggcagaatt atcggtgttg aagcagacc  tgtttgtgtt    7440 gaaacagcta attttatgg  agcaactgat attgtaaatt ataaaaatgg tgatatagtt    7500
gaacaaatca tggacttaac tcatggtaaa ggtgtagacc gtgtaatcat ggcaggcggt    7560
ggtgctgaaa cactagcaca agcagtaact atggttaaac ctggcggcgt aatttctaac    7620
atcaactacc atgaagcgg  tgatacttta ccaatcctc  gtgttcaatg gggctgcggc    7680
atggctcaca aaactataag aggaggatta tgccccggcg gacgtcttag aatggaaatg    7740
ctaagagatc ttgttctata taacgtgtt  gatttgagta acttgttac  tcatgtattt    7800 gatggtgcag aaaatattga aaaggccctt ttgcttatga aaataagcc  aaaagattta    7860 attaaatcag tagttacatt ctaaaaattc atataaaaaa actgtcgcat aaaaaaatg     7920 tc                                                                  7922

<210> SEQ ID NO 41
<211> LENGTH: 1056
<212> TYPE: DNA
<213> ORGANISM: Clostridium autoethanogenum

<400> SEQUENCE: 41
atgaaaggct tcgcaatgct gggcatcaac aaactgggct ggatcgaaaa gaaaaaccct      60
gtcccaggtc cgtatgatgc tattgtgcac ccgctggcag ttagcccgtg cacttccgac     120
attcacaccg tttttgaggg tgccctgggc aaccgcgaga atatgatcct gggccatgag     180
gccgttggtg aaattgccga agtgggtagc gaagtgaaag acttcaaagt gggcgaccgt     240
gttattgtcc cgtgcaccac gccggactgg cgcagcctgg aagtgcaagc tggctttcag     300
cagcattcca atggcatgct ggcaggttgg aagttcagca atttcaaaga tggtgttttt     360
gcggactact ccatgtgaa  cgacgcggat atgaatttgg caatcctgcc ggatgagatt     420
ccgctggaga gcgcggttat gatgaccgac atgatgacca cgggttttca cggtgcggaa     480
ctggcggaca tcaagatggg cagcagcgtg tgggtgattg cattggtgc  cgtgggtctg     540 atgggtatcg cgggttcgaa gctgcgcggt gcgggtcgca ttattggcgt tgatgttcgt     600
gaggtctgcg tcgaaaccgc taagttttat ggtgccacgg acatcgtcaa ttacaaaaat     660
ggcgacattg ttgagcaaat catggatttg acccacggta agggtgtgga tcgtgttatc     720
atggcaggtg gtggcgcgga gactctggcg caagcggtta cgatggtcaa accgggtggc     780
gtgatcagca atatcaacta tcatggtagc ggcgatacgc tgccgatccc gcgtgtccag     840
tggggctgtg gtatggcaca aagaccatc  cgcggtggtc tgtgtccggg tggccgtctg     900
cgtatggaaa tgctgcgtga cttggtcctg tacaaacgtg tcgatttgtc taagctggtt     960
acccacgtat tcgatggtgc ggagaacatt gagaaagcac tgctgttgat gaagaacaag    1020
ccgaaagacc tgattaagag cgtcgttacc ttctaa                             1056

<210> SEQ ID NO 42
<211> LENGTH: 351
<212> TYPE: PRT
<213> ORGANISM: Clostridium autoethanogenum

<400> SEQUENCE: 42

Met Lys Gly Phe Ala Met Leu Gly Ile Asn Lys Leu Gly Trp Ile Glu
 1               5                  10                  15

Lys Lys Asn Pro Val Pro Gly Pro Tyr Asp Ala Ile Val His Pro Leu
```

```
                    20                  25                  30
Ala Val Ser Pro Cys Thr Ser Asp Ile His Thr Val Phe Glu Gly Ala
                35                  40                  45
Leu Gly Asn Arg Glu Asn Met Ile Leu Gly His Glu Ala Val Gly Glu
            50                  55                  60
Ile Ala Glu Val Gly Ser Glu Val Lys Asp Phe Lys Val Gly Asp Arg
65                  70                  75                  80
Val Ile Val Pro Cys Thr Thr Pro Asp Trp Arg Ser Leu Glu Val Gln
                85                  90                  95
Ala Gly Phe Gln Gln His Ser Asn Gly Met Leu Ala Gly Trp Lys Phe
            100                 105                 110
Ser Asn Phe Lys Asp Gly Val Phe Ala Asp Tyr Phe His Val Asn Asp
        115                 120                 125
Ala Asp Met Asn Leu Ala Ile Leu Pro Asp Glu Ile Pro Leu Glu Ser
    130                 135                 140
Ala Val Met Met Thr Asp Met Met Thr Thr Gly Phe His Gly Ala Glu
145                 150                 155                 160
Leu Ala Asp Ile Lys Met Gly Ser Ser Val Val Val Ile Gly Ile Gly
                165                 170                 175
Ala Val Gly Leu Met Gly Ile Ala Gly Ser Lys Leu Arg Gly Ala Gly
            180                 185                 190
Arg Ile Ile Gly Val Asp Val Arg Glu Val Cys Val Glu Thr Ala Lys
        195                 200                 205
Phe Tyr Gly Ala Thr Asp Ile Val Asn Tyr Lys Asn Gly Asp Ile Val
    210                 215                 220
Glu Gln Ile Met Asp Leu Thr His Gly Lys Gly Val Asp Arg Val Ile
225                 230                 235                 240
Met Ala Gly Gly Gly Ala Glu Thr Leu Ala Gln Ala Val Thr Met Val
                245                 250                 255
Lys Pro Gly Gly Val Ile Ser Asn Ile Asn Tyr His Gly Ser Gly Asp
            260                 265                 270
Thr Leu Pro Ile Pro Arg Val Gln Trp Gly Cys Gly Met Ala His Lys
        275                 280                 285
Thr Ile Arg Gly Gly Leu Cys Pro Gly Gly Arg Leu Arg Met Glu Met
    290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                325                 330                 335
Met Lys Asn Lys Pro Lys Asp Leu Ile Lys Ser Val Val Thr Phe
            340                 345                 350

<210> SEQ ID NO 43
<211> LENGTH: 1056
<212> TYPE: DNA
<213> ORGANISM: Clostridium autoethanogenum

<400> SEQUENCE: 43
atgaaaggct tcgcaatgct gggcatcaac aaactgggct ggatcgaaaa gaaaaaccct      60
gtcccaggtc cgtatgatgc tattgtgcac ccgctggcag ttagcccgtg cacttccgac     120
attcacaccg tttttgaggg tgccctgggc aaccgcgaga atatgatcct gggccatgag     180
gccgttggtg aaattgccga agtgggtagc gaagtgaaag acttcaaagt gggcgaccgt     240
gttattgtcc cgtgcaccac gccggactgg cgcagcctgg aagtgcaagc tggctttcag     300
```

```
cagcattcca atggcatgct ggcaggttgg aagttcagca atttcaaaga tggtgttttt      360
gcggactact tccatgtgaa cgacgcggat atgaatttgg caatcctgcc ggatgagatt      420
ccgctggaga gcgcggttat gatgaccgac atgatgacca cgggttttca cggtgcggaa      480
ctggcggaca tcaagatggg cagcagcgtg gtggtgattg gcattggtgc cgtgggtctg      540
atgggtatcg cggggttcga agctgcgcggt gcgggtcgca ttattggcgt tgaggttcgt      600
gaggtctgcg tcgaaaccgc taagttttat ggtgccacgg acatcgtcaa ttacaaaaat      660
ggcgacattg ttgagcaaat catggatttg acccacggta agggtgtgga tcgtgttatc      720
atggcaggtg gtggcgcgga gactctggcg caagcggtta cgatggtcaa accgggtggc      780
gtgatcagca atatcaacta tcatggtagc ggcgatacgc tgccgatccc gcgtgtccag      840
tggggctgtg gtatggcaca caagaccatc cgcggtggtc tgtgtccggg tggccgtctg      900
cgtatggaaa tgctgcgtga cttggtcctg tacaaacgtg tcgatttgtc taagctggtt      960
acccacgtat cgatggtgc ggagaacatt gagaaagcac tgctgttgat gaagaacaag     1020
ccgaaagacc tgattaagag cgtcgttacc ttctaa                               1056
```

```
<210> SEQ ID NO 44
<211> LENGTH: 351
<212> TYPE: PRT
<213> ORGANISM: Clostridium autoethanogenum

<400> SEQUENCE: 44

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
            165                 170                 175

Ala Val Gly Leu Met Gly Ile Ala Gly Ser Lys Leu Arg Gly Ala Gly
            180                 185                 190

Arg Ile Ile Gly Val Glu Val Arg Glu Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240
```

```
Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 45
<211> LENGTH: 1056
<212> TYPE: DNA
<213> ORGANISM: Clostridium autoethanogenum

<400> SEQUENCE: 45
atgaaaggct tcgcaatgct gggcatcaac aaactgggct ggatcgaaaa gaaaaaccct     60
gtcccaggtc cgtatgatgc tattgtgcac ccgctggcag ttagcccgtg cacttccgac    120
attcacaccg tttttgaggg tgccctgggc aaccgcgaga atatgatcct gggccatgag    180
gccgttggtg aaattgccga agtgggtagc gaagtgaaag acttcaaagt gggcgaccgt    240
gttattgtcc cgtgcaccac gccggactgg cgcagcctgg aagtgcaagc tggcttccag    300
cagcattcca atggcatgct ggcaggttgg aagttcagca atttcaaaga tggtgttttt    360
gcggactact ccatgtgaaa cgacgcggat atgaatttgg caatcctgcc ggatgagatt    420
ccgctggaga gcgcggttat gatgaccgac atgatgacca cgggttttca cggtgcggaa    480
ctggcggaca tcaagatggg cagcagcgtg gtggtgattg gcattggtgc cgtgggtctg    540
atgggtatcg cggttcgaa gctgcgcggt gcgggtcgca ttattggcgt tgatcttcgt    600
gaggtctgcg tcgaaaccgc taagttttat ggtgccacgg acatcgtcaa ttacaaaaat    660
ggcgacattg ttgagcaaat catggatttg acccacggta agggtgtgga tcgtgttatc    720
atggcaggtg gtggcgcgga gactctggcg caagcggtta cgatggtcaa accgggtggc    780
gtgatcagca atatcaacta tcatggtagc ggcgatacgc tgccgatccc gcgtgtccag    840
tggggctgtg gtatggcaca caagaccatc cgcggtggtc tgtgtccggg tggccgtctg    900
cgtatggaaa tgctgcgtga cttggtcctg tacaaacgtg tcgatttgtc taagctggtt    960
acccacgtat tcgatggtgc ggagaacatt gagaaagcac tgctgttgat gaagaacaag   1020
ccgaaagacc tgattaagag cgtcgttacc ttctaa                              1056

<210> SEQ ID NO 46
<211> LENGTH: 351
<212> TYPE: PRT
<213> ORGANISM: Clostridium autoethanogenum

<400> SEQUENCE: 46

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30
```

```
Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
 50                  55                  60

Ile Ala Glu Val Gly Ser Glu Val Lys Asp Phe Lys Val Gly Asp Arg
 65                  70                  75                  80

Val Ile Val Pro Cys Thr Thr Pro Asp Trp Arg Ser Leu Glu Val Gln
                 85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Asp Leu Arg Glu Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 47
<211> LENGTH: 1053
<212> TYPE: DNA
<213> ORGANISM: Clostridium autoethanogenum

<400> SEQUENCE: 47
atgaaaggct tcgcaatgct gggcatcaac aaactgggct ggatcgaaaa gaaaaaccct      60
gtcccaggtc cgtatgatgc tattgtgcac ccgctggcag ttagcccgtg cacttccgac     120
attcacaccg ttttttgaggg tgccctgggc aaccgcgaga atatgatcct gggccatgag    180
gccgttggtg aaattgccga agtgggtagc gaagtgaaag acttcaaagt gggcgaccgt    240
gttattgtcc cgtgcaccac gccggactgg cgcagcctgg aagtgcaagc tggctttcag    300
```

```
cagcattcca atggcatgct ggcaggttgg aagttcagca atttcaaaga tggtgttttt    360
gcggactact tccatgtgaa cgacgcggat atgaatttgg caatcctgcc ggatgagatt    420
ccgctggaga gcgcggttat gatgaccgac atgatgacca cgggttttca cggtgcggaa    480
ctggcggaca tcaagatggg cagcagcgtg gtggtgattg gcattggtgc cgtgggtctg    540
atgggtatcg cgggttcgaa gctgcgcggt gcgggtcgca ttattggcga tgttcgtgag    600
gtctgcgtcg aaaccgctaa gttttatggt gccacggaca tcgtcaattt caaaaatggc    660
gacattgttg agcaaatcat ggatttgacc cacggtaagg gtgtggatcg tgttatcatg    720
gcaggtggtg cgcgggagac tctggcgcaa gcggttacga tggtcaaacc gggtggcgtg    780
atcagcaata tcaactatca tggtagcggc gatacgctgc cgatcccgcg tgtccagtgg    840
ggctgtggta tggcacacaa gaccatccgc ggtggtctgt gtccgggtgg ccgtctgcgt    900
atggaaatgc tgcgtgactt ggtcctgtac aaacgtgtcg atttgtctaa gctggttacc    960
cacgtattcg atggtgcgga gaacattgag aaagcactgc tgttgatgaa gaacaagccg   1020
aaagacctga ttaagagcgt cgttaccttc taa                                1053
```

<210> SEQ ID NO 48
<211> LENGTH: 351
<212> TYPE: PRT
<213> ORGANISM: Clostridium autoethanogenum

<400> SEQUENCE: 48

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Asp Val Arg Glu Val Cys Val Glu Thr Ala Lys
        195                 200                 205

Phe Tyr Gly Ala Thr Asp Ile Val Asn Phe Lys Asn Gly Asp Ile Val
    210                 215                 220

Glu Gln Ile Met Asp Leu Thr His Gly Lys Gly Val Asp Arg Val Ile
225                 230                 235                 240
```

```
Met Ala Gly Gly Gly Ala Glu Thr Leu Ala Gln Ala Val Thr Met Val
            245                 250                 255

Lys Pro Gly Gly Val Ile Ser Asn Ile Asn Tyr His Gly Ser Gly Asp
        260                 265                 270

Thr Leu Pro Ile Pro Arg Val Gln Trp Gly Cys Gly Met Ala His Lys
    275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 49
<211> LENGTH: 1056
<212> TYPE: DNA
<213> ORGANISM: Clostridium autoethanogenum

<400> SEQUENCE: 49
atgaaaggct tcgcaatgct gggcatcaac aaactgggct ggatcgaaaa gaaaaaccct      60
gtcccaggtc cgtatgatgc tattgtgcac ccgctggcag ttagcccgtg cacttccgac     120
attcacaccg tttttgaggg tgccctgggc aaccgcgaga atatgatcct gggccatgag     180
gccgttggtg aaattgccga agtgggtagc gaagtgaaag acttcaaagt gggcgaccgt     240
gttattgtcc cgtgcaccac gccggactgg cgcagcctgg aagtgcaagc tggctttcag     300
cagcattcca atggcatgct ggcaggttgg aagttcagca atttcaaaga tggtgttttt     360
gcggactact ccatgtgaaa cgacgcggat atgaatttgg caatcctgcc ggatgagatt     420
ccgctggaga gcgcggttat gatgaccgac atgatgacca cgggttttca cggtgcggaa     480
ctggcggaca tcaagatggg cagcagcgtg gtggtgattg gcattggtgc cgtgggtctg     540
atgggtatcg cgggttcgaa gctgcgcggt gcgggtcgca ttattggcgt tgatgttcgt     600
gaggtctgcg tcgaaaccgc taagttttat ggtgccacgg acatcgtcaa tgccaaaaat     660
ggcgacattg ttgagcaaat catggatttg acccacggta agggtgtgga tcgtgttatc     720
atggcaggtg gtgcgcgcga gactctggcg caagcggtta cgatggtcaa accgggtggc     780
gtgatcagca atatcaacta tcatggtagc ggcgatacgc tgccgatccc gcgtgtccag     840
tggggctgtg gtatggcaca caagaccatc cgcggtggtc tgtgtccggg tggccgtctg     900
cgtatggaaa tgctgcgtga cttggtcctg tacaaacgtg tcgatttgtc taagctggtt     960
acccacgtat tcgatggtgc ggagaacatt gagaaagcac tgctgttgat gaagaacaag    1020
ccgaaagacc tgattaagag cgtcgttacc ttctaa                              1056

<210> SEQ ID NO 50
<211> LENGTH: 351
<212> TYPE: PRT
<213> ORGANISM: Clostridium autoethanogenum

<400> SEQUENCE: 50

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30
```

Ala Val Ser Pro Cys Thr Ser Asp Ile His Thr Val Phe Glu Gly Ala
         35                  40                  45

Leu Gly Asn Arg Glu Asn Met Ile Leu Gly His Glu Ala Val Gly Glu
 50                  55                  60

Ile Ala Glu Val Gly Ser Glu Val Lys Asp Phe Lys Val Gly Asp Arg
 65                  70                  75                  80

Val Ile Val Pro Cys Thr Thr Pro Asp Trp Arg Ser Leu Glu Val Gln
                 85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Asp Val Arg Glu Val Cys Val Glu Thr Ala Lys
        195                 200                 205

Phe Tyr Gly Ala Thr Asp Ile Val Asn Ala Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 51
<211> LENGTH: 1056
<212> TYPE: DNA
<213> ORGANISM: Clostridium autoethanogenum

<400> SEQUENCE: 51
atgaaaggct tcgcaatgct gggcatcaac aaactgggct ggatcgaaaa gaaaaaccct      60
gtcccaggtc cgtatgatgc tattgtgcac ccgctggcag ttagcccgtg cacttccgac     120
attcacaccg tttttgaggg tgccctgggc aaccgcgaga atatgatcct gggccatgag     180
gccgttggtg aaattgccga agtgggtagc gaagtgaaag acttcaaagt gggcgaccgt     240
gttattgtcc cgtgcaccac gccggactgg cgcagcctgg aagtgcaagc tggctttcag     300
cagcattcca atggcatgct ggcaggttgg aagttcagca atttcaaaga tggtgttttt     360

```
gcggactact tccatgtgaa cgacgcggat atgaatttgg caatcctgcc ggatgagatt      420
ccgctggaga gcgcggttat gatgaccgac atgatgacca cgggttttca cggtgcggaa      480
ctggcggaca tcaagatggg cagcagcgtg gtggtgattg cattggtgc cgtgggtctg       540 atgggtatcg cgggttcgaa gctgcgcggt gcgggtcgca ttattggcgt tgatgatcgt      600
gaggtctgcg tcgaaaccgc taagttttat ggtgccacgg acatcgtcaa ttacaaaaat      660
ggcgacattg ttgagcaaat catggatttg acccacggta agggtgtgga tcgtgttatc      720
atggcaggtg gtggcgcgga gactctggcg caagcggtta cgatggtcaa accgggtggc      780
gtgatcagca atatcaacta tcatggtagc ggcgatacgc tgccgatccc gcgtgtccag      840
tggggctgtg gtatggcaca aagaccatc cgcggtggtc tgtgtccggg tggccgtctg       900
cgtatggaaa tgctgcgtga cttggtcctg tacaaacgtg tcgatttgtc taagctggtt      960
acccacgtat tcgatggtgc ggagaacatt gagaaagcac tgctgttgat gaagaacaag     1020
ccgaaagacc tgattaagag cgtcgttacc ttctaa                                1056
```

<210> SEQ ID NO 52
<211> LENGTH: 351
<212> TYPE: PRT
<213> ORGANISM: Clostridium autoethanogenum

<400> SEQUENCE: 52

```
Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile
                165                 170                 175

Ala Val Gly Leu Met Gly Ile Ala Gly Ser Lys Leu Arg Gly Ala Gly
            180                 185                 190

Arg Ile Ile Gly Val Asp Asp Arg Glu Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
```

Lys Pro Gly Gly Val Ile Ser Asn Ile Asn Tyr His Gly Ser Gly Asp
            245                 250                 255
                260                 265                 270

Thr Leu Pro Ile Pro Arg Val Gln Trp Gly Cys Gly Met Ala His Lys
            275                 280                 285

Thr Ile Arg Gly Gly Leu Cys Pro Gly Gly Arg Leu Arg Met Glu Met
        290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 53
<211> LENGTH: 1056
<212> TYPE: DNA
<213> ORGANISM: Clostridium autoethanogenum

<400> SEQUENCE: 53
atgaaaggtt ttgcaatgtt aggtattaac aaattaggat ggattgaaaa gaaaaaccca    60
gtgccaggtc cttatgatgc gattgtacat cctctagctg tatccccatg tacatcagat   120
atacatacgg tttttgaagg agcacttggt aataggaaa atatgatttt aggccatgaa   180
gctgtaggtg aaatagccga agttggcagc gaagttaaag attttaaagt tggcgataga   240
gttatcgtac catgcacaac acctgactgg agatctttag aagtccaagc tggttttcag   300
cagcattcaa acggtatgct tgcaggatgg aagttttcca attttaaaga tggtgtattt   360
gcagattact tcatgtaaa cgatgcagat atgaatcttg ccatactccc agatgaaata   420
cctttagaaa gtgcagttat gatgacagac atgatgacta ctggttttca tggagcagaa   480
cttgcagaca taaaaatggg ctccagcgtt gtagtaattg gtataggagc tgttggatta   540
atgggaatag ccggttccaa acttcgagga gcaggcagaa ttatcggtgt ggaagcagaa   600
cctgtttgtg ttgaaacagc taaatttat ggagcaactg atattgtaaa tgctaaaaat   660
ggtgatatag ttgaacaaat catggactta actcatggta aaggtgtaga ccgtgtaatc   720
atggcaggcg gtggtgctga acactagca caagcagtaa ctatggttaa acctggcggc   780
gtaatttcta acatcaacta ccatggaagc ggtgatactt taccaatacc tcgtgttcaa   840
tggggctgcg gcatggctca aaaactata agaggaggat tatgccccgg cggacgtctt   900
agaatggaaa tgctaagaga tcttgttcta tataaacgtg ttgatttgag taaacttgtt   960
actcatgtat ttgatggtgc agaaaatatt gaaaaggccc ttttgcttat gaaaaataag  1020
ccaaaagatt taattaaatc agtagttaca ttctaa                            1056

<210> SEQ ID NO 54
<211> LENGTH: 351
<212> TYPE: PRT
<213> ORGANISM: Clostridium autoethanogenum

<400> SEQUENCE: 54

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala

```
                 35                  40                  45
Leu Gly Asn Arg Glu Asn Met Ile Leu Gly His Glu Ala Val Gly Glu
             50                  55                  60
Ile Ala Glu Val Gly Ser Glu Val Lys Asp Phe Lys Val Gly Asp Arg
65                  70                  75                  80
Val Ile Val Pro Cys Thr Thr Pro Asp Trp Arg Ser Leu Glu Val Gln
                 85                  90                  95
Ala Gly Phe Gln Gln His Ser Asn Gly Met Leu Ala Gly Trp Lys Phe
            100                 105                 110
Ser Asn Phe Lys Asp Gly Val Phe Ala Asp Tyr Phe His Val Asn Asp
            115                 120                 125
Ala Asp Met Asn Leu Ala Ile Leu Pro Asp Glu Ile Pro Leu Glu Ser
            130                 135                 140
Ala Val Met Met Thr Asp Met Met Thr Thr Gly Phe His Gly Ala Glu
145                 150                 155                 160
Leu Ala Asp Ile Lys Met Gly Ser Ser Val Val Ile Gly Ile Gly
                165                 170                 175
Ala Val Gly Leu Met Gly Ile Ala Gly Ser Lys Leu Arg Gly Ala Gly
            180                 185                 190
Arg Ile Ile Gly Val Gly Ser Arg Pro Val Cys Val Glu Thr Ala Lys
            195                 200                 205
Phe Tyr Gly Ala Thr Asp Ile Val Asn Ala Lys Asn Gly Asp Ile Val
            210                 215                 220
Glu Gln Ile Met Asp Leu Thr His Gly Lys Gly Val Asp Arg Val Ile
225                 230                 235                 240
Met Ala Gly Gly Gly Ala Glu Thr Leu Ala Gln Ala Val Thr Met Val
                245                 250                 255
Lys Pro Gly Gly Val Ile Ser Asn Ile Asn Tyr His Gly Ser Gly Asp
            260                 265                 270
Thr Leu Pro Ile Pro Arg Val Gln Trp Gly Cys Gly Met Ala His Lys
            275                 280                 285
Thr Ile Arg Gly Gly Leu Cys Pro Gly Gly Arg Leu Arg Met Glu Met
            290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                325                 330                 335
Met Lys Asn Lys Pro Lys Asp Leu Ile Lys Ser Val Val Thr Phe
            340                 345                 350

<210> SEQ ID NO 55
<211> LENGTH: 1062
<212> TYPE: DNA
<213> ORGANISM: Clostridium autoethanogenum

<400> SEQUENCE: 55
acagttaaaa agcatatcta acagtccttc cactgtacta attcaaggcg aaagcggtac      60
aggtaaagaa cttattgcgc agtccatcca caatgacagc agcagaaaaa ataacagctt     120
tatagcaata aattgcggtg ccatacccaa aaatttaata gaaagtgaat tattcggata     180
tgaagatgga tcattcacag gtgcaaaaca tggagggcgt gcaggaaaat ttgaacttgc     240
aaatggtggt actttatttt tagatgaaat tgggaaatg cctttagata tgcaagtaaa     300
tcttttaaga gttctccaag aaaactgtat tacaagaata ggcgggaaca gatgtgtaaa     360
```

```
aatagatata agaatcattg cagctactaa taaaaatttg agggaagaaa tacataaagg      420
aacttttcgc gaagatttat actatagact aaatgtaata cctatatatg taccaccact      480
gcgggaaaga gatatggata ttaaaatact gataaactat ttttaaaga taaaagcttt      540 taaacttaaa aaacctattc caatagtaag acctgatata tatcaaaagc tcttaaatta      600
taattggccc ggaaatgtaa gagaattgga aaattgtatt gaaatatcg taaatatgaa       660 tggaaataca tctttcaact tcgaaaatag tatttcagta aatacgcaaa ctagtccttg      720
tactacaaaa tttaaatatg atatgtattc attaaaagag ttggaaaaag aagcaataac      780
aaattgtatg agtaattgca atggtaacat tgcaaaagct tctaaaattc tgggaataaa      840
tagaagtact ttgtatacaa aaataaaaaa atatcaaatt aatttttctt aaagtgtatg      900
taaacacaac tttgttgtaa aaagcaacat tattttctta aaaaatgttg ctttttacag      960
catttttcaa ttatatatat taaccttata aagtcctacc ccctaaatt caacctttc      1020 atgataaaaa acatactggc acaacatttg cttatatatt ta                       1062

<210> SEQ ID NO 56
<211> LENGTH: 823
<212> TYPE: DNA
<213> ORGANISM: Clostridium autoethanogenum

<400> SEQUENCE: 56
cgtattttta attgcgaact taagatttaa ttaatatcta ctatgagtaa gtcaacatat      60
atacctaaat tatgataaaa ttatatatta taatttcaaa ataaacataa ctataataat      120
acactaagat aaagctattt atctgatggc tacctactgt aacactccct cttctatcaa      180
agtgagagat aacagtagct acgcccctag ataattcatc taaacttagt gggagaaaca      240
aaactctaaa gagaaagcga ttcactttaa atcaaagatt tgagatatct gcttctccca      300
ctaagtaaga ttcattgata taaaaggaa ggtaatctaa taatgtttaa accatttact       360
catagtgaaa tagtcagtag gtctcttaat agatgcatta aataccatat agaaaaggt       420 ataccaaaac ctaacgaac acttagtcgc aaagaattgg acaacttaat aaaagaaaac      480
aacgatatta taaaaatagc aaaaccattt atggaaatac tttatgattt tttaagtgga      540
tcaggtttct cattatatct cacagacaaa aatggaattg tattaactat cataggtgac      600
aaagatattg taatggagca ggcaaaggct ggaatagcag aaggtattga tctgagtgaa      660
caaagtgcag gtacaaatgc agcaggaact gctattttg aaaatttgtc agttcaactt       720
tcaggcaaag aacattttat aaatactttt cagatttata cctgctctgc atctgtcata      780
cataacgaac aaggaaatat aatcggatgt ctaactttaa ctg                       823

<210> SEQ ID NO 57
<211> LENGTH: 39
<212> TYPE: DNA
<213> ORGANISM: Artificial sequence
<220> FEATURE:
<223> OTHER INFORMATION: synthetic primer

<400> SEQUENCE: 57
attcatcctg caggacagtt aaaaagcata tctaacagt                            39

<210> SEQ ID NO 58
<211> LENGTH: 37
<212> TYPE: DNA
<213> ORGANISM: Artificial sequence
<220> FEATURE:
<223> OTHER INFORMATION: synthetic primer
```

```
<400> SEQUENCE: 58
gactgcggcc gctaaatata taagcaaatg ttgtgcc                              37

<210> SEQ ID NO 59
<211> LENGTH: 34
<212> TYPE: DNA
<213> ORGANISM: Artificial sequence
<220> FEATURE:
<223> OTHER INFORMATION: synthetic primer

<400> SEQUENCE: 59
atatgctagc gtatttttaa ttgcgaactt aaga                                 34

<210> SEQ ID NO 60
<211> LENGTH: 36
<212> TYPE: DNA
<213> ORGANISM: Artificial sequence
<220> FEATURE:
<223> OTHER INFORMATION: synthetic primer

<400> SEQUENCE: 60
gactggcgcg ccagttaaag ttagacatcc gattat                               36

<210> SEQ ID NO 61
<211> LENGTH: 25
<212> TYPE: DNA
<213> ORGANISM: Artificial sequence
<220> FEATURE:
<223> OTHER INFORMATION: synthetic primer

<400> SEQUENCE: 61
ttggaatttt agctgtagat aacaa                                           25

<210> SEQ ID NO 62
<211> LENGTH: 25
<212> TYPE: DNA
<213> ORGANISM: Artificial sequence
<220> FEATURE:
<223> OTHER INFORMATION: synthetic primer

<400> SEQUENCE: 62
taagtgattt tcaatggact ttact                                           25

<210> SEQ ID NO 63
<211> LENGTH: 351
<212> TYPE: PRT
<213> ORGANISM: Clostridium autoethanogenum

<400> SEQUENCE: 63
```

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
                20                  25                  30

Ala Val Ser Pro Cys Thr Ser Asp Ile His Thr Val Phe Glu Gly Ala
            35                  40                  45

Leu Gly Asn Arg Glu Asn Met Ile Leu Gly His Glu Ala Val Gly Glu
        50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

```
Ala Gly Phe Gln Gln His Ser Asn Gly Met Leu Ala Gly Trp Lys Phe
                100                 105                 110

Ser Asn Phe Lys Asp Gly Val Phe Ala Asp Tyr Phe His Val Asn Asp
            115                 120                 125

Ala Asp Met Asn Leu Ala Ile Leu Pro Asp Glu Ile Pro Leu Glu Ser
        130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Asp Val Arg Glu Val Cys Val Glu Thr Ala Lys
        195                 200                 205

Phe Tyr Gly Ala Thr Asp Ile Val Asn Gly Lys Asn Gly Asp Ile Val
210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350

<210> SEQ ID NO 64
<211> LENGTH: 351
<212> TYPE: PRT
<213> ORGANISM: Clostridium autoethanogenum

<400> SEQUENCE: 64

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
                20                  25                  30

Ala Val Ser Pro Cys Thr Ser Asp Ile His Thr Val Phe Glu Gly Ala
            35                  40                  45

Leu Gly Asn Arg Glu Asn Met Ile Leu Gly His Glu Ala Val Gly Glu
        50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125
```

Ala Asp Met Asn Leu Ala Ile Leu Pro Asp Glu Ile Pro Leu Glu Ser
              130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Ile Gly Ile Gly
                165                 170                 175

Ala Val Gly Leu Met Gly Ile Ala Gly Ser Lys Leu Arg Gly Ala Gly
              180                 185                 190

Arg Ile Ile Gly Val Asp Val Arg Glu Val Cys Val Glu Thr Ala Lys
              195                 200                 205

Phe Tyr Gly Ala Thr Asp Ile Val Asn Ser Lys Asn Gly Asp Ile Val
              210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
                260                 265                 270

Thr Leu Pro Ile Pro Arg Val Gln Trp Gly Cys Gly Met Ala His Lys
              275                 280                 285

Thr Ile Arg Gly Gly Leu Cys Pro Gly Gly Arg Leu Arg Met Glu Met
290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
              340                 345                 350

<210> SEQ ID NO 65
<211> LENGTH: 351
<212> TYPE: PRT
<213> ORGANISM: Clostridium autoethanogenum

<400> SEQUENCE: 65

Met Lys Gly Phe Ala Met Leu Gly Ile Asn Lys Leu Gly Trp Ile Glu
1               5                   10                  15

Lys Lys Asn Pro Val Pro Gly Pro Tyr Asp Ala Ile Val His Pro Leu
                20                  25                  30

Ala Val Ser Pro Cys Thr Ser Asp Ile His Thr Val Phe Glu Gly Ala
              35                  40                  45

Leu Gly Asn Arg Glu Asn Met Ile Leu Gly His Glu Ala Val Gly Glu
          50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
              100                 105                 110

Ser Asn Phe Lys Asp Gly Val Phe Ala Asp Tyr Phe His Val Asn Asp
              115                 120                 125

Ala Asp Met Asn Leu Ala Ile Leu Pro Asp Glu Ile Pro Leu Glu Ser
              130                 135                 140

Ala Val Met Met Thr Asp Met Met Thr Thr Gly Phe His Gly Ala Glu

```
                145                 150                 155                 160
Leu Ala Asp Ile Lys Met Gly Ser Ser Val Val Ile Gly Ile Gly
                    165                 170                 175
Ala Val Gly Leu Met Gly Ile Ala Gly Ser Lys Leu Arg Gly Ala Gly
                180                 185                 190
Arg Ile Ile Gly Val Asp Val Arg Glu Val Cys Val Glu Thr Ala Lys
                195                 200                 205
Phe Tyr Gly Ala Thr Asp Ile Val Asn Val Lys Asn Gly Asp Ile Val
                210                 215                 220
Glu Gln Ile Met Asp Leu Thr His Gly Lys Gly Val Asp Arg Val Ile
225                 230                 235                 240
Met Ala Gly Gly Gly Ala Glu Thr Leu Ala Gln Ala Val Thr Met Val
                    245                 250                 255
Lys Pro Gly Gly Val Ile Ser Asn Ile Asn Tyr His Gly Ser Gly Asp
                260                 265                 270
Thr Leu Pro Ile Pro Arg Val Gln Trp Gly Cys Gly Met Ala His Lys
                275                 280                 285
Thr Ile Arg Gly Gly Leu Cys Pro Gly Gly Arg Leu Arg Met Glu Met
                290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                    325                 330                 335
Met Lys Asn Lys Pro Lys Asp Leu Ile Lys Ser Val Val Thr Phe
                340                 345                 350

<210> SEQ ID NO 66
<211> LENGTH: 351
<212> TYPE: PRT
<213> ORGANISM: Clostridium autoethanogenum

<400> SEQUENCE: 66

Met Lys Gly Phe Ala Met Leu Gly Ile Asn Lys Leu Gly Trp Ile Glu
1                   5                   10                  15
Lys Lys Asn Pro Val Pro Gly Pro Tyr Asp Ala Ile Val His Pro Leu
                20                  25                  30
Ala Val Ser Pro Cys Thr Ser Asp Ile His Thr Val Phe Glu Gly Ala
                35                  40                  45
Leu Gly Asn Arg Glu Asn Met Ile Leu Gly His Glu Ala Val Gly Glu
            50                  55                  60
Ile Ala Glu Val Gly Ser Glu Val Lys Asp Phe Lys Val Gly Asp Arg
65                  70                  75                  80
Val Ile Val Pro Cys Thr Thr Pro Asp Trp Arg Ser Leu Glu Val Gln
                85                  90                  95
Ala Gly Phe Gln Gln His Ser Asn Gly Met Leu Ala Gly Trp Lys Phe
                100                 105                 110
Ser Asn Phe Lys Asp Gly Val Phe Ala Asp Tyr Phe His Val Asn Asp
                115                 120                 125
Ala Asp Met Asn Leu Ala Ile Leu Pro Asp Glu Ile Pro Leu Glu Ser
                130                 135                 140
Ala Val Met Met Thr Asp Met Met Thr Thr Gly Phe His Gly Ala Glu
145                 150                 155                 160
Leu Ala Asp Ile Lys Met Gly Ser Ser Val Val Ile Gly Ile Gly
                    165                 170                 175
```

```
Ala Val Gly Leu Met Gly Ile Ala Gly Ser Lys Leu Arg Gly Ala Gly
            180                 185                 190
Arg Ile Ile Gly Val Gly Glu Arg Pro Val Cys Val Glu Thr Ala Lys
        195                 200                 205
Phe Tyr Gly Ala Thr Asp Ile Val Asn Tyr Lys Asn Gly Asp Ile Val
    210                 215                 220
Glu Gln Ile Met Asp Leu Thr His Gly Lys Gly Val Asp Arg Val Ile
225                 230                 235                 240
Met Ala Gly Gly Ala Glu Thr Leu Ala Gln Ala Val Thr Met Val
                245                 250                 255
Lys Pro Gly Gly Val Ile Ser Asn Ile Asn Tyr His Gly Ser Gly Asp
            260                 265                 270
Thr Leu Pro Ile Pro Arg Val Gln Trp Gly Cys Gly Met Ala His Lys
        275                 280                 285
Thr Ile Arg Gly Gly Leu Cys Pro Gly Gly Arg Leu Arg Met Glu Met
    290                 295                 300
Leu Arg Asp Leu Val Leu Tyr Lys Arg Val Asp Leu Ser Lys Leu Val
305                 310                 315                 320
Thr His Val Phe Asp Gly Ala Glu Asn Ile Glu Lys Ala Leu Leu Leu
                325                 330                 335
Met Lys Asn Lys Pro Lys Asp Leu Ile Lys Ser Val Val Thr Phe
            340                 345                 350
```

<210> SEQ ID NO 67
<211> LENGTH: 1053
<212> TYPE: DNA
<213> ORGANISM: Clostridium autoethanogenum

<400> SEQUENCE: 67

```
atgaaaggct tcgcaatgct gggcatcaac aaactgggct ggatcgaaaa gaaaaaccct    60
gtcccaggtc cgtatgatgc tattgtgcac ccgctggcag ttagcccgtg cacttccgac   120
attcacaccg tttttgaggg tgccctgggc aaccgcgaga atatgatcct gggccatgag   180
gccgttggtg aaattgccga agtgggtagc gaagtgaaag acttcaaagt gggcgaccgt   240
gttattgtcc cgtgcaccac gccggactgg cgcagcctgg aagtgcaagc tggctttcag   300
cagcattcca atggcatgct ggcaggttgg aagttcagca atttcaaaga tggtgttttt   360
gcggactact ccatgtgaa cgacgcggat atgaatttgg caatcctgcc ggatgagatt   420
ccgctggaga gcgcggttat gatgaccgac atgatgacca cgggttttca cggtgcggaa   480
ctggcggaca tcaagatggg cagcagcgtg gtggtgattg cattggtgc cgtgggtctg   540
atgggtatcg cgggttcgaa gctgcgcggt gcgggtcgca ttattggcga tgatcgtgag   600
gtctgcgtcg aaaccgctaa gttttatggt gccacggaca tcgtcaatgg taaaaatggc   660
gacattgttg agcaaatcat ggatttgacc cacggtaagg gtgtggatcg tgttatcatg   720
gcaggtggtg gcgcggagac tctggcgcaa gcggttacga tggtcaaacc gggtggcgtg   780
atcagcaata tcaactatca tggtagcggc gatacgctgc cgatcccgcg tgtccagtgg   840
ggctgtggta tggcacacaa gaccatccgc ggtggtctgt gtccgggtgg ccgtctgcgt   900
atggaaatgc tgcgtgactt ggtcctgtac aacgtgtcg atttgtctaa gctggttacc   960
cacgtattcg atggtgcgga gaacattgag aaagcactgc tgttgatgaa gaacaagccg  1020
aaagacctga ttaagagcgt cgttaccttc taa                                1053
```

<210> SEQ ID NO 68

```
<211> LENGTH: 1053
<212> TYPE: DNA
<213> ORGANISM: Clostridium autoethanogenum

<400> SEQUENCE: 68
atgaaaggct tcgcaatgct gggcatcaac aaactgggct ggatcgaaaa gaaaaaccct     60
gtcccaggtc cgtatgatgc tattgtgcac ccgctggcag ttagcccgtg cacttccgac    120
attcacaccg tttttgaggg tgccctgggc aaccgcgaga atatgatcct gggccatgag    180
gccgttggtg aaattgccga agtgggtagc gaagtgaaag acttcaaagt gggcgaccgt    240
gttattgtcc cgtgcaccac gccggactgg cgcagcctgg aagtgcaagc tggctttcag    300
cagcattcca atggcatgct ggcaggttgg aagttcagca atttcaaaga tggtgttttt    360
gcggactact ccatgtgaac gacgcggat atgaatttgg caatcctgcc ggatgagatt    420
ccgctggaga gcgcggttat gatgaccgac atgatgacca cggttttca cggtgcggaa    480
ctggcggaca tcaagatggg cagcagcgtg gtggtgattg cattggtgc cgtgggtctg    540
atgggtatcg cgggttcgaa gctgcgcggt gcgggtcgca ttattggcga tgatcgtgag    600
gtctgcgtcg aaaccgctaa gttttatggt gccacggaca tcgtcaattc taaaaatggc    660
gacattgttg agcaaatcat ggatttgacc cacggtaagg gtgtggatcg tgttatcatg    720
gcaggtggtg gcgcggagac tctggcgcaa gcggttacga tggtcaaacc gggtggcgtg    780
atcagcaata tcaactatca tggtagcggc gatacgctgc cgatcccgcg tgtccagtgg    840
ggctgtggta tggcacacaa gaccatccgc ggtggtctgt gtccgggtgg ccgtctgcgt    900
atggaaatgc tgcgtgactt ggtcctgtac aaacgtgtcg atttgtctaa gctggttacc    960
cacgtattcg atggtgcgga gaacattgag aaagcactgc tgttgatgaa gaacaagccg   1020
aaagacctga ttaagagcgt cgttaccttc taa                                1053

<210> SEQ ID NO 69
<211> LENGTH: 1053
<212> TYPE: DNA
<213> ORGANISM: Clostridium autoethanogenum

<400> SEQUENCE: 69
atgaaaggct tcgcaatgct gggcatcaac aaactgggct ggatcgaaaa gaaaaaccct     60
gtcccaggtc cgtatgatgc tattgtgcac ccgctggcag ttagcccgtg cacttccgac    120
attcacaccg tttttgaggg tgccctgggc aaccgcgaga atatgatcct gggccatgag    180
gccgttggtg aaattgccga agtgggtagc gaagtgaaag acttcaaagt gggcgaccgt    240
gttattgtcc cgtgcaccac gccggactgg cgcagcctgg aagtgcaagc tggctttcag    300
cagcattcca atggcatgct ggcaggttgg aagttcagca atttcaaaga tggtgttttt    360
gcggactact ccatgtgaac gacgcggat atgaatttgg caatcctgcc ggatgagatt    420
ccgctggaga gcgcggttat gatgaccgac atgatgacca cggttttca cggtgcggaa    480
ctggcggaca tcaagatggg cagcagcgtg gtggtgattg cattggtgc cgtgggtctg    540
atgggtatcg cgggttcgaa gctgcgcggt gcgggtcgca ttattggcga tgatcgtgag    600
gtctgcgtcg aaaccgctaa gttttatggt gccacggaca tcgtcaatgt taaaaatggc    660
gacattgttg agcaaatcat ggatttgacc cacggtaagg gtgtggatcg tgttatcatg    720
gcaggtggtg gcgcggagac tctggcgcaa gcggttacga tggtcaaacc gggtggcgtg    780
atcagcaata tcaactatca tggtagcggc gatacgctgc cgatcccgcg tgtccagtgg    840
ggctgtggta tggcacacaa gaccatccgc ggtggtctgt gtccgggtgg ccgtctgcgt    900
```

-continued

```
atggaaatgc tgcgtgactt ggtcctgtac aaacgtgtcg atttgtctaa gctggttacc    960
cacgtattcg atggtgcgga gaacattgag aaagcactgc tgttgatgaa gaacaagccg   1020
aaagacctga ttaagagcgt cgttaccttc taa                                1053

<210> SEQ ID NO 70
<211> LENGTH: 1056
<212> TYPE: DNA
<213> ORGANISM: Clostridium autoethanogenum

<400> SEQUENCE: 70
atgaaaggct cgcaatgct gggcatcaac aaactgggct ggatcgaaaa gaaaaaccct      60
gtcccaggtc cgtatgatgc tattgtgcac ccgctggcag ttagcccgtg cacttccgac   120
attcacaccg tttttgaggg tgccctgggc aaccgcgaga atatgatcct gggccatgag   180
gccgttggtg aaattgccga agtgggtagc gaagtgaaag acttcaaagt gggcgaccgt   240
gttattgtcc cgtgcaccac gccggactgg cgcagcctgg aagtgcaagc tggctttcag   300
cagcattcca atggcatgct ggcaggttgg aagttcagca atttcaaaga tggtgttttt   360
gcggactact tccatgtgaa cgacgcggat atgaatttgg caatcctgcc ggatgagatt   420
ccgctggaga gcgcggttat gatgaccgac atgatgacca cgggttttca cggtgcggaa   480
ctggcggaca tcaagatggg cagcagcgtg gtggtgattg gcattggtgc cgtgggtctg   540
atgggtatcg cgggttcgaa gctgcgcggt gcgggtcgca ttattggcgt tgatgttgaa   600
gaggtctgcg tcgaaaccgc taagttttat ggtgccacgg acatcgtcaa tgctaaaaat   660
ggcgacattg ttgagcaaat catggatttg acccacggta agggtgtgga tcgtgttatc   720
atggcaggtg gtggcgcgga gactctggcg caagcggtta cgatggtcaa accgggtggc   780
gtgatcagca atatcaacta tcatggtagc ggcgatacgc tgccgatccc gcgtgtccag   840
tggggctgtg gtatggcaca caagaccatc cgcggtggtc tgtgtccggg tggccgtctg   900
cgtatggaaa tgctgcgtga cttggtcctg tacaaacgtg tcgatttgtc taagctggtt   960
acccacgtat tcgatggtgc ggagaacatt gagaaagcac tgctgttgat gaagaacaag   1020
ccgaaagacc tgattaagag cgtcgttacc ttctaa                              1056
```

ENZYME-ALTERED METABOLITE ACTIVITY

CROSS REFERENCE TO RELATED APPLICATION

This application claims priority to U.S. provisional application No. 61/620,538 filed on Apr. 5, 2012. The content of the above referenced application is incorporated herein in its entirety.

FIELD OF THE INVENTION

The present invention relates to mutant alcohol dehydrogenase enzymes, microorganisms comprising same, and methods for the production of one or more products by microbial fermentation.

BACKGROUND

Production of alcohols such as ethanol or butanol by fermentation with microorganisms is well known and has been industrially used since centuries. Historically, ethanol fermentation is the largest process. Acetone-butanol-ethanol (ABE) fermentation is considered as the second largest fermentation process [Duerre P: Production of solvents. In: Handbook on Clostridia, CRC Press, 2005: 671-696] and current production capacity in countries like China exceeds 1,000,000 tons [Ni Y and Sun Z: Recent progress on industrial fermentative production of acetone-butanol-ethanol by *Clostridium acetobutylicum* in China. Appl. Microbiol. Biotechnol., 2009, 83: 415-423]. Butanol is usually used as solvent or biofuel, while acetone is considered as an unwanted by-product [Duerre P: Production of solvents. In: Handbook on Clostridia, CRC Press, 2005: 671-696]. A few isolates of *Clostridium beijerinckii* are known to produce isopropanol instead of acetone due to a secondary alcohol dehydrogenase [George H A, Johnson J L, Moore W E C, Holdeman L V, Chen J S: Acetone, isopropanol, and butanol production by *Clostridium beijerinckii* (syn. *Clostridium butylicum*) and *Clostridium aurantibutyricum*. Appl Environ Microbiol 45: 1160-1163]. Isopropanol has similar properties as butanol and would be beneficial over acetone. However, the reduction is not very efficient and respective *Clostridium beijerinckii* strains don't produce good titers and are not considered as useful production strains.

Recently, *C. acetobutylicum* has been metabolically engineered for isopropanol production using a secondary alcohol dehydrogenase from *C. beijerinckii* [Lee et al, 2012: Metabolic engineering of *Clostridium acetobutylicum* ATCC824 for isopropanol-butanol-ethanol fermentation, *Appl. Environ. Microbiol.* 78: 1416-1423], but a highly efficient alcohol dehydrogenase would be required to optimize this process.

A challenge of the ABE fermentation is that all known organisms rely on sugar or starch based substrates. The cost of many carbohydrate feed stocks suitable for the production of chemical products such as acetone and isopropanol is influenced by their value as human food or animal feed, and the cultivation of starch or sucrose-producing crops for such production is not economically sustainable in all geographies. Therefore, it is of interest to develop technologies to convert lower cost and/or more abundant carbon resources into useful chemical products such as acetone and isopropanol.

CO is a major free energy-rich by-product of the incomplete combustion of organic materials such as coal or oil and oil derived products. For example, the steel industry in Australia is reported to produce and release into the atmosphere over 500,000 tonnes of CO annually. Acetogenic organisms such as the closely related microorganisms *Clostridium autoethanogenum*, *C. ljungdahlii*, and *C. ragsdalei* are able to grow chemoautotrophically on CO or $CO_2/H_2$ containing gases as sole energy and carbon source and synthesize products such as acetate, ethanol, or 2,3-butanediol, but neither acetone nor isopropanol [Munasinghe P C, Khanal S K: Biomass-derived syngas fermentation into biofuels: Opportunities and challenges. *Bioresource Technol* 2010, 5013-22].

Recently, production of isopropanol was reported in a study on *Clostridium ragsdalei* (*Clostridium* strain P11) in a 100-L pilot scale fermentor from switchgrass derived syngas [Kundiyana D K, Huhnke R L, Wilkins M R: Syngas fermentation in a 100-L pilot scale fermentor: Design and process considerations. *J Biosci Bioeng* 2010, 109: 492-498]. However, related studies from the same lab showed that this was due to a contamination in the used syngas since it was passed through a scrubbing mixture containing 20% acetone [Ramachandriya K D: Effect of biomass generated producer gas, methane and physical parameters on producer gas fermentations by *Clostridium* strain P11. Masters thesis, Oklahoma State University 2009; Ramachandriya K D, Wilkins M R, Delorme M J M, Zhu X, Kundiyana D K, Atiyeh H K, Huhnke R L: Reduction of acetone to isopropanol using producer gas fermenting microbes. Biofuels Environ Biotechnol, 2011, epub]. The authors however confirmed acetone to isopropanol reduction by *Clostridium ragsdalei* (*Clostridium* strain P11) and speculated about the presence of a secondary alcohol dehydrogenase but couldn't find any evidence.

It is an object of the invention to overcome one or more of the disadvantages of the prior art, or to at least to provide the public with a useful choice.

SUMMARY OF THE INVENTION

The inventors have identified a novel primary: secondary alcohol dehydrogenase in *C. autoethanogenum* which could be used for the production of isopropanol and/or one or more other products from CO or to upgrade acetone-butanol-ethanol (ABE) fermentation to isopropanol-butanol-ethanol (IBE) fermentation or for the conversion of MEK to 2-butanol, for example, and have optimized the properties of the enzyme, such as substrate and/or co-factor specificity, by directed mutagenesis.

In one aspect of the present invention there is provided an alcohol dehydrogenase having increased specificity for at least one first substrate over at least one second substrate wherein the at least one first substrate and the at least one second substrate are selected from the group consisting of:
the first substrate is acetone and the second substrate is MEK;
the first substrate is acetone and the second substrate is acetaldehyde;
the first substrate is acetone and the second substrate is acetoin;
the first substrate is MEK and the second substrate is acetaldehyde;
the first substrate is MEK and the second is acetoin;
the first substrate is acetoin and the second acetone;
the first substrate is acetoin and the second substrate is MEK;
the first substrate is acetoin and the second substrate is acetaldehyde the first substrate is acetaldehyde and the second acetone; the first substrate is acetaldehyde and the second acetoin; and, the first substrate is acetaldehyde and the second substrate is MEK; and, wherein the alcohol dehydrogenase includes at least one or more mutation compared to the corresponding wild type alcohol dehydrogenase.

In one embodiment, the alcohol dehydrogenase has increased specificity for one, two or three first substrates over two or three second substrates. In another embodiment, the alcohol dehydrogenase has increased specificity for two or three first substrates over one, two or three second substrates.

In another aspect, the invention provides an alcohol dehydrogenase having increased specificity for an NADH co-factor over an NADPH co-factor wherein the alcohol dehydrogenase includes at least one or more mutation compared to the corresponding wild type alcohol dehydrogenase.

In another aspect, the invention provides an alcohol dehydrogenase which uses NADH as a co-factor wherein the alcohol dehydrogenase includes at least one or more mutation compared to the corresponding wild type alcohol dehydrogenase which uses NADPH as a co-factor.

In one particular embodiment, the alcohol dehydrogenase has an increased specificity for acetone over MEK and/or acetaldehyde and/or acetoin.

In one particular embodiment, the alcohol dehydrogenase has an increased specificity for MEK over acetone and/or acetaldehyde and/or acetoin.

In one particular embodiment, the alcohol dehydrogenase has an increased specificity for acetaldehyde over acetone and/or MEK and/or acetoin.

In one particular embodiment, the alcohol dehydrogenase has an increased specificity for acetoin over acetone and/or MEK and/or acetaldehyde.

In one particular embodiment, the alcohol dehydrogenase has substantially no ability to use acetoin as a substrate. In one particular embodiment, the alcohol dehydrogenase has substantially no ability to use acetoin as a substrate, but is able to use acetone, MEK and/or acetalydehyde as a substrate.

In one embodiment, the at least one mutation is an amino acid substitution at one or a combination of the amino acids corresponding to position Gly198, Ser199, Arg200, Pro201 and Tyr218 of the alcohol dehydrogenase sequence of SEQ ID 36.

In one embodiment, the alcohol dehydrogenase includes one or more of the following mutations compared to the corresponding wild type alcohol dehydrogenase: Gly198Asp, Gly198Ile, Gly198Leu, Gly198Val, Ser199Asp, Ser199Glu, Ser199Leu, Ser199Val, Arg200Glu, Pro201Asp, Pro201Glu, Tyr218Ala and Tyr218Phe.

In another embodiment, the alcohol dehydrogenase includes one of the following mutations compared to the corresponding wild type alcohol dehydrogenase: Tyr218Gly, Tyr218Ser or Tyr218Val.

In one embodiment, the alcohol dehydrogenase includes a Ser199Asp substitution. In one embodiment, the alcohol dehydrogenase includes a Ser199Glu substitution.

In one embodiment, the alcohol dehydrogenase includes a combination of the following substitutions Gly198Asp, Ser199Val, Pro201Glu. In one embodiment, the alcohol dehydrogenase includes a combination of the following substitutions, Gly198Asp, Ser199Leu, and Pro201Glu. In another embodiment, the alcohol dehydrogenase includes a combination of the following substitutions: Gly198Asp, Ser199Val, Pro201Glu, and Tyr218Ala. In another embodiment, the alcohol dehydrogenase includes a combination of the following substitutions: Gly198Asp, Ser199Val, Pro201Glu, and Tyr218Phe. In another embodiment, the alcohol dehydrogenase includes a combination of the following substitutions: Gly198Asp, Ser199Val, Pro201Glu, and Tyr218Gly. In another embodiment, the alcohol dehydrogenase includes a combination of the following substitutions: Gly198Asp, Ser199Val, Pro201Glu, and Tyr218Ser. In another embodiment, the alcohol dehydrogenase includes a combination of the following substitutions: Gly198Asp, Ser199Val, Pro201Glu, and Tyr218Val.

In one embodiment, the alcohol dehydrogenase includes a Ser199Asp substitution and has an increased substrate specificity for 1) acetone over MEK and/or acetoin. In one embodiment, the alcohol dehydrogenase includes a Ser199Asp substitution and has an increased substrate specificity for acetone over MEK and acetoin.

In one embodiment, the alcohol dehydrogenase includes a Ser199Glu substitution and has an increased substrate specificity for 1) acetone over MEK, acetaldehyde and/or acetoin; and/or 2) MEK over acetaldehyde and/or acetoin. In one embodiment, the alcohol dehydrogenase includes a Ser199Glu substitution and has an increased substrate specificity for 1) acetone over MEK and acetaldehyde and acetoin. In another embodiment, the alcohol dehydrogenase includes a Ser199Glu substitution and has an increased substrate specificity for MEK over acetaldehyde and acetoin. In one embodiment, the alcohol dehydrogenase includes a Ser199Glu substitution and has an increased substrate specificity for 1) acetone over MEK and acetaldehyde and acetoin; and 2) MEK over acetaldehyde and acetoin.

In another embodiment, the alcohol dehydrogenase includes a combination of the following substitutions Gly198Asp, Ser199Val, and Pro201Glu and has an increased substrate specificity for 1) acetone over MEK; and/or 2) acetaldehyde over MEK, acetone and/or acetoin; and/or, 3) acetoin over acetone and/or MEK. In one embodiment, an alcohol dehydrogenase including this combination of substitutions has an increased substrate specificity for acetaldehyde over MEK and acetone and acetoin. In one embodiment, an alcohol dehydrogenase including this combination of substitutions has an increased substrate specificity for acetoin over acetone and MEK. In another embodiment, an alcohol dehydrogenase including this combination of substitutions has an increased substrate specificity for 1) acetone over MEK; and 2) acetaldehyde over MEK and acetone and acetoin; and 3) acetoin over acetone and MEK.

In another embodiment, the alcohol dehydrogenase includes a combination of the following substitutions Gly198Asp, Ser199Val, Pro201Glu, and Tyr218Ala has an increased substrate specificity for 1) acetone over MEK, acetaldehyde and/or acetoin; and/or 2) MEK over acetaldehyde and/or acetoin; and/or 3) acetoin over acetaldehyde. In one embodiment, an alcohol dehydrogenase including this combination of substitutions has an increased substrate specificity for acetone over MEK and acetaldehyde and acetoin. In one embodiment, an alcohol dehydrogenase including this combination of substitutions has an increased substrate specificity for MEK over acetaldehyde and acetoin. In another embodiment, an alcohol dehydrogenase including this combination of substitutions has an increased substrate specificity for 1) acetone over MEK and acetaldehyde and acetoin; and 2) MEK over acetaldehyde and acetoin; and 3) acetoin over acetaldehyde.

In another embodiment, the alcohol dehydrogenase includes a combination of the following substitutions Gly198Asp, Ser199Val, Pro201Glu, and Tyr218Phe and has an increased substrate specificity for 1) acetone over MEK, acetaldehyde and/or acetoin; and/or MEK over acetaldehyde and/or acetoin; and/or 3) acetalydehyde over acetoin. In one embodiment, an alcohol dehydrogenase including this combination of substitutions has an increased substrate specificity for acetone over MEK and acetaldehyde and acetoin. In one embodiment, an alcohol dehydrogenase including this combination of substitutions has an increased substrate specificity for MEK over acetaldehyde and acetoin. In another embodiment, an alcohol dehydrogenase including this combination of substitutions has an increased substrate specificity for 1) acetone over MEK, acetaldehyde and acetoin; and 2) MEK over acetaldehyde and acetoin; and 3) acetalydehyde over acetoin. In one embodiment, an alcohol dehydrogenase including this combination of substitutions has substantially no ability to use acetoin as a substrate.

In another embodiment, the alcohol dehydrogenase includes a combination of the following substitutions Gly198Asp, Ser199Val, Pro201Glu, and Tyr218Ala and is able to use NADH as a co-factor. In one embodiment, the alcohol dehydrogenase includes all of these substitutions and has an increased substrate specificity for 1) acetone over MEK, acetaldehyde and acetoin; and 2) MEK over acetaldehyde and acetoin; and 3) acetoin over acetaldehyde; and 4) is able to use NADH as a co-factor.

In another embodiment, the alcohol dehydrogenase includes a combination of the following substitutions Gly198Asp, Ser199Val, Pro201Glu, and Tyr218Phe and is able to use NADH as a co-factor. In one embodiment, the alcohol dehydrogenase includes all of these substitutions and has an increased substrate specificity for 1) acetone over MEK, acetaldehyde and acetoin; and 2) MEK over acetaldehyde and acetoin; and 3) acetalydehyde over acetoin; and 5) is able to use NADH as a co-factor.

In one embodiment, the alcohol dehydrogenase has the sequence provided in SEQ ID 38. In one embodiment, the alcohol dehydrogenase has the sequence provided in SEQ ID 42. In one embodiment, the alcohol dehydrogenase has the sequence provided in SEQ ID 50.

In one embodiment, the alcohol dehydrogenase has the sequence provided in SEQ ID 44. In one embodiment, the alcohol dehydrogenase has the sequence provided in SEQ ID 46. In one embodiment, the alcohol dehydrogenase has the sequence provided in SEQ ID 48. In one embodiment, the alcohol dehydrogenase has the sequence provided in SEQ ID 52. In one embodiment, the alcohol dehydrogenase has the sequence provided in SEQ ID 54. In one embodiment, the alcohol dehydrogenase has the sequence provided in SEQ ID 63. In one embodiment, the alcohol dehydrogenase has the sequence provided in SEQ ID 64. In one embodiment, the alcohol dehydrogenase has the sequence provided in SEQ ID 65.

In a second aspect, the invention provides a nucleic acid encoding an alcohol dehydrogenase of the first aspect of the invention.

In certain embodiments, the nucleic acid has the sequence of SEQ ID 37, SEQ ID 41, SEQ ID 47, SEQ ID 49, SEQ ID 67, SEQ ID 68, SEQ ID 69, or SEQ ID 70. In other embodiment, the nucleic acid has the sequence of SEQ ID 39, SEQ ID 43, SEQ ID 45, SEQ ID 51, or SEQ ID 53.

In a third aspect, the invention provides a nucleic acid vector comprising a nucleic acid encoding an alcohol dehydrogenase of the first aspect of the invention. In one embodiment, the vector is an expression vector. In one embodiment the nucleic acid encoding an alcohol dehydrogenase of the first aspect is a nucleic acid of the second aspect.

In a fourth aspect, the invention provides a host cell comprising a nucleic acid of the second or third aspects of the invention.

In a fifth aspect, the invention provides a recombinant microorganism which comprises one or more nucleic acid of the second or third aspects of the invention.

In one embodiment, the microorganism is capable of producing one or more products chosen from:
Isopropanol;
2,3-Butanediol;
Ethanol; and,
2-butanol;
and optionally one or more other products by fermentation.

In one embodiment, the microorganism is capable of producing one or more products chosen from:
Acetoin;
Acetalydehyde;
MEK; and,
Acetone;
and optionally one or more other products by fermentation.

In one embodiment, the recombinant microorganism is chosen from the group of microorganisms comprising bacteria, Archae, and fungi.

In one embodiment, the recombinant microorganism is chosen from the genera *Clostridium, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus, Lactococcus, Enterococcus, Pediococcus, Streptococcus, Saccharomyces, Pichia, Candida Hansenula, Yarrowia, Rhodotorula, Rhizopus, Trichosporon, Lipomyces, Aspergillus, trichoderma, Exophila, Mucor, Cladosporium, Phanerochaete, Cladiophilalophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas, Methylobacter, Methylococcus, Methylomicrobium, Methylosphera, Methylocaldum, Methylocystis, Methylosinus, Methanobacterium, Methanococcus, Methanogenium, Methanosarcina, Methanoshera, Methanothermobacter, Methanotrix, Corynebacterium, Acinetobacter, Actinomyces, Bacteriodes, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella*, and *Psychrobacter*.

In one embodiment the organism is chosen from the group of carboxydotrophic acetogenic microorganisms, the group of ABE microorganisms, the group of Enterobacteria, the group of *Lactobacillus*, the group of fungi and yeasts, the group of aerobic carboxydotrophes, the group of aerobic $CO_2$ fixing organisms, the group of methylotrophes, and the group of methanogens.

In one embodiment, the microorganism is a carboxydotrophic acetogen selected from the group comprising *Clostridium* autoethanogenum, *Clostridium* ljungdahlii, *Clostridium* ragsdalei, *Clostridium* carboxidivorans, *Clostridium* drakei, *Clostridium* scatologenes, *Clostridium* coskatii, *Clostridium* aceticum, *Clostridium* magnum, *Clostridium* sp., *Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter*

*pfennigii*, and *Thermoanaerobacter kiuvi*. In one embodiment the microorganism is *Clostridium autoethanogenum* or *Clostridium ljungdahlii*. In one particular embodiment, the microorganism is *Clostridium autoethanogenum* DSM10061 or DSM23693. In another particular embodiment, the microorganism is *Clostridium ljungdahlii* DSM13528 (or ATCC55383).

In one embodiment, the microorganism is an ABE microorganism selected from the group comprising *Clostridium acetobutylicum*, *Clostridium beijerinckii*, *Clostridium saccharobutylicum*, *Clostridium saccharoperbutylacetonicum*. In one embodiment the microorganism is *Clostridium acetobutylicum* or *Clostridium beijerinckii*. In one particular embodiment, the microorganism is *Clostridium acetobutylicum* ATCC824 (or DSM792). In another particular embodiment, the microorganism is *Clostridium beijerinckii* NCIMB8052 (ATCC51743).

In one embodiment, the microorganism is an Enterobacteria selected from the group comprising *Escherichia, Klebsiella, Zymomonas, Citrobacter, Enterobacter, Salmonella, Serratia*. In one embodiment the microorganism is *Eschericia coli, Zymononas mobilis, Klebsiella pneumonia, Klebsiella oxtoca, Enterobacter cloacae* or *Serratia marcescens*.

In one embodiment, the microorganism is a *Lactobacillus* selected from the group comprising *Lactobacillus, Lactococcus, Enterococcus, Pediococcus, Streptococcus*. In one embodiment the microorganism is *Lactobacillus brevis, Enterococcus faecalis, Lactococcus lactis*.

In one embodiment, the microorganism is a fungi or yeast selected from the group comprising *Saccharomyces, Pichia, Candida Hansenula, Yarrowia, Rhodotorula, Rhizopus, Trichosporon, Lipomyces* and from the group comprising *Aspergillus, Trichoderma, Exophila, Mucor, Cladosporium, Phanerochaete, Cladiophilalophora, Paecilomyces, Scedosporium, Ophistoma*. In one embodiment the microorganism is *Saccharomyces cerevisiae, Candidia tropicalis, Candidia albicans* or *Yarrowia lipolytica*. In one embodiment the microorganism is *Aspargillus niger* or *Trichderma resei*.

In one embodiment, the microorganism is an aerobic carboxydotroph selected from the group comprising *Bacillus, Oligotropha, Pseudomonas, Carbophilus, Hydrogenophaga, Mycobacterium, Zavarzinia*. In one embodiment the microorganism is *Oligotropha carboxydovorans, Carbophilus carboxidus, Hydrogenophaga pseudoflava, Mycobacterium* sp., *Pseudomonas carboxydohydrogena, Pseudomonas* sp., *Zavarzinia compransoris* or *Bacillus schlegelii*.

In one embodiment, the microorganism is an aerobic $CO_2$ fixing organism selected from the group comprising *Cupravidus, Senechocystis, Chloroflexus*. In one embodiment the microorganism is *Cupravidus necator, Senechocystis* sp. or *Chloroflexus auranticus*.

In one embodiment, the microorganism is a methylotroph selected from the group comprising *Methylomonas, Methylobacter, Methylococcus, Methylomicrobium, Methylosphera, Methylocaldum, Methylocystis, Methylosinus*. In one embodiment the microorganism is *Methylococcus capsulatus* or *Methylosinus trichosporium*.

In one embodiment, the microorganism is a methanogen selected from the group comprising *Methanobacterium, Methanococcus, Methanogenium, Methanosarcina, Methanoshera, Methanothermobacter, Methanotrix*. In one embodiment the microorganism is *Methanothermobacter marburgensis* or *Methanosarcina bakeri*.

In a sixth aspect, invention provides a method for the production of one or more of isopropanol, 2,3-Butanediol, ethanol, and 2-butanol, and optionally one or more other products, by microbial fermentation of a substrate using a microorganism of the fifth aspect of the invention.

In another aspect, the invention provides a method for the production of one or more of acetoin, MEK, acetone and acetaldehyde.

In one embodiment the method comprises the steps of:
(a) providing a substrate to a bioreactor containing a culture of one or more microorganism of the invention; and
(b) fermenting the culture in the bioreactor to produce one or more of isopropanol, 2,3-Butanediol, ethanol, and 2-butanol and, optionally, one or more other products.

In one embodiment, the substrate is a substrate comprising one or more of CO, $CO_2$ and $H_2$. In another embodiment, the substrate is a substrate comprising one or more carbohydrate.

In another embodiment, a combination of two or more different substrates may be used. In one embodiment, a combination of a substrate comprising one or more of CO, $CO_2$ and $H_2$ and a substrate comprising one or more carbohydrate is used.

In one embodiment the substrate is a substrate comprising CO and the method comprises the steps of:
(a) capturing CO-containing gas produced as a result of the industrial process, before the gas is released into the atmosphere;
(b) the anaerobic fermentation of the CO-containing gas to produce one or more of isopropanol, 2,3-Butanediol, ethanol, and 2-butanol and optionally one or more other products by a culture containing one or more carboxydotrophic acetogenic microorganism of the invention.

The invention may also be said broadly to consist in the parts, elements and features referred to or indicated in the specification, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIG. 5: shows that Mutant 2 (panel A), Mutant 7 (panel B), Mutant 10 (panel C), Mutant 11 (panel D) and Mutant 13 (panel E) were soluble. Mutant 2 samples (left to right): total cell extract, soluble lysate, column wash fractions (1-6), molecular weight ladder, column elution fractions (1-6). Mutant 7 samples (left to right): total cell extract, soluble lysate, column wash fractions (1-5), molecular weight ladder, column elution fractions (1-7). Mutant 10 samples (left to right): total cell extract, soluble lysate, column wash fraction (1), molecular weight ladder, column wash fractions (2-4), column elution fractions (1-5). Mutant 11 samples (left to right): total cell extract, soluble lysate, column wash fractions (1-3), molecular weight ladder, column elution fractions (1-5). Mutant 13 samples (left to right): total cell extract, soluble lysate, column wash fraction (1), molecular weight ladder, column wash fractions (2-3), column elution fractions (1-5), molecular weight ladder.

FIG. 6: shows the activity of the wild-type protein and Mutants 2, 7, 10, 11 and 13 with NADH as the cofactor and acetone as substrate. Only Mutant 11 has any significant activity using NADH as the cofactor.

BRIEF DESCRIPTION OF SEQUENCE LISTING

Figure 1:
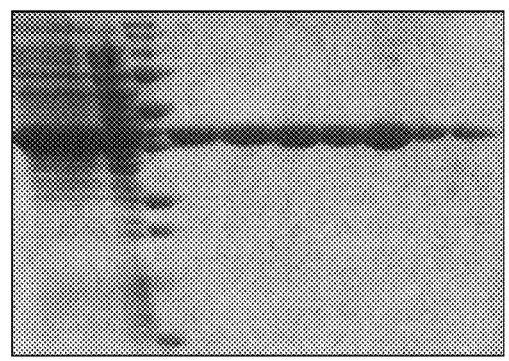
FIG. 1: shows that wild-type protein was highly soluble when expressed in *E. coli*, and could be readily purified. Samples (left to right): total cell extract; soluble lysate; molecular weight ladder; column elution fractions 1-7.

This specification is accompanied by a sequence listing in which the following sequences are listed:

SEQ ID No.s 1 to 34: are described in Tables 3, 4 and 5 herein after.

SEQ ID No. 35: nucleic acid sequence of a wild type ADH studied by the inventors.

SEQ ID No. 36: amino acid sequence of a wild type ADH studied by the inventors.

SEQ ID No. 37: nucleic acid sequence of a mutant ADH comprising the substitution Ser199Asp generated by the inventors.

SEQ ID No. 38: amino acid sequence of a mutant ADH comprising the substitution Ser199Asp generated by the inventors.

SEQ ID No. 39: nucleic acid sequence of the Wood Ljungdahl promoter region.

SEQ ID No. 40: nucleotide sequence of plasmid pMTL85147-ThlA-CtfAB-Adc-Adh described further herein.

SEQ ID No. 41: nucleic acid sequence of mutant 7 described further herein after (codon optimised).

SEQ ID No. 42: amino acid sequence of mutant 7 described further herein after.

SEQ ID No. 43: nucleic acid sequence of mutant 8 described further herein after (codon optimised).

SEQ ID No. 44: amino acid sequence of mutant 8 described further herein after.

SEQ ID No. 45: nucleic acid sequence of mutant 9 described further herein after (codon optimised).

SEQ ID No. 46: amino acid sequence of mutant 9 described further herein after.

SEQ ID No. 47: nucleic acid sequence of mutant 10 described further herein after (codon optimised).

SEQ ID No. 48: amino acid sequence of mutant 10 described further herein after.

SEQ ID No. 49: nucleic acid sequence of mutant 11 described further herein after (codon optimised).

SEQ ID No. 50: amino acid sequence of mutant 11 described further herein after.

SEQ ID No. 51: nucleic acid sequence of mutant 12 described further herein after (codon optimised).

SEQ ID No. 52: amino acid sequence of mutant 12 described further herein after.

SEQ ID No. 53: nucleic acid sequence of mutant 13 described further herein after (codon optimised).

SEQ ID No. 54: amino acid sequence of mutant 13 described further herein after.

SEQ ID No. 55: nucleotide sequence of 5' homology arm of *C. autoethanogenum* alcohol dehydrogenase gene.

SEQ ID No. 56: nucleotide sequence of 3' homology arm of *C. autoethanogenum* alcohol dehydrogenase gene.

SEQ ID No. 57: primer Sec5f.
SEQ ID No. 58: primer Sec5r.
SEQ ID No. 59: primer Sec3f.
SEQ ID No. 60: primer Sec3r.
SEQ ID No. 61: primer SecOf.
SEQ ID No. 62: primer SecOr.

SEQ ID No. 63: Amino acid sequence of alcohol dehydrogenase enzyme with the following substitutions Gly198Asp, Ser199Val, Pro201Glu, and Tyr218Gly SEQ ID No. 64: Amino acid sequence of alcohol dehydrogenase enzyme with the following substitutions Gly198Asp, Ser199Val, Pro201Glu, and Tyr218Ser SEQ ID No. 65: Amino acid sequence of alcohol dehydrogenase enzyme with the following substitutions Gly198Asp, Ser199Val, Pro201Glu, and Tyr218Val SEQ ID No. 66: Amino acid sequence of alcohol dehydrogenase enzyme with the following substitutions Ser199Glu SEQ ID No. 67: Nucleic acid sequence of alcohol dehydrogenase enzyme with the following substitutions Gly198Asp, Ser199Val, Pro201Glu, and Tyr218Gly SEQ ID No. 68: Nucleic acid sequence of alcohol dehydrogenase enzyme with the following substitutions Gly198Asp, Ser199Val, Pro201Glu, and Tyr218Ser SEQ ID No. 69: Nucleic acid sequence of alcohol dehydrogenase enzyme with the following substitutions Gly198Asp, Ser199Val, Pro201Glu, and Tyr218Val SEQ ID No. 70: Nucleic acid sequence of alcohol dehydrogenase enzyme with the following substitutions Ser199Glu (codon optimised).

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The inventor(s) have unexpectedly found that mutation of an alcohol dehydrogenase enzyme from a carboxydotrophic acetogenic microorganism increases its specificity for one or more of the substrates acetoin, methyl ethyl ketone (MEK or 2-butanone), acetone and acetalydehyde relative to one another.

In addition, the inventors have identified mutants that are able to accept NADH as a co-factor instead of or in addition to NADPH. Thus it is not limited by the availability of only one of these co-factors and is able to use the more abundant intracellular NADH pool for increasing the overall efficiency of production formation.

The mutation(s) mean that enzymes of the invention are adapted to preferentially produce one fermentation end product over another and allow one to utilize the typically much bigger NADH pool over the NADPH pool (Bennett & San, 2009). In ABE fermentation, both ethanol and acetone are produced and in IBE fermentation isopropanol is produced (Köpke & Dürre, 2011). The invention may allow one to increase the reduction of acetone to isopropanol or preferentially catalyse this reaction over acetaldehyde to ethanol or vice versa. For example, the invention may help to overcome limitations in isopropanol production, as all strains rely on an unmodified alcohol dehydrogenase that is strictly NADPH dependent and has a high background activity towards acetaldehyde. *E. coli* strains engineered for isopropanol production suffer the same shortcomings and low yields as the same NADPH dependent alcohol dehydrogenase enzyme from *C. beijerinckii* is used without alternatives [Hanai T et al (2007) Engineered synthetic pathway for isopropanol production in *Escherichia coli*. *Applied and environmental microbiology* 73:7814-8; Inokuma K et al (2010) Improvement of isopropanol production by metabolically engineered *Escherichia coli* using gas stripping. *Journal of bioscience and bioengineering* 110: 696-701; Jojima T et al (2008) Production of isopropanol by metabolically engineered *Escherichia coli*. *Applied microbiology and biotechnology* 77:1219-24]. Similarly, the invention provides a means for the production of isopropanol from substrates comprising carbon monoxide by carboxydotrophic acetogenic microorganisms previously not able to produce viable levels of isopropanol. Some carboxydotrophic organisms as *C. autoethanogenum*, *C. ljungdahlii* or *C. ragsdalei* are able to form both ethanol and 2,3-butanediol (Köpke et al., 2011). The invention may also allow one to increase the reduction of acetoin to 2,3-butanediol or preferentially catalyse this reaction over acetaldehyde to ethanol or vice versa. 2,3-butanediol can be converted to MEK by a diol dehydratase (Toraya et al, 1976, Substrate specificity of coenzyme B12-dependent diol dehydrase-glycerol as both a good substrate and a potent inactivator. *Biochem. Biophys. Res. Commun.,* 69: 475-80). The invention allows effective conversion of MEK into 2-butanol. Accordingly, the invention also provides a solution for producing 2,3-butanediol from acetoin and 2-butanol from MEK with higher specificity.

Accordingly, the invention provides, inter alia, alcohol dehydrogenases having an increased specificity for an acetone substrate over other substrates like acetoin, methyl ethyl ketone (MEK or 2-butanone) and/or an acetaldehyde substrate, an MEK substrate over an acetaldehyde and/or acetoin substrate, an acetaldehyde substrate over an MEK, acetoin and/or acetone substrate, and/or an acetoin substrate over an acetone, MEK and/or acetaldehyde substrate wherein the alcohol dehydrogenase includes at least one or more mutation compared to the corresponding wild type alcohol dehydrogenase, nucleic acids encoding the alcohol dehydrogenases, nucleic acid vectors comprising the nucleic acids, microorganisms which are capable of producing one or more of isopropanol, 2,3-butanediol, ethanol and 2-butanol, and optionally one or more other products, by fermentation of a substrate and which comprise one or more nucleic acid encoding one or more alcohol dehydrogenase of the invention, and methods for the production of one or more of isopropanol, 2,3-butanediol, ethanol and 2-butanol, and optionally one or more other products.

The invention also provides an alcohol dehydrogenase that has substantially no ability to use acetoin as a substrate, nucleic acids and nucleic acid vectors encoding such an alcohol dehydrogenase, microorganisms comprising said nucleic acids or nucleic acid vectors and methods of use of such alcohol dehydrogenase.

The phrase "substrate comprising one or more of CO, $CO_2$ and $H_2$" should be understood to include any substrate in which one or more of CO, $CO_2$ and $H_2$ is available to one or more strains of microorganisms for growth and/or fermentation, for example. It should be appreciated that the substrate may comprise 100% CO, $CO_2$ or $H_2$ or a majority of CO, $CO_2$ or $H_2$ compared to the other gases, or may be combined in any ratio of two or more of the gases. In particular embodiments, the substrate comprises a combination of CO and $CO_2$. In another embodiment the substrate comprises a combination of CO and $H_2$. In another embodiment, the substrate comprises a combination of $CO_2$ and $H_2$. In another embodiment, the substrate comprises a combination of CO, $CO_2$ and $H_2$.

In certain embodiments, the substrate may comprise $CO_2$ and any culture, growth or fermentation performed in the presence of light (photosynthesis) and/or electricity (electrosynthesis). In certain embodiments, the $CO_2$ is combined with $O_2$.

In one embodiment, the "substrate comprising CO, $CO_2$ and $H_2$" is a "substrate comprising carbon monoxide". A "substrate comprising CO" and like terms should be understood to include any substrate in which carbon monoxide is available to one or more strains of microorganisms for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate comprising CO to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

In one embodiment, the "substrate comprising CO, $CO_2$ and $H_2$" is a "substrate comprising $CO_2$ and $H_2$". A "substrate comprising $CO_2$ and $H_2$" and like terms should be understood to include any substrate in which carbon dioxide and hydrogen is available to one or more strains of microorganisms for growth and/or fermentation, for example.

The $CO_2$ and $H_2$ containing substrate will typically contain a major proportion of $H_2$, such as at least about 30% $H_2$ by volume, or at least 40% $H_2$ by volume, or at least 50% $H_2$ by volume, or at least 60% $H_2$ by volume, or at least 70% $H_2$ by volume, or at least 80% $H_2$ by volume, or at least 85% $H_2$ by volume.

The gaseous substrate will typically contain at least about 10% $CO_2$ by volume, or at least 15% $CO_2$ by volume, or at least 20% $CO_2$ by volume, or at least 25% $CO_2$ by volume, or at least 30% $CO_2$ by volume, or at least 40% $CO_2$ by volume.

In certain embodiments, the ratio of H2:$CO_2$ is around 1:1, or around 2:1, or around 3:1.

In certain embodiments the substrate comprising $CO_2$ and $H_2$ is a waste gas obtained as a by-product of an industrial process, or from some other source. The largest source of $CO_2$ emissions globally is from the combustion of fossil fuels such as coal, oil and gas in power plants, industrial facilities and other sources.

The gaseous substrate may be a $CO_2$ and $H_2$-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in $H_2$ or rich in $CO_2$ are more abundant that waste gas streams rich in both $H_2$ and $CO_2$. A skilled person would understand that blending one or more gas streams comprising one of the desired components of $CO_2$ and $H_2$ would fall within the scope of the present invention.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate.

In the description which follows, embodiments of the invention are described in terms of delivering and fermenting a "gaseous substrate containing CO" or a "gaseous substrate comprising one or more of CO, $CO_2$ and $H_2$". However, it should be appreciated that the gaseous substrate may be provided in alternative forms. For example, the gaseous substrate may be provided dissolved in a liquid. Essentially, a liquid is saturated with a carbon monoxide, carbon dioxide and/or hydrogen containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO", "substrate comprising $CO_2$ and $H_2$) and "substrate comprising one or more of CO, $CO_2$ and $H_2$" and like phrases.

The phrase "substrate comprising one or more carbohydrates" and like terms should be understood to include any substrate in which one or more carbohydrate is available to one or more strains of microorganisms for growth and/or fermentation, for example. "Carbohydrates" should be taken broadly to include mono-, di-, oligo- and poly-saccharides, simple and complex carbohydrates, including glucose, fructose, molasses and starch.

In one embodiment, the "substrate comprising one or more carbohydrates" may be sourced from biomass. The biomass may be of any nature and includes, for example, residues from forests or other commercial crops (such as trees, branches, stumps, wood chips, saw dust, clippings), municipal solid waste, and crops grown to provide a feedstock for the production of one or more products by microbial fermentation, including, for example, miscanthus, switchgrass, hemp, corn, poplar, willow, sorghum, sugarcane, and bamboo.

Unless the context requires otherwise, the phrases "fermenting", "fermentation process" or "fermentation reaction" and the like, as used herein, are intended to encompass both the growth phase and product biosynthesis phase of the process. As will be described further herein, in some embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact. In some embodiments the bioreactor may comprise a first growth reactor and a second fermentation reactor. As such, when referring to the addition of substrate to the bioreactor or fermentation reaction it should be understood to include addition to either or both of these reactors where appropriate.

The terms nucleic acid "constructs" or "vectors" and like terms should be taken broadly to include any nucleic acid (including DNA, cDNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker. In one particular embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained). The vectors may be used for cloning or expression of nucleic acids and for transformation of microorganisms to produce recombinant microorganisms. The vectors may include one or more nucleic acids encoding one or more alcohol dehydrogenase enzyme of the invention.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of microorganisms which differ from the organism to which they are to be introduced, or they may be created artificially or by recombination. In another embodiment, the exogenous nucleic acids represent nucleic acid sequences not naturally present within the microorganism to which they are to be introduced and allow for the expression of a product not naturally present within the microorganism. The exogenous nucleic acid may be adapted to integrate into the genome of the microorganism to which it is to be introduced or to remain in an extra-chromosomal state.

A "parental microorganism" is a microorganism used to generate a microorganism of the invention. The parental microorganism may be one that occurs in nature (ie a wild type microorganism) or one that has been previously modified but which does not express or over-express one or more of the enzymes the subject of the present invention. Accordingly, the microorganisms of the invention have been modified to express one or more alcohol dehydrogenase of the invention in the parental microorganism.

The alcohol dehydrogenase enzymes of the invention are referred to herein to have "increased specificity" for one substrate over another. This is intended to mean that the alcohol dehydrogenase has increased specificity for one substrate relative to another, compared to the wild type alcohol dehydrogenase. It should not be taken to necessarily infer that an alcohol dehydrogenase of the invention has a higher specificity for a particular substrate compared to the wild type alcohol dehydrodenase, although this may be the case in some embodiments. Additionally, the term should not be taken to mean that an alcohol dehydrogenase of the invention has absolute specificity for a particular substrate over another, although this may be the case in some embodiments, and includes at least a preference for a particular substrate over another substrate.

"Increased specificity", "higher specificity" or like terms, when used in relation to an NADH or NADPH co-factor, refers to the degree of affinity with which a co-factor binds to an alcohol dehydrogenase during a reaction. It should not be taken to mean that an alcohol dehydrogenase and a co-factor have absolute specificity, although this may be the case, and includes at least a preference for the binding between a particular alcohol dehydrogenase and one co-factor over another co-factor.

Reference is made herein to production of "one or more products including isopropanol, 2,3-butanediol, ethanol and 2-butanol". However, it should be appreciated that additional products may also be generated.

Reference may also be made herein to production of "one or more products including acetoin, MEK, acetaldehyde and acetone". While these products are also referred to herein as "substrates", in certain embodiments, where the specificity of a mutant alcohol dehydrogenase of the invention is reduced for a particular substrate compared to another, it will be converted to downstream products at a reduced level, or substantially no conversion will occur, allowing increased levels of acetoin, MEK, acetaldehyde and/or acetone to accumulate. By way of example, in one embodiment an alcohol dehydrogenase of the invention has substantially no ability to use acetoin as a substrate and so acetoin may accumulate.

In addition, in some embodiments, it should be appreciated that one or more of the products referred to herein, including one or more of isopropanol, 2,3-butanediol, ethanol and 2-butanol, may be used as intermediates or precursors which are further converted into downstream products, in the same fermentation reaction, a separate fermentation reaction, or by chemical synthesis. In this case, one may not be able to detect the production of one or more of the products in a particular microorganism or may only be able to detect small levels of production. However, the production of the one or more products may be inferred based on the production of one or more downstream product.

In certain embodiments of the invention, an alcohol dehydrogenase of the invention has "substantially no ability to use acetoin as a substrate". This does not necessarily imply that the enzyme has absolutely no ability to use acetoin as a substrate, although this may be preferred. In one embodiment, the phrase should be taken to include a tolerance of approximately 1% or less of the activity of a wild type enzyme or an enzyme efficiency of kcat/$K_M$ of less than 0.1 sec$^{-1}$ M$^{-1}$.

The Enzyme

While the inventors have demonstrated that mutation of an alcohol dehydrogenase (SEQ ID 36) from *C. autoethanogenum* increases specificity for various substrates compared to other substrates, and in certain embodiments that co-factor specificity may be altered or optimised, they contemplate that the invention is widely applicable to other alcohol dehydrogenase enzymes from other organisms; in particular, any alcohol dehydrogenase which has activity towards primary or secondary alcohols and uses NADH or NADPH as substrate (EC 1.1.1.1 or EC 1.1.1.2).

Typically, the group of alcohol dehydrogenases to which the invention is applicable will have at least approximately 65% sequence identity to the alcohol dehydrogenase of SEQ ID 36, more particularly at least approximately 70%, 75%, 80%, 85%, 90%, 95%, or 99% sequence identity.

By way of example, the invention may be applied to the following alcohol dehydrogenases: primary: secondary alcohol deheydrogenase of *C. autoethanogenum* (SEQ ID No 36), primary: secondary alcohol deheydrogenase of *C. ljungdahlii* (YP_003780646.1), primary: secondary alcohol deheydrogenase of *C. beijerinckii* (P25984.2), primary: secondary alcohol deheydrogenase of *Thermoanaerobacter ethanolicus* (ABC50090.1), or primary: secondary alcohol deheydrogenase of *Thermoanaerobium brockii* (P14941.1).

An alcohol dehydrogenase of the invention comprises at least one mutation compared to the corresponding wild type alcohol dehydrogenase. In one embodiment, the at least one mutation is an amino acid substitution at one or a combination of the amino acids corresponding to position Gly198, Ser199, Arg200, Pro201 and Tyr218 of the alcohol dehydrogenase sequence of SEQ ID 36. In one embodiment, the alcohol dehydrogenase comprises at least one mutation wherein the at least one mutation is an amino acid substitution at the position corresponding to position Ser199 of the alcohol dehydrogenase sequence of SEQ ID 36. Skilled persons will readily appreciate the relevant position (corresponding to position 198, 199, 201 and 218 of the ADH of SEQ ID 36) in alternative alcohol dehydrogenases by aligning the sequence with that of the alcohol dehydrogenase of SEQ ID 36 according to standard procedures known in the art.

In one embodiment, the alcohol dehydrogenase includes one or more of the following mutations compared to the corresponding wild type alcohol dehydrogenase: Gly198Asp, Gly198Ile, Gly198Leu, Gly198Val, Ser199Asp, Ser199Glu, Ser199Leu, Ser199Val, Arg200Glu, Pro201Asp, Pro201Glu, Tyr218Ala and Tyr218Phe.

The inventors also envisage alcohol dehydrogenases of the invention including one of the following mutations compared to the corresponding wild type alcohol dehydrogenase: Tyr218Gly, Tyr218Ser and Tyr218Val. These mutations represent substitutions which are all close in size to the Tyr218Ala and Tyr218Phe substitutions exemplified in the examples section herein after.

In one embodiment, the alcohol dehydrogenase includes a Ser199Asp substitution. In one embodiment, the alcohol dehydrogenase includes a Ser199Glu substitution.

In one embodiment, the alcohol dehydrogenase includes a combination of the following substitutions Gly198Asp, Ser199Val, Pro201Glu. In one embodiment, the alcohol dehydrogenase includes a combination of the following substitutions, Gly198Asp, Ser199Leu, and Pro201Glu. In another embodiment, the alcohol dehydrogenase includes a combination of the following substitutions: Gly198Asp, Ser199Val, Pro201Glu, and Tyr218Ala. In another embodiment, the alcohol dehydrogenase includes a combination of the following substitutions: Gly198Asp, Ser199Val, Pro201Glu, and Tyr218Phe. In another embodiment, the alcohol dehydrogenase includes a combination of the following substitutions: Gly198Asp, Ser199Val, Pro201Glu, and Tyr218Gly. In another embodiment, the alcohol dehydrogenase includes a combination of the following substitutions: Gly198Asp, Ser199Val, Pro201Glu, and Tyr218Ser. In another embodiment, the alcohol dehydrogenase includes a combination of the following substitutions: Gly198Asp, Ser199Val, Pro201Glu, and Tyr218Val.

In one embodiment, the alcohol dehydrogenase includes a Ser199Asp substitution and has an increased substrate specificity for acetone over MEK and/or acetoin. In one embodiment, the alcohol dehydrogenase includes a Ser199Asp substitution and has an increased substrate specificity for acetone over MEK and acetoin.

In one embodiment, the alcohol dehydrogenase includes a Ser199Glu substitution and has an increased substrate specificity for 1) acetone over MEK, acetaldehyde and/or acetoin; and/or 2) MEK over acetaldehyde and/or acetoin. In one embodiment, the alcohol dehydrogenase includes a Ser199Glu substitution and has an increased substrate specificity for 1) acetone over MEK and acetaldehyde and acetoin. In another embodiment, the alcohol dehydrogenase includes a Ser199Glu substitution and has an increased substrate specificity for MEK over acetaldehyde and acetoin. In one embodiment, the alcohol dehydrogenase includes a Ser199Glu substitution and has an increased substrate specificity for 1) acetone over MEK and acetaldehyde and acetoin; and 2) MEK over acetaldehyde and acetoin.

In another embodiment, the alcohol dehydrogenase includes a combination of the following substitutions Gly198Asp, Ser199Val, and Pro201Glu and has an increased substrate specificity for 1) acetone over MEK; and/or 2) acetaldehyde over MEK, acetone and/or acetoin; and/or, 3) acetoin over acetone and/or MEK. In one embodiment, an alcohol dehydrogenase including this combination of substitutions has an increased substrate specificity for acetaldehyde over MEK and acetone and acetoin. In one embodiment, an alcohol dehydrogenase including this combination of substitutions has an increased substrate specificity for acetoin over acetone and MEK. In another embodiment, an alcohol dehydrogenase including this combination of substitutions has an increased substrate specificity for 1) acetone over MEK; and 2) acetaldehyde over MEK and acetone and acetoin; and 3) acetoin over acetone and MEK.

In another embodiment, the alcohol dehydrogenase includes a combination of the following substitutions Gly198Asp, Ser199Val, Pro201Glu, and Tyr218Ala has an increased substrate specificity for 1) acetone over MEK, acetaldehyde and/or acetoin; and/or 2) MEK over acetaldehyde and/or acetoin; and/or 3) acetoin over acetaldehyde. In one embodiment, an alcohol dehydrogenase including this combination of substitutions has an increased substrate specificity for acetone over MEK and acetaldehyde and acetoin. In one embodiment, an alcohol dehydrogenase including this combination of substitutions has an increased substrate specificity for MEK over acetaldehyde and acetoin. In another embodiment, an alcohol dehydrogenase including this combination of substitutions has an increased substrate specificity for 1) acetone over MEK and acetaldehyde and acetoin; and 2) MEK over acetaldehyde and acetoin; and 3) acetoin over acetaldehyde.

In another embodiment, the alcohol dehydrogenase includes a combination of the following substitutions Gly198Asp, Ser199Val, Pro201Glu, and Tyr218Phe and has an increased substrate specificity for 1) acetone over MEK, acetaldehyde and/or acetoin; and/or MEK over acetaldehyde and/or acetoin; and/or 3) acetalydehyde over acetoin. In one embodiment, an alcohol dehydrogenase including this combination of substitutions has an increased substrate specificity for acetone over MEK and acetaldehyde and acetoin. In one embodiment, an alcohol dehydrogenase including this combination of substitutions has an increased substrate specificity for MEK over acetaldehyde and acetoin. In another embodiment, an alcohol dehydrogenase including this combination of substitutions has an increased substrate specificity for 1) acetone over MEK, acetaldehyde and acetoin; and 2) MEK over acetaldehyde and acetoin; and 3) acetalydehyde over acetoin. In one embodiment, an alcohol dehydrogenase including this combination of substitutions has substantially no ability to use acetoin as a substrate.

In another embodiment, the alcohol dehydrogenase includes a combination of the following substitutions Gly198Asp, Ser199Val, Pro201Glu, and Tyr218Ala and is able to use NADH as a co-factor. In one embodiment, the alcohol dehydrogenase includes all of these substitutions and has an increased substrate specificity for 1) acetone over MEK, acetaldehyde and acetoin; and 2) MEK over acetaldehyde and acetoin; and 3) acetoin over acetaldehyde; and 4) is able to use NADH as a co-factor.

In another embodiment, the alcohol dehydrogenase includes a combination of the following substitutions Gly198Asp, Ser199Val, Pro201Glu, and Tyr218Phe and is able to use NADH as a co-factor. In one embodiment, the alcohol dehydrogenase includes all of these substitutions and has an increased substrate specificity for 1) acetone over MEK, acetaldehyde and acetoin; and 2) MEK over acetaldehyde and acetoin; and 3) acetalydehyde over acetoin; and 5) is able to use NADH as a co-factor.

In one embodiment, the alcohol dehydrogenase has the sequence provided in SEQ ID 38. In one embodiment, the alcohol dehydrogenase has the sequence provided in SEQ ID 42. In one embodiment, the alcohol dehydrogenase has the sequence provided in SEQ ID 50.

In one embodiment, the alcohol dehydrogenase has the sequence provided in SEQ ID 44. In one embodiment, the alcohol dehydrogenase has the sequence provided in SEQ ID 46. In one embodiment, the alcohol dehydrogenase has the sequence provided in SEQ ID 48. In one embodiment, the alcohol dehydrogenase has the sequence provided in SEQ ID 52. In one embodiment, the alcohol dehydrogenase has the sequence provided in SEQ ID 54. In one embodiment, the alcohol dehydrogenase has the sequence provided in SEQ ID 63. In one embodiment, the alcohol dehydrogenase has the sequence provided in SEQ ID 64. In one embodiment, the alcohol dehydrogenase has the sequence provided in SEQ ID 65.

The alcohol dehydrogenases of the invention may be made by any appropriate means known in the art including, for example, site directed mutagenesis techniques, random mutagenesis techniques, recombinant methodology and chemical synthesis, as described herein after.

In some cases, mutant alcohol dehydrogenases of the invention may be naturally insoluble. These enzymes may be made soluble using standard techniques. By way of example, techniques involving, co-expression of one or more chaperones, may be used. In one particular embodiment, co-expression of the GroEL and/or GroES chaperones is employed. In one particular embodiment, use of the plasmid pGro7 (Takara Bio, Inc; clontech.com/takara/NZ/Products/Protein_Research/Protein_Folding_and_Expression/Chaperone_Plasmid_Set) may be used. This plasmid facilitates arabinose-inducible expression of the GroEL/ES chaperone proteins. Exemplary techniques are also provided in Example 2 herein after.

One may assess whether an alcohol dehyrogenase of the invention has the appropriate functionality using any number of known methods. However, by way of example, the methods outlined in the Examples herein after may be used. Alternatively, the methods outlined in Ismail et al. [Purification and characterization of a primary-secondary alcohol dehydrogenase from two strains of *Clostridium beijerinckii*. J Bacteriol 1993, 175: 5097-5105], or Khorkin et al [NADP-dependent bacterial alcohol dehydrogenases: crystal structure, cofactor-binding and cofactor specificity of the ADHs of *Clostridium beijerinckii* and *Thermoanaerobacter brockii*. J Mol. Biol. 1998, 22: 278(5): 967-981] may be used to assess enzyme activity.

Co-factor specificity may be assessed using standard methodology. However, by way of example the methods described in the "Examples" section herein after may be used.

Nucleic Acids

In so far as the invention relates to novel alcohol dehydrogenases, it also provides nucleic acids encoding the alcohol dehydrogenases and nucleic acid vectors comprising such nucleic acids.

Skilled persons will readily appreciate the sequence of a nucleic acid encoding an alcohol dehydrogeanse of the invention, having regard to the amino acid sequence of the enzyme and the degeneracy in the genetic code. However, by way of example only, in one embodiment, the nucleic acid has the sequence of SEQ ID 37. In other embodiment, the nucleic acid has the sequence of SEQ ID 41 or SEQ ID 49. In yet other embodiments, the nucleic acid has the sequence of SEQ ID 39, SEQ ID 43, SEQ ID 45, SEQ ID 47, SEQ ID 51, SEQ ID 53, SEQ ID 67, SEQ ID 68, SEQ ID 69 or SEQ ID 70.

It should be appreciated that the nucleic acids encoding an alcohol dehydrogenase of the invention may be codon optimised for any particular microorganism.

To the extent that nucleic acids, alcohol dehydrogenases and microorganisms of the invention may be made and used using recombinant technology, the invention also provides nucleic acid vectors comprising one or more nucleic acid encoding one or more alcohol dehydrogenase of the invention.

The nucleic acids of the invention may remain extra-chromosomal upon transformation of a microorganism or may be adapted for integration into the genome of the microorganism. Accordingly, nucleic acids of the invention may include additional nucleotide sequences adapted to assist integration (for example, a region which allows for homologous recombination and targeted integration into the host genome) or stable expression and replication of an extrachromosomal construct (for example, origin of replication, promoter and other regulatory sequences).

In one embodiment, the nucleic acids encoding one or more alcohol dehydrogenase of the invention will comprise a promoter adapted to promote expression of the one or more enzymes encoded by the nucleic acids. In one embodiment, the promoter is a constitutive promoter that is preferably highly active under appropriate fermentation conditions. Inducible promoters could also be used. In preferred embodiments, the promoter is selected from the group comprising Wood-Ljungdahl gene cluster or an arabinose inducible pBAD promoter. It will be appreciated by those of skill in the art that other promoters which can direct expression, preferably a high level of expression under appropriate fermentation conditions, would be effective as alternatives to the exemplified embodiments.

Nucleic acids and nucleic acid constructs, including expression constructs/vectors of the invention may be constructed using any number of techniques standard in the art. For example, chemical synthesis, site directed mutagenesis, or recombinant techniques may be used. Such techniques are described, for example, in Sambrook et al (Molecular Cloning: A laboratory manual, Cold Spring Harbor Laboratory Press, Cold Spring Harbor, N.Y., 1989). Further exemplary techniques are described in the Examples section herein after. Essentially, the individual genes and regulatory elements will be operably linked to one another such that the genes can be expressed to form the desired proteins. Suitable vectors for use in the invention will be appreciated by those of ordinary skill in the art. However, by way of example, the following vectors may be suitable: pBAD or pMTL80000 vectors, and the plasmids exemplified in the Examples section herein after.

The invention also provides host organisms, particularly microorganisms, and including viruses, bacteria, and yeast, comprising any one or more of the nucleic acids described herein.

Microorganisms

The invention also provides microorganisms which are capable of producing one or more of isopropanol, MEK, 2,3-butanediol and 2-butanol and optionally one or more other products, by fermentation of a substrate and which comprise at least one nucleic acid of the invention.

The microorganisms of the invention may be prepared from a parental microorganism using any number of techniques known in the art, including, for example, site directed mutagenesis techniques to introduce the desired mutation(s) into an alcohol dehydrogenase gene native to a parental microorganism, or other recombinant technologies to introduce one or more nucleic acid encoding one or more alcohol dehydrogeanse of the invention into a parental microorganism.

In one embodiment, one or more exogenous nucleic acid encoding one or more alcohol dehydrogeanse is introduced into a parental microorganism and replaces one or more alcohol dehydrogenase gene native to the parental microorganism. In another embodiment, one or more exogenous nucleic acid encoding one or more alcohol dehydrogeanse of the invention is introduced to a parental microorganism and is supplementary to an alcohol dehydrogenase gene native to the parental microorganism. In other embodiments, one or more exogenous nucleic acid is introduced into a parental microorganism to introduce one or more desired mutation into one or more alcohol dehydrogenase gene native to the parental microorganism. In another embodiment, one or more exogenous nucleic acid encoding one or more alcohol dehydrogeanse is introduced into a parental microorganism, and one or more mutation is introduced to one or more alcohol dehydrogenase gene native to the parental microorganism to reduce or knock out its expression and activity.

In one embodiment, a microorganism of the invention is prepared from a parental microorganism using recombinant technology. For example, a parental microorganism is transformed with one or more exogenous nucleic acid encoding an alcohol dehydrogeanse of the invention, or one or more nucleic acid adapted to introduce a desired mutation to a native alcohol dehydrogenase gene in the parental microorganism. An exogenous nucleic acid may remain extrachromosomal upon transformation of the parent microorganism or may integrate into the genome of the parent microorganism (in one embodiment to replace a native alcohol dehydrogenase gene, or introduce a mutation into a native alcohol dehyrogenase gene). Accordingly, they may include additional nucleotide sequences adapted to assist integration (for example, a region which allows for homologous recombination and targeted integration into the host genome) or expression and replication of an extrachromosomal construct (for example, origin of replication, promoter and other regulatory elements or sequences), as described herein before.

By way of example only, transformation (including transduction or transfection) of a microorganism may be achieved by electroporation, ultrasonication, polyethylene glycol-mediated transformation, chemical or natural competence, or conjugation. Suitable transformation techniques are described for example in, Sambrook J, Fritsch E F, Maniatis T: Molecular Cloning: A laboratory Manual, Cold Spring Harbour Laboratory Press, Cold Spring Harbour, 1989.

One or more exogenous nucleic acids may be delivered to a parental microorganism as naked nucleic acids or may be formulated with one or more agents to facilitate the transformation process (for example, liposome-conjugated nucleic acid, an organism in which the nucleic acid is contained). The one or more nucleic acids may be DNA, RNA, or combinations thereof, as is appropriate. Restriction inhibitors may be used in certain embodiments; see, for example Murray, N. E. et al. (2000) *Microbial. Molec. Biol. Rev.* 64, 412.)

In one embodiment, the parental microorganism is a bacteria, Archae, and fungi.

In one embodiment, the parental microorganism is chosen from genera *Clostridium*, Acetobacterium, Moorella, Butyribacterium, Blautia, Oxobacter, Thermoanaerobacter, Escherichia, Klebsiella, Zymomonas, Citrobacter, Enterobacter, Salmonella, Serratia, Lactobacillus, Lactococcus, Enterococcus, Pediococcus, Streptococcus, Saccharomyces, Pichia, Candida Hansenula, Yarrowia, Rhodotorula, Rhizopus, Trichosporon, Lipomyces, Aspergillus, trichoderma, Exophila, Mucor, Cladosporium, Phanerochaete, Cladiophilalophora, Paecilomyces, Scedosporium, Ophistoma, Bacillus, Oligotropha, Pseudomonas, Carbophilus, Hydrogenophaga, Mycobacterium, Zavarzinia, Cupravidus, Senechocystis, Chloroflexus, Methylomonas, Methylobacter, Methylococcus, Methylomicrobium, Methylosphera, Methylocaldum, Methylocystis, Methylosinus, *Methanobacterium, Methanococcus, Methanogenium, Methanosarcina, Methanoshera, Methanothermobacter, Methanotrix, Corynebacterium, Acinetobacter, Actinomyces, Bacteriodes, Burkholderia, Brevibacterium, Pyrococcus, Geobacter, Geobacillus, Paenibacillus, Mycobacterium, Rhodopseudomonas, Thermatoga, Thermoanaerobacter, Streptomyces, Rhodobacter, Rhodococcus, Peptococcus, Bifidobacterium, Propionibacterium, Fusobacterium, Campylobacter, Veillonella, Aquincola, Arthrobacter, Moraxella*, and *Psychrobacter*.

In one embodiment the parental microorganism is chosen from the group of carboxydotrophic acetogenic microorganisms, the group of ABE microorganisms, the group of Enterobacteria, the group of *Lactobacillus*, the group of fungi and yeasts, the group of aerobic carboxydotrophes, the group of aerobic $CO_2$ fixing organisms, the group of methylotrophes, and the group of methanogens.

In one embodiment, the parental microorganism is selected from the group of carboxydotrophic acetogenic bacteria. In certain embodiments the microorganism is selected from the group comprising *Clostridium* autoethanogenum, *Clostridium* ljungdahlii, *Clostridium* ragsdalei, *Clostridium* carboxidivorans, *Clostridium* drakei, *Clostridium* scatologenes, *Clostridium* coskatii, *Clostridium* aceticum, *Clostridium* magnum, *Clostridium* sp., *Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi*.

These carboxydotrophic acetogens are defined by their ability to utilize and grow chemoautotrophically on gaseous one-carbon (C1) sources such as carbon monoxide (CO) and carbon dioxide (CO2) with carbon monoxide (CO) and/or hydrogen (H2) as energy source under anaerobic conditions forming acetyl-CoA, acetate and other products. They share the same mode of fermentation, the Wood-Ljungdahl or reductive acetyl-CoA pathway, and are defined by the presence of the enzyme set consisting of Carbon monoxide dehydrogenase (CODH), Hydrogenase, Formate dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase (CODH/ACS), which combination is characteristic and unique to this type of bacteria (Drake, Küsel, Matthies, Wood, & Ljungdahl, 2006). In contrast to chemoheterotrophic growth of sugar-fermenting bacteria that convert the substrate into biomass, secondary metabolites and pyruvate from which products are formed (either via acetyl-CoA or directly), in acetogens the substrate is channelled directly into acetyl-CoA, from which products, biomass, and secondary metabolites are formed.

In a one embodiment, the microorganism is selected from a cluster of carboxydotrophic Clostridia comprising the species *C. autoethanogenum*, *C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593,886), *C. ljungdahlii* C-01 (ATCC 55988) (U.S. Pat. No. 6,368,819), *C. ljungdahlii* O-52 (ATCC 55989) (U.S. Pat. No. 6,368,819), or "*C. ragsdalei* P11$^T$" (ATCC BAA-622) (WO 2008/028055), and related isolates such as "*C. coskatii*" (US patent 2011/0229947), "*Clostridium* sp. MT351" (Tyurin & Kiriukhin, 2012), and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010) or "*Clostridium* sp. MT896" (Berzin, Kiriukhin, & Tyurin, 2012).

These strains form a subcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a GC composition of around 32% mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde: ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et al., 1994; Köpke et al., 2011; Tanner et al., 1993) (WO differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

In one embodiment, the parental strain uses CO as its sole carbon and energy source.

In certain embodiments, the parental microorganism is selected from the group comprising *Clostridium* autoethanogenum, *Clostridium ljungdahlii*, and *Clostridium ragsdalei*. In one embodiment, the group also comprises *Clostridium coskatii*. In one particular embodiment, the microorganism is *Clostridium autoethanogenum* DSM10061 or DSM23693. In another particular embodiment, the microorganism is *Clostridium ljungdahlii* DSM13528 (or ATCC55383).

In one embodiment, the parental microorganism is an ABE fermenting microorganism. An "ABE fermenting microorganism" or "ABE microorganism" is a Gram-positive, Clostridial organism which is able to produce the solvents butanol, and ethanol, and acetone or isopropanol. Genera in this group include *Clostridium* acetobutylicum, *Clostridium* beijerinckii, *Clostridium* saccharobutylicum, and *Clostridium* saccharoperbutylacetonicum. These organisms are all sporulating, Gram-positive and within the Clostridial rRNA cluster I. This group has been described in detail by Keis et al. (Keis, Shaheen, & Jones, 2001).

In one particular embodiment, the ABE microorganism is selected from the group comprising *Clostridium* acetobutylicum, *Clostridium* beijerinckii, *Clostridium* saccharobutylicum, *Clostridium* saccharoperbutylacetonicum.

In one embodiment the parental microorganism is *Clostridium acetobutylicum* or *Clostridium beijerinckii*. In one particular embodiment, the microorganism is *Clostridium acetobutylicum* ATCC824 (DSM792) or EA 2018 (CCTCC M 94061). In another particular embodiment, the microorganism is *Clostridium beijerinckii* NCIMB8052 (ATCC51743) and NRRL B-593 (DSM 6423).

In one embodiment, the parental microorganism is an Enterobacteria. An Enterobacteria is a rod-shaped Gram-negative bacteria belonging to the order of Enterobacteriacea which is able to fermenting sugars to produce lactic acid, and/or ethanol, and/or acetoin, and/or 2,3-butabediol, and/or other products.

In one particular embodiment, the Enterobacteria is selected from the group comprising *Escherichia*, *Klebsiella*, *Zymomonas*, *Citrobacter*, *Enterobacter*, *Salmonella*, *Serra-* tia. In one embodiment the parental microorganism is *Eschericia coli, Zymononas mobilis, Klebsiella pneumonia, Klebsiella oxtoca, Enterobacter cloacae* or *Serratia marcescens*.

In one embodiment, the parental microorganism is a *Lactobacillus*. A *Lactobacillus* is a gram-positive lactic acid bacteria selected from the order of Lactobacillales which is able to fermenting sugars to produce lactic acid, and/or 2,3-butabediol, and/or MEK, and/or 2-butanol, and/or other products.

In one particular embodiment, the *Lactobacillus* is selected from the group comprising *Lactobacillus, Lactococcus, Enterococcus, Pediococcus, Streptococcus*. In one embodiment the parental microorganism is *Lactobacillus brevis, Enterococcus faecalis, Lactococcus* lactis.

In one embodiment, the parental microorganism is a fungi or yeast. Fungi are eukaryotic microorganisms, and yeast are a specific subset thereof, which are able to ferment sugars to ethanol and/or acetoin, and/or other products.

In one particular embodiment, the Fungi is selected from the group comprising *Aspergillus, Trichoderma, Exophila, Mucor, Cladosporium, Phanerochaete, Cladiophilalophora, Paecilomyces, Scedosporium, Ophistoma*. In one embodiment the parental microorganism is *Aspargillus niger* or *Trichderma resei*.

In one particular embodiment, the yeast is selected from the group comprising *Saccharomyces, Pichia, Candida Hansenula, Yarrowia, Rhodotorula, Rhizopus, Trichosporon, Lipomyces* and from the group comprising *Aspergillus, Trichoderma, Exophila, Mucor, Cladosporium, Phanerochaete, Cladiophilalophora, Paecilomyces, Scedosporium, Ophistoma*. In one embodiment the parental microorganism is *Saccharomyces cerevisiae, Candidia tropicalis, Candidia albicans* or *Yarrowia lipolytica*. In one embodiment the parental microorganism is *Aspargillus niger* or *Trichderma resei*.

In one embodiment, parental the microorganism is an aerobic carboxydotroph. Aerobic carboxydotrophes are bacteria that can be found ubiquitous in nature and have been isolated from various environments as well as humans (King and Weber, 2007). On taxonomic level, this physiological group is quite diverse, comprising of different phyla such as α-proteobacteria, firmicutes, or actinobacteria (King and Weber, 2007). All these organisms were shown to grown on CO levels >1% in presence of air (King and Weber, 2007). A typical gas mix consists of 50% CO and 50% air (Cypionka et al., 1980).

In a particular embodiment, the parental microorganism is selected from the group comprising *Bacillus, Oligotropha, Pseudomonas, Carbophilus, Hydrogenophaga, Mycobacterium, Zavarzinia*. In one embodiment the parental microorganism is *Oligotropha carboxydovorans, Carbophilus carboxidus, Hydrogenophaga pseudoflava, Mycobacterium* sp., *Pseudomonas carboxydohydrogena, Pseudomonas* sp., *Zavarzinia compransoris* or *Bacillus schlegelii*.

In one embodiment, the parental microorganism is an aerobic $CO_2$ fixing organism. An aerobic CO2 fixing microorganism is an bacteria able to fix CO2 with H2 or via photosynthesis in present of oxygen. The aerobic CO2 fixing microorganism is selected from the group comprising *Cupravidus, Senechocystis, Chloroflexus*. In one embodiment the parental microorganism is *Cupravidus necator, Senechocystis* sp. or *Chloroflexus auranticus*.

In one embodiment, the parental microorganism is a methylotroph. Methylotrophic microrgansims are able to use reduced one-carbon substrates as methane or methanol as carbon source for growth. The methylotrop is selected from the group comprising *Methylomonas, Methylobacter, Methylococcus, Methylomicrobium, Methylosphera, Methylocaldum, Methylocystis, Methylosinus*. In one embodiment the parental microorganism is *Methylococcus capsulatus* or *Methylosinus trichosporium*.

In one embodiment, the parental microorganism is a methanogen. A methanogen is an Archeae that can reduce CO2 into methane. The methanogen is selected from the group comprising *Methanobacterium, Methanococcus, Methanogenium, Methanosarcina, Methanoshera, Methanothermobacter, Methanotrix*. In one embodiment the parental microorganism is

*Methanothermobacter marburgensis* or *Methanosarcina bakeri*.

Methods

The invention provides a method for the production of isopropanol, ethanol, 2,3-butanediol and/or 2-butanol and optionally one or more other products by microbial fermentation of a substrate using a recombinant microorganism of the invention.

In another embodiment, the invention provides a method for the production of one or more of acetoin, MEK, acetaldehyde and acetone, and optionally one or more other products.

In one embodiment, the substrate is a substrate comprising one or more carbohydrate. In another embodiment, the substrate is a substrate comprising one or a combination of CO, CO2, and $H_2$. In certain embodiments, mixed substrates comprising both one or more carbohydrate and a substrate comprising one or more of CO, CO2, and $H_2$ may be used.

In one embodiment the method comprises the steps of:
(a) providing a substrate to a bioreactor containing a culture of one or more microorganism of the invention; and
(b) fermenting the culture in the bioreactor to produce one or more of isopropanol, 2,3-butanediol, ethanol and 2-butanol and, optionally, one or more other products.

Preferably, the one or more product includes isopropanol.

In one embodiment the method comprises the steps of:
(c) providing a substrate to a bioreactor containing a culture of one or more microorganism of the invention; and
(d) fermenting the culture in the bioreactor to produce one or more of acetoin, MEK, acetaldehyde and acetone and, optionally, one or more other products.

The method may further comprise the step of recovering one or more products. In certain embodiments, the one or more products are intermediates in the production of one or more downstream products. In this embodiment, the one or more products may be recovered and then used as a substrate in a separate fermentation or in a chemical synthesis reaction, for example. In another embodiment, the one or more products are not recovered and are converted to one or more downstream products in the same fermentation process.

It will be appreciated that for growth of the microorganism and conversion of substrate-to-the one or more product(s) to occur, in addition to the substrate, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Suitable media for fermentation will be known in the art. However, by way of example, for fermentation of a substrate comprising one or more carbohydrate, Luria Broth (LB), Yeast Extract Peptone Dextrose (YEPD) or reinforced clostridia media (RCM) may be used. In addition, anaerobic media suitable for fermentation using CO are known in the art but by way of example, suitable media are described Biebel (2001). n one embodiment of the invention the media is as described in the Examples section herein after.

The fermentation should desirably be carried out under appropriate conditions for the substrate-to-the one or more product(s), and optionally one or more other product(s), fermentation to occur. Reaction conditions that should be considered include pressure, temperature, gas flow rate, liquid flow rate, media pH, media redox potential, agitation rate (if using a continuous stirred tank reactor), inoculum level, maximum substrate concentrations to ensure that the substrate does not become limiting, and maximum product concentrations to avoid product inhibition.

As noted above, fermentations will be carried out using appropriate media and fermentation conditions. In one embodiment, where gaseous substrates are used, maximum gas substrate concentrations are considered to ensure that CO (and/or $CO_2$ and/or $H_2$) in the liquid phase does not become limiting.

In addition, it is often desirable to increase the CO (and/or $CO_2$ and/or $H_2$) concentration of a substrate stream (or CO (and/or $CO_2$ and/or $H_2$) partial pressure in a gaseous substrate) and thus increase the efficiency of fermentation reactions where CO (and/or $CO_2$ and/or $H_2$) is a substrate. Operating at increased pressures allows a significant increase in the rate of CO (and/or $CO_2$ and/or $H_2$) transfer from the gas phase to the liquid phase where it can be taken up by the microorganism as a carbon source for the production of one or more products. This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also, since a given CO (and/or $CO_2$ and/or $H_2$)-to-the one or more product(s) conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

By way of example, the benefits of conducting a gas-to-ethanol fermentation at elevated pressures has been described. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO (and/or $CO_2$ and/or $H_2$)-containing gaseous substrate is such as to ensure that the concentration of CO (and/or $CO_2$ and/or $H_2$) in the liquid phase does not become limiting. This is because a consequence of CO (and/or $CO_2$ and/or $H_2$)-limited conditions may be that the product(s) is consumed by the culture.

The composition of gas streams used to feed a fermentation reaction can have a significant impact on the efficiency and/or costs of that reaction. For example, $O_2$ may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a microorganism of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

In embodiments of the invention comprising fermentation of a substrate comprising CO the fermentation comprises the steps of anaerobically fermenting the substrate in a bioreactor to produce the one or more products using a recombinant microorganism of the invention.

Methods of this embodiment may be used to reduce the total atmospheric carbon emissions from an industrial process.

In one embodiment the method comprises the steps of:
(a) providing a substrate comprising CO to a bioreactor containing a culture of one or more microorganism of the invention; and
(b) anaerobically fermenting the culture in the bioreactor to produce one or more of isopropanol, 2,3-butanediol, ethanol and 2-butanol and, optionally, one or more other products.

In another embodiment, the one or more products in step (b) above are acetoin, MEK, acetaldehyde and acetone, and optionally, one or more other products.

In one embodiment the method comprises the steps of:
capturing CO-containing gas produced as a result of the industrial process, before the gas is released into the atmosphere;
the anaerobic fermentation of the CO-containing gas to produce one or more of isopropanol, 2,3-butanediol, ethanol and 2-butanol and optionally one or more other products by a culture containing one or more microorganism of the invention.

In another embodiment, the one or more products in step (b) above are acetoin, MEK, acetaldehyde and acetone, and optionally, one or more other products.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing CO$_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

Skilled persons will readily appreciate various methodology of use in fermentations using substrates comprising one or more carbohydrates. However, by way of example, the methodology described in Vogel, H. C., & Todaro, C. C. (2007). Fermentation and Biochemical Engineering Handbook: Principles, process design and equipment (ISBN: 0-8155-1407-7); Vogel, H. C., & Todaro, C. C. (1996). Fermentation and Biochemical Engineering Handbook (ISBN: 978-O-8155-1407-7); Ezeji T C, Qureshi N, Blaschek H P (2005) Industrial relevant fermentations. in Handbook on Clostridia, ed Dürre P (CRC Press, Boca Raton, Fla.), pp 799-814 may be used.

Product Recovery

Isopropanol, 2,3-butanediol, ethanol, 2-butanol, acetoin, MEK, acetaldehyde and/or acetone or a mixed stream containing any one or more of these products and acetone and optionally one or more other products, may be recovered from the fermentation broth by methods known in the art, such as fractional distillation or evaporation, pervaporation, gas stripping and extractive fermentation, including for example, liquid-liquid extraction.

In certain preferred embodiments of the invention, the one or more products are recovered from the fermentation broth by continuously removing a portion of the broth from the bioreactor, separating microbial cells from the broth (conveniently by filtration), and recovering one or more products from the broth. Alcohols may conveniently be recovered for example by distillation. Acetone may be recovered for example by distillation. Any acids produced may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

EXAMPLES

Example 1

Characterisation of Wild-Type Alcohol Dehydrogenase of C. Autoethanogenum and Range of Substrate Specificity with Single Amino Acid Substitutions Several species of Clostridium, including C. ljungdahlii (Köpke, et al., 2010) have been shown to utilise CO as a sole carbon source, with ethanol as the end product. The bacteria are able to fix CO and convert it to acetyl-CoA via the Wood-Ljungdahl pathway. The acetyl moiety of the acetyl CoA can then be used in a variety of metabolic pathways. Of particular interest here the carbonyl group can be reduced to its corresponding alcohol by an alcohol dehydrogenase (ADH) enzyme (Köpke, et al., 2010). This provides a pathway to convert CO into commercially valuable biofuels and biochemicals.

Genome sequencing of a strain of C. autoethanogenum DSM10061 identified an ADH that is 86% identical to the previously-characterized enzyme from C. beijerinckii. The ADH from this strain is able to utilise acetaldehyde as its substrate and produce ethanol as the end product. It is also able to catalyse the reduction of acetone to isopropanol.

Isopropanol is a more economically valuable final product than ethanol, as it can be dehydrated to form propylene, which can be polymerised to polypropylene, a commonly used plastic (Inokuma et al., 2010). A microbial route to propylene will also decrease the demand for petroleum, from which most propylene is currently derived.

Mutagenesis studies were completed with the aim of improving the efficiency of isopropanol production via the ADH enzyme. Five mutants were constructed and tested: Ser199Asp, Ser199Glu, Arg200Gln, Arg200Glu and a double mutant Ser199Glu/Arg200Gln.

Materials

Microorganisms and Growth Conditions

E. coli DH5α-E was obtained from Invitrogen. The genotype of this strain is: F-80ΔlacZM15 (lacZYA-argF) U169 recA1 endA1 hsdR17(rk-, mk+) gal- phoA supE44- thi-1 gyrA96 relA1.

E. coli LMG194 was obtained from Invitrogen. The genotype of this strain is: F-ΔlacX74 galE thi rpsL ΔphoA (Pvu II) Δara714 leu::Tn10.

E. coli MC1061 was obtained from Coli Genetic Stock Centre. The genotype of this strain is araD139 Δ (araA-leu) 7697 Δ (lac)X74 galK16 galE15(GalS) lambda- e14- mcrA0 relA1 rpsL150(strR) spoT1 mcrB1 hsdR2.

Clostridium autoethanogenum DSM10061 was obtained from DSMZ (The German Collection of Microorganisms and Cell Cultures, Inhoffenstraβe 7 B, 38124 Braunschweig, Germany).

C. acetobutylicum ATCC824 and C. beijerinckii NCIMB8052 were obtained from Prof. David Jones (University of Otago) and can also be obtained from public strain collections DSMZ and ATCC under accession numbers ATCC824/DSM792 and ATCC51743 respectively.

All E. coli strains were cultivated in aerobic conditions, using Luria Burtani medium supplmented with either ampicillin (100 g/mL) or carbenicillin (50 g/mL). [098] Solid media contained 1.5% agar. All strains were grown at 37° C. unless otherwise noted.

SOC medium (20 g/L tryptone, 5 g/L yeast extract, 10 mM NaCl, 2.5 mM KCl and 20 mM glucose) was used for recovery of E. coli after electroporation.

Clostridium autoethanogenum was grown in PETC media with pH5.6 (Tab. 1) and C. acetobutylicum and C. beijerinckii in RCM media (Tab. 2) using standard anaerobic techniques [Hungate R E: A roll tube method for cultivation of strict anaerobes, in Norris J R and Ribbons D W (eds.), Methods in Microbiology, vol. 3B. Academic Press, New York, 1969: 117-132; Wolfe R S: Microbial formation of methane. Adv Microb Physiol 1971, 6: 107-146].

TABLE 1

| PETC medium | |
|---|---|
| Media component | Concentration per 1.0 L of media |
| NH$_4$Cl | 1 g |
| KCl | 0.1 g |

TABLE 1-continued

| PETC medium | |
|---|---|
| MgSO$_4$•7H$_2$O | 0.2 g |
| NaCl | 0.8 g |
| KH$_2$PO$_4$ | 0.1 g |
| CaCl$_2$ | 0.02 g |
| Trace metal solution (see below) | 10 ml |
| Wolfe's vitamin solution (see below) | 10 ml |
| Yeast Extract (optional) | 1 g |
| Resazurin (2 g/L stock) | 0.5 ml |
| NaHCO$_3$ | 2 g |
| Reducing agent | 0.006-0.008% (v/v) |
| Fructose (for heterotrophic growth) | 5 g |

| Trace metal solution | per L of stock |
|---|---|
| Nitrilotriacetic Acid | 2 g |
| MnSO$_4$•H$_2$O | 1 g |
| Fe(SO$_4$)$_2$(NH$_4$)$_2$•6H$_2$O | 0.8 g |
| CoCl$_2$•6H$_2$O | 0.2 g |
| ZnSO$_4$•7H$_2$O | 0.2 mg |
| CuCl$_2$•2H$_2$O | 0.02 g |
| NaMoO$_4$•2H$_2$O | 0.02 g |
| Na$_2$SeO$_3$ | 0.02 g |
| NiCl$_2$•6H$_2$O | 0.02 g |
| Na$_2$WO$_4$•2H$_2$O | 0.02 g |

TABLE 1-continued

| PETC medium | |
|---|---|
| Reducing agent stock | per 100 mL of stock |
| NaOH | 0.9 g |
| Cystein•HCl | 4 g |
| Na$_2$S | 4 g |

TABLE 2

Reinforced Clostridial Medium RCM (*C. acetobutylicum*, *C. beijerinckii*)

| Media component | Concentration per 1.0 L of media |
|---|---|
| Pancreatic Digest of Casein | 5 g |
| Proteose Peptone No. 3 | 5 g |
| Beef Extract | 10 g |
| Yeast Extract | 3 g |
| Dextrose | 5 g |
| NaCl | 5 g |
| Soluble starch | 1 g |
| Cystein•HCl | 0.5 g |
| Sodium Acetate | 3 g |

ADH Gene and Protein

The amino acid and nucleic acid sequence of the wild-type ADH of *C. autoethanogenum* DSM10061 are shown in SEQ ID 36 and SEQ ID 35, respectively.

Primers

TABLE 3

Oligonucleotides for amplification and site directed mutagenesis.

| Primer name | Primer sequence (5' to 3') | SEQ ID No. |
|---|---|---|
| ADH_BspHI_for | GGTAATCATGAAAGGTTTTGCAATGTTAGGTATTAAC | 1 |
| ADH_HindIII_rev | TCTAGAAGCTTAGAATGTAACTACTGATTTAATTAAATCTTTTGG | 2 |
| pBAD_for | ATGCCATAGCATTTTTATCC | 3 |
| ADH_TEV_KpnI_for | CAGGTACCGAGAACCTGTATTTCCAAGGAAAAGGTTTTGCAATGTTAGGTATTAAC | 4 |
| ADH_Arg200Glu_rev | CACAAACAGGTTCGCTTCCAACACCG | 5 |
| ADH_Arg200Glu_for | CGGTGTTGGAAGCGAACCTGTTTGTG | 6 |
| ADH_Ser199Glu_rev | CAAACAGGTCTTTCTCCAACACCG | 7 |
| ADH_Ser199Glu_for | CGGTGTTGGAGAAAGACCTGTTTG | 8 |
| ADH_Ser199Glu_Arg200Gln_rev | CACAAACAGGCTGTTCTCCAACACCG | 9 |
| ADH_Ser199Glu_Arg200Gln_for | CGGTGTTGGAGAACAGCCTGTTTGTG | 10 |
| ADH_Ser199Asp_rev | CAAACAGGTCTGTCTCCAACACCG | 11 |
| ADH_Ser199Asp_for | CGGTGTTGGAGACAGACCTGTTTG | 12 |
| ADH_Arg200Gln_for | CGGTGTTGGAAGCCAGCCTGTTTGTG | 13 |
| ADH_Arg200Gln_rev | CACAAACAGGCTGGCTTCCAACACCG | 14 |

Figure 13:
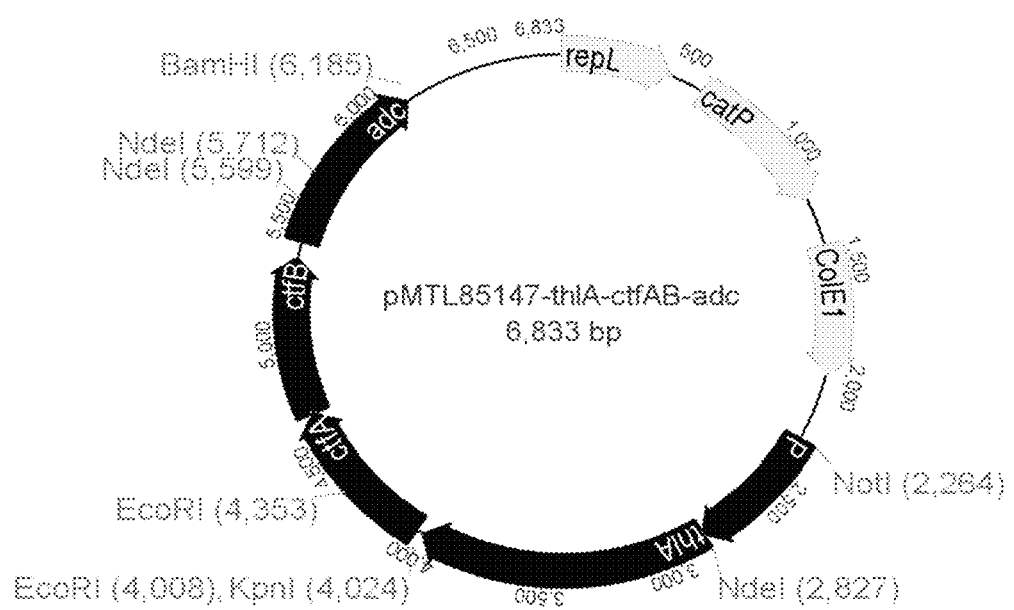
FIG. 13: Plasmid map of pMTL85147-T—hlA-CtfAB-Adc-Adh

Plasmids pMTL85147-ThlA-CtfAB-Adc-Adh (FIG. 13) was used for amplification of *C. autoethanogenum* DSM10061 ADH gene.

Plasmid pMTL85147-ThlA-CtfAB-Adc-Adh has been constructed using standard Recombinant DNA and molecular cloning techniques [Sambrook J, Fritsch E F, Maniatis T: Molecular Cloning: A laboratory Manual, Cold Spring Harbour Laboratory Press, Cold Spring Harbour, 1989; Ausubel F M, Brent R, Kingston R E, Moore D D, Seidman J G, Smith J A, Struhl K: Current protocols in molecular biology. John Wiley & Sons, Ltd., Hoboken, 1987]. ThlA gene (NC_003030.1; GI: 1119056) was amplified from genomic DNA of *C. acetobuylicum*, genes adc-ctfAB-adc (NC_009617; region: 4,400,524-4,402,656; including GI: 5294994, GI: 5294995, and GI: 5294996) were amplified from *C. beijerinckii*, and adh gene (FIG. 5) and Wood-Ljungdahl promoter region (SEQ ID 39) were amplified from *C. autoethanogenum* DSM10061. Oligonucleotide sequences used for amplification are given in Tab. 4. All amplified fragments were subsequently cloned into plasmid pMTL 85141 (FJ797651.1; Nigel Minton, University of Nottingham, UK) [Heap J T, Pennington O J, Cartman S T, Minton N P. A modular system for *Clostridium* shuttle plasmids. J Microbiol Methods. 2009, 78: 79-85] using restriction sites NotI, NdeI, EcoRI, KpnI, BamHI, SalI, XhoI. The final plasmid is given in SEQ ID 40 and has been sequenced to ensure it's free of mutations.

Genomic DNA from *Clostridium acetobutylicum* ATCC824, *C. beijerinckii* NCIMB8052 and *C. autoethanogenum* DSM10061 was isolated using a modified method by Bertram and Dürre (Conjugal transfer and expression of streptococcal transposons in *Clostridium* acetobutylicum. Arch Microbiol 1989, 151: 551-557). A 100-ml overnight culture was harvested (6,000×g, 15 min, 4° C.), washed with potassium phosphate buffer (10 mM, pH 7.5) and suspended in 1.9 ml STE buffer (50 mM Tris-HCl, 1 mM EDTA, 200 mM sucrose; pH 8.0). 3001 lysozyme (~100,000 U) were added and the mixture was incubated at 37° C. for 30 min, followed by addition of 2801 of a 10% (w/v) SDS solution and another incubation for 10 min. RNA was digested at room temperature by addition of 2401 of an EDTA solution (0.5 M, pH 8), 201 Tris-HCl (1 M, pH 7.5), and 101 RNase A. Then, 1001 Proteinase K (0.5 U) were added and proteolysis took place for 1-3 h at 37° C. Finally, 6001 of sodium perchlorate (5 M) were added, followed by a phenol-chloroform extraction and an isopropanol precipitation. DNA quantity and quality was inspected spectrophotometrically.

The expression vector pBAD(KpnI)-WpiMetC was obtained from Invitrogen. The plasmid used in this study had been modified previously, by the insertion of a fragment encoding a hexahistidine ($His_6$) tag, a TEV protease cleavage site (for removing $His_6$ from ADH, if desired, after purification), and the gene encoding the MetC enzyme from an unrelated bacterium (*Wolbachia pipientis*).

Methods

Amplification of Wild Type ADH:

The wild type ADH *C. autoethanogenum* DSM10061 was amplified from a 50 ng/µl working stock of the plasmid pMTL85147-ThlA-CtfAB-Adc-Adh(LZ) using the primers ADH_TEV_KpnI_for and ADH_HindIII_Reverse.

A 50 µL PCR mixture was made as follows:

| Reagent | Initial Conc | Final Conc | Vol/reaction |
| --- | --- | --- | --- |
| Phusion Buffer | 5x | 1x | 10 µL |
| dNTPs | 2 mM | 200 µM each dNTP | 5 µL |
| ADH_TEV_KpnI_for | 10 mM | 0.5 µM | 2.5 µL |
| ADH_HindIII_Rev | 10 Mm | 0.5 µM | 2.5 µL |
| Phusion Polymerase | 2 U/µL | 1 U/reaction | 0.5 µL |
| pMTL85147-ThlA-CtfAB-Adc-Adh (LZ) template DNA | 50 ng/µL | 20 ng | 0.4 µL |
| Water | | | 29.1 |

The following cycling conditions were used:

| Step | Temperature (° C.) | Duration | |
| --- | --- | --- | --- |
| Initial Denaturation | 98 | 30 sec | |
| Denaturation | 98 | 10 sec | 30 Cycles |
| Annealing | 60 | 30 sec | |
| Extension | 72 | 20 sec | |
| Final extension | 72 | 5 min | |

TABLE 4

Oligonucleotides used for amplification of acetone biosynthesis genes and promoter region

| Description | Oligonucleotide Name | DNA Sequence (5' to 3') | SEQ ID No. |
| --- | --- | --- | --- |
| ThlA | ThlA-Cac-NdeI-F | GTT<u>CATATG</u>AAAGAAGTTGTAATAGC | 15 |
| | ThlA-Cac-EcoRI-R | CAA<u>GAATTC</u>CTAGCACTTTTCTAGC | 16 |
| CtfA, CtfB, Adc operon | Ctf-adc-cbei-KpnI-F | CTA<u>GGTACC</u>AGGGAGATATTAAAATG | 17 |
| | Ctf-adc-cbei-BamHI-R | CGT<u>GGATCC</u>TCTATATTGCTTTTATT | 18 |
| Promoter | Pwoodlj-NotI-F | AA<u>GCGGCCGC</u>AGATAGTCATAATAGTTCC | 19 |
| | Pwoodlj-NdeI-R | TTC<u>CATATG</u>AATAATTCCCTCCTTAAAGC | 20 |
| Adh | SecAdh-SalI-F | TATTTGTCGACTTAGGAGGTTCTATTATGAAAGG | 21 |
| | SecAdh-XhoI-R | AAAACTCGAGACATTTTTTTAATGCGACAG | 22 |

The product was cleaned up with the Cycle Pure kit (Omega Bio-Tek).

Digestion of Vector and Insert:

The pBAD backbone was prepared by digesting pBAD (KpnI)-WpiMetC with the enzymes KpnI-HF and HindIII, with the following recipe:

| Reagent | Initial Concentration | Final Concentration | Volume in Reaction |
| --- | --- | --- | --- |
| NEB Buffer 4 | 10X | 1X | 5 µL |
| pBAD(KpnI)-WpiMetC | 140 ng/µL | 4.1 µg | 28 µL |
| KpnI-HF | 20,000 U/mL | 10 U/reaction | 0.5 µL |
| HindIII | 20,000 U/mL | 10 U/reaction | 0.5 µL |
| Water | | | 16 µL |

The amplified ADH gene was similarly digested with KpnI-HF and HindIII:

| Reagent | Initial Concentration | Final Concentration | Volume in Reaction |
| --- | --- | --- | --- |
| NEB Buffer 4 | 10X | 1X | 5 µL |
| WT ADH | 75 ng/µL | 1.8 µg | 25 µL |
| KpnI-HF | 20,000 U/mL | 10 U/reaction | 0.5 µL |
| HindIII | 20,000 U/mL | 10 U/reaction | 0.5 µL |
| Water | | | 19 µL |

Both digestions were carried out at 37° C. for 16 hours. The digested products were separated on a 1% agarose gel stained with SYBRsafe (Invitrogen). The bands corresponding to digested vector and insert were excised and the DNA was recovered using a gel clean-up kit (Omega Bio-Tek).

Construction of pBAD(KpnI)-ADH

The purified DNA from the ADH and pBAD digestions were ligated, alongside a control ligation, in the following reaction, which contained a 3× molar excess of insert over vector:

| | | | Volume per reaction mixture | |
| --- | --- | --- | --- | --- |
| Reagent | Initial concentration | Final Concentration | Insert + Vector | Vector Only (Control) |
| Ligation buffer | 10x | 1x | 2 µL | 2 µL |
| Vector | 50 ng/µL | 100 µg/reaction | 2 µL | 2 µL |
| Insert | 45 ng/µL | 76.5 µg/reaction | 1.7 µL | — |
| T4 DNA ligase | 20 U/µL | 0.5 U/µL | 0.5 µL | 0.5 µL |
| Water | | | 11.5 µL | 14.5 µL |

The reaction was incubated at 16° C. for 2 hours. A 2 µL aliquot of the ligation mixture was used to transform a 50 µL aliquot of *E. coli* MC1061 cells by electroporation. After an hour recovery at 37° C. in SOC, aliquots were spread on LB-ampicillin plates and incubated at 37° C. overnight. 6 colonies were picked and screened for the presence of the ADH insert by PCR using the pBAD_for and ADH_HindIII_rev primers. A freezer stock was made of a successful clone, with 7001 culture and 300 µl sterile 50% (v/v) glycerol. The sequence of the ADH gene was verified by DNA sequencing.

Site Directed Mutagenesis of ADH

The protocol for constructing all 5 mutants by overlap extension PCR was the same, except each mutant was constructed with its corresponding mutagenic primers. Hence, the protocol to produce one mutant only has been provided.

Generation of Ser199Asp Primary Products:

The first step in site directed mutagenesis was the generation of two overlapping primary products. The PCR reactions for these are as follows:

Primary Product 1.0:

| Reagent | Initial concentration | Final Concentration | Volume per reaction |
| --- | --- | --- | --- |
| Phusion Buffer | 5x | 1x | 20 µL |
| dNTPs | 2 mM | 200 µM each dNTP | 10 µL |
| ADH_TEV_KpnI_for | 10 mM | 0.5 µM | 5 µL |
| Ser199Asp_rev | 10 mM | 0.5 µM | 5 µL |
| Phusion Polymerase | 2 U/µL | 1 U/reaction | 1 µL |
| pMTL85147-ThlA-CtfAB-Adc-Adh(LZ) template DNA | 50 ng/µL | 40 ng | 0.8 µL |
| Water | | | 58.2 µL |

Primary Product 1.1:

| Reagent | Initial concentration | Final Concentration | Volume per reaction |
| --- | --- | --- | --- |
| Phusion Buffer | 5x | 1x | 20 µL |
| dNTPs | 2 mM | 200 µM each dNTP | 10 µL |
| Ser199Asp_For | 10 mM | 0.5 µM | 5 µL |
| ADH_HindIII_Rev | 10 mM | 0.5 µM | 5 µL |
| Phusion Polymerase | 2 U/µL | 1 U/reaction | 1 µL |
| pMTL85147-ThlA-CtfAB-Adc-Adh(LZ) template DNA | 50 ng/µL | 40 ng | 0.8 µL |
| Water | | | 58.2 µL |

The cycling conditions were as follows:

| Step | Temperature (° C.) | Duration | |
| --- | --- | --- | --- |
| Initial Denaturation | 98 | 30 sec | |
| Denaturation | 98 | 10 sec | 30 Cycles |
| Annealing | 60 | 30 sec | |
| Extension | 72 | 10 sec | |
| Final extension | 72 | 5 min | |

The products were cleaned up with the Omega Cycle Pure kit.

Generation of Ser199Asp Secondary Products:

The next step in site directed mutagenesis was to use overlap extension PCR (Ho S N, Hunt H D, Horton R M, Pullen J K, Pease L R. (1989) Site-directed mutagenesis by overlap extension using the polymerase chain reaction. Gene, 77, 51-59) with the outside primers, to recombine the two primary products into a full-length secondary product that contained the complete gene with the introduced mutation. The two primary products are mixed so that they are in equal molar concentrations. The following PCR recipe was used:

| Reagent | Initial concentration | Final Concentration | Volume per reaction |
| --- | --- | --- | --- |
| Phusion Buffer | 5x | 1x | 10 µL |
| dNTPs | 2 mM | 200 µM each dNTP | 5 µL |

-continued

| Reagent | Initial concentration | Final Concentration | Volume per reaction |
|---|---|---|---|
| ADH_TEV_KpnI_for | 10 mM | 0.5 μM | 2.5 μL |
| ADH_HindIII_Rev | 10 mM | 0.5 μM | 2.5 μL |
| Phusion Polymerase | 2 U/μL | 1 U/reaction | 0.5 μL |
| Product 1.0 | 7.5 ng/μL | 24 ng | 3.2 μL |
| Product 1.1 | 7.1 ng/μL | 19.8 ng | 2.8 μL |
| Water | | | 23.5 μL |

The cycling conditions were the same as for amplification of the wild-type ADH.

Construction of pBAD(KpnI)-ADH(Ser199Asp):

Digestion and ligation protocols for cloning each of the five ADH mutants (i.e. bearing the mutations: Ser199Asp; Ser199Glu; Arg200Gln; Arg200Glu; and Ser199Glu/Arg200Gln) were the same as those used to construct pBAD(KpnI)-ADH. The presence of each mutation was confirmed by DNA sequencing.

Expression and Purification of ADH Enzymes

Expression and purification protocols were the same for all the mutants as well as the wild type, except where noted. The protocol for expression and purification of the wild-type ADH is provided below.

Testing for Soluble Expression:

A 5 mL LB-ampicillin overnight culture from freezer stocks was grown at 37° C., and used to inoculate 100 mL LB-ampicillin the following morning. The culture was incubated at 37° C. until an $OD_{600}$ of 0.8 was reached. At this point, 1 mL of 20% arabinose was added and the culture was incubated at 28° C. for the remainder of the expression. 500 μL samples were taken at t=0 h, 2 h, 4 h, and 16 h (i.e. overnight). For each sample, cells were pelleted, and supernatant decanted. Pellets were then resuspended in HEPES buffer (50 mM Na-HEPES and 0.2 mM DTT, pH 8.0), and 0.2 μL each of Benzonase (Merck, 25 units/μL) and rLysozyme (Merck, 30 kU/μL) were added. The mixtures were incubated at room temperature for 15 min and then frozen (at −80° C.) and thawed 3 times. 10 μL was taken at this point from each mixture as 'total protein' samples. The remainder of the sample was centrifuged at 13000 rpm for 1 min, and the supernatant removed and placed on ice. A 10 μL aliquot of the supernatant was taken from each mixture as 'soluble protein' samples. To each 10 μL total and soluble protein sample, 10 μL of SDS buffer was added and all mixtures were heated at 98° C. for 5 min. 15 μL of each aliquot was loaded into an SDS-PAGE gel with 12% resolving gel and 4% stacking gel. The gel was run at 200V for 40 min. The gel was stained in overnight using Coomassie blue and then de-stained.

At the end of expression, the remainder of the 100 mL culture was pelleted in 50 mL tubes and stored frozen at −80° C.

Protein Purification:

Since the wild-type and mutant ADH enzymes all carried $His_6$tagsat their N-termini, they could all be purified using immobilized metal affinity chromatography. The frozen cell pellets described above (from 100 mL cultures) were resuspended in 10 mL ice-coldlysis buffer (50 mM potassium phosphate, 300 mM NaCl, pH 7.0), with 0.5 μl rLysozyme (30 kU/μl), 0.5 μl Benzonase (25 U/μl), and 50 μl protease inhibitor cocktail (Sigma). After a 30 min incubation on ice, the cells were lysed by sonication, insoluble debris was pelleted, and the supernatant was clarified using a 0.2 micron filter. The clarified supernatant was added to Talon resin (Clontech) which had been thoroughly washed with lysis buffer. A bed volume of 500 μL was used for purifying the wild-type ADH, and a bed volume of 200 μL was used for purifying each mutant. The protein was allowed to bind to the Talon resin for an hour at 4° C. and then washed several times with lysis buffer. The protein was eluted from the column using lysis buffer supplemented with 150 mM imidazole, and the eluant was collected in 500 μL fractions. Aliquots taken at various stages through the purification process, as well as all elution fractions, were run on an SDS page gel to confirm presence of the protein and determine the success of the purification. Proteins were exchanged into a storage buffer (50 mM potassium phosphate, 150 mM NaCl, 10% v/v glycerol, pH 7.0) using Amicon Ultra-4 Centrifugal Filter Units (Millipore).

Figure 2:
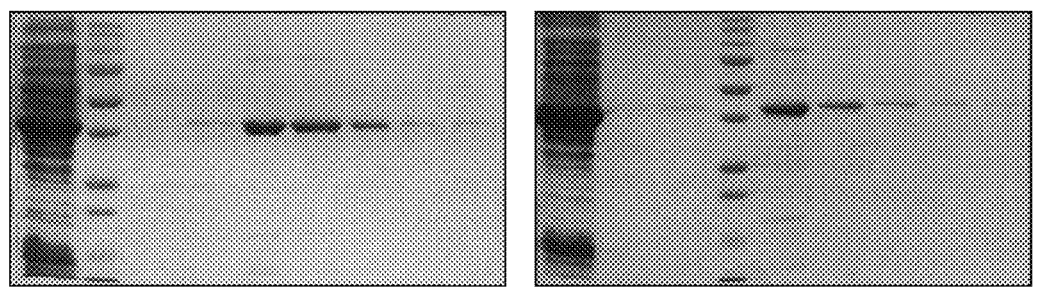
FIG. 2: shows that the Ser199Asp (left panel) and Arg200Gln (right panel) mutant proteins were highly soluble. Ser199Asp samples (left to right): total cell extract; ladder; column wash 1; column wash 2; elution fractions 1-5. Arg200Gln samples (left to right): total cell extract; column wash 1; column wash 2; ladder; elution fractions 1-5.

The wild-type protein was highly soluble when expressed in *E. coli*, and could be readily purified (FIG. 1). The Ser199Asp and Arg200Gln mutant proteins were also highly soluble (FIG. 2). The solubility of the other two point mutants (Ser199Glu and Arg200Glu) were more variable (results not shown). Somewhat surprisingly, the double mutant (Ser199Glu+Arg200Gln) was more soluble than Ser199Glu (results not shown).

The sequence of the Ser199Asp mutant is provided in SEQ ID 37 (nucleic acid) and SEQ ID 38 (amino acid).

Activity Assays

All activity assays were carried out using a Cary 100 UV/visspectrophotometer with quartz cuvettes. All chemicals used in the assay were sourced from Sigma-Aldrich.

Unless noted otherwise, assays had a cofactor (NADPH/NADH) concentration of 0.2 mM, a substrate (acetaldehyde, acetyl-CoA, acetone, DL-acetoin, MEK) concentration of 3 mM and an ADH concentration of 30 nM. They were carried out in 50 mM Tris-HCl buffer (pH 7.5), with 1 mM DTT. All assays were done in triplicate, with freshly prepared substrates and cofactors.

Figures 11, 12:
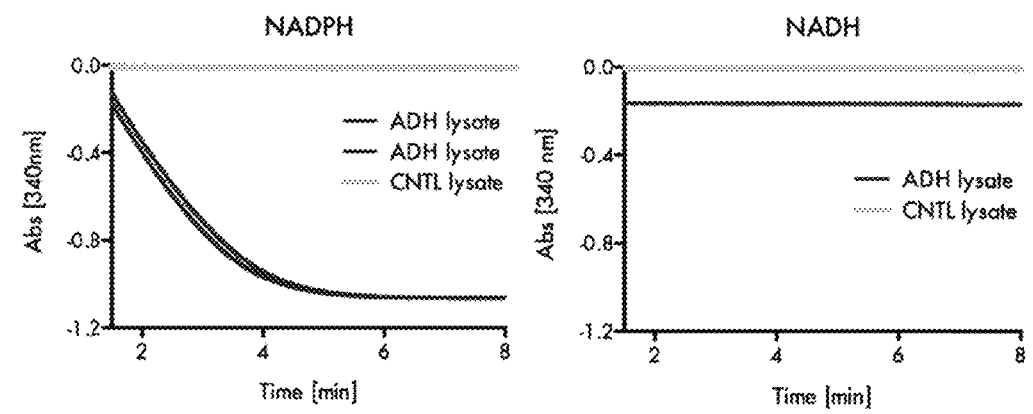
FIG. 11: Activity tests of *C. autoethanogenum* DSM10061 wild-type enzyme with NADH and NADPH as co-factor and acetone as substrate including control (CNTL).
FIG. 12: Kinetics, KM values and Activity measured for the wild type Adh enzyme with different substrates.

First, the wild-type enzyme of *C. autoethanogenum* was measured and it was shown that the enzyme is strictly NADPH dependent with barely any detectable activity with NADH (FIG. 11) as described for the alcohol dehydrogenase enzyme of *C. beijerinckii* (Ismaiel, Zhu, Colby, & Chen, 1993).

Figure 9:
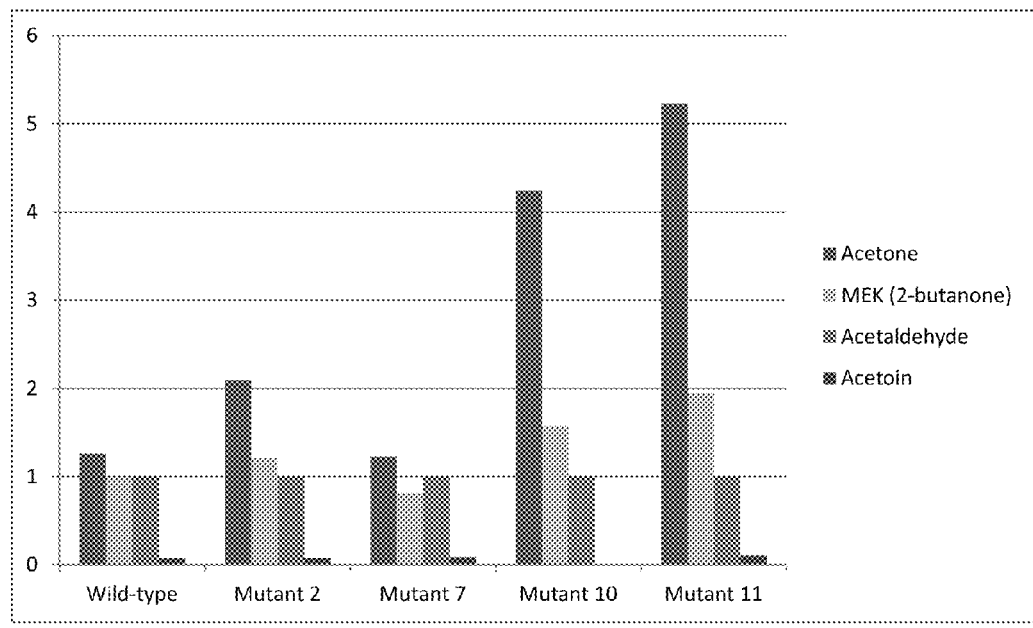
FIG. 9: shows the specific activity of the wild-type and mutant ADH enzymes with different substrates normalized to Acetaldehyde (acetaldehyde set=1). For each enzyme, the preferred cofactor was used (i.e. NADPH for wild-type ADH, Mutant 2 and Mutant 7; NADH for Mutant 10 and Mutant 11).
Figure 14:
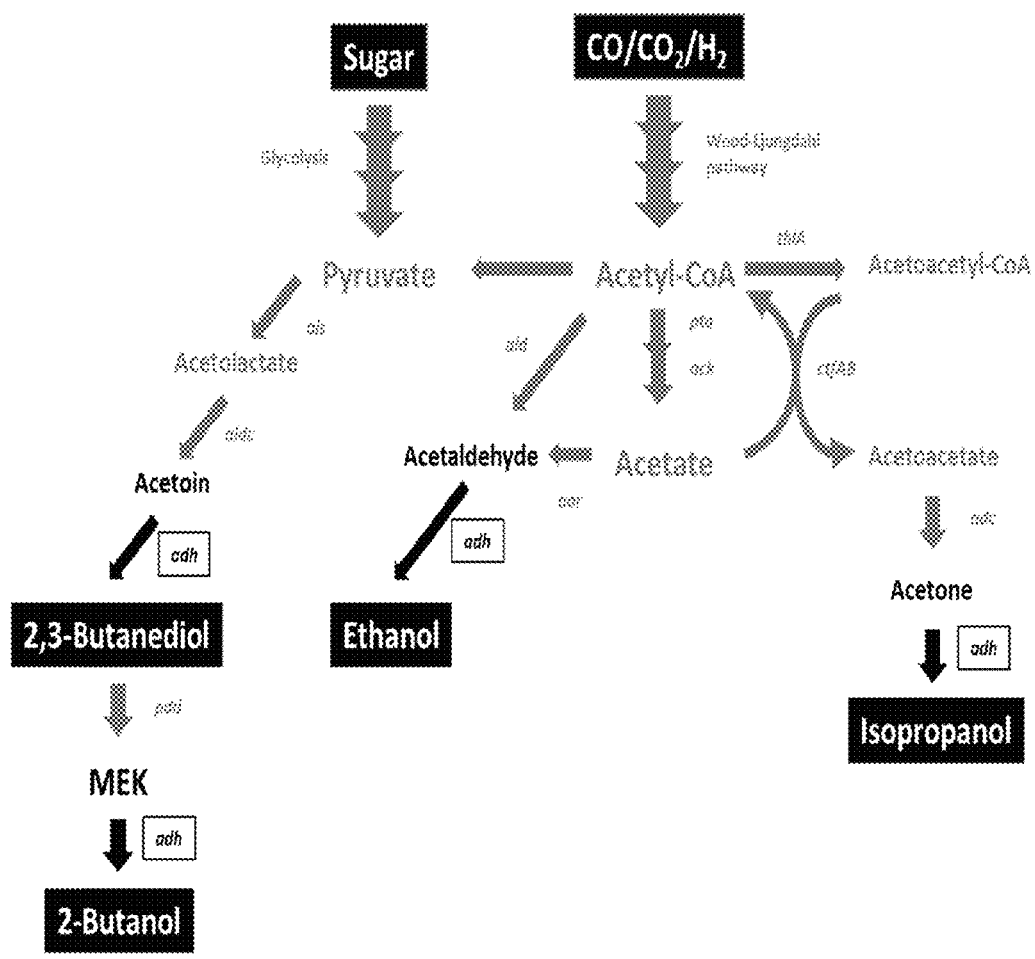
FIG. 14: Fermentation pathways to Isopropanol, 2,3-butanediol, 2-butanol and ethanol and role of the alcohol dehydrogenase (adh). Other reactions: acetolactate synthase (als), acetolactate decarboxylase (aldc), diol dehydratase (pdd), aldehyde dehydrogenase (ald), aldehyde:ferredoxin oxidoreductase (aor), phosphotransacetylase (pta), acetate kinase (ack), thiolase (thlA), CoA transferase (ctfAB), acetoacetate decarboxylase (adc).

Afterwards, kinetics for the purified wild-type enzyme (FIG. 12) of *C. autoethanogenum* DSM10061 were determined as baseline to evaluate mutated enzymes with substitutions (FIG. 9). Activity could be detected with ketones (acetone, MEK, acetoin) and aldehydes (acetaldehyde) which are important in several fermentation pathways (FIG. 14).

Subsequently, generated mutant alcohol dehydrogenases were assayed and compared with the wild-type enzyme. The Ser199Glu mutant could not be assayed, as there was no soluble protein. Assays of the crude cell lysate showed no ADH activity. While soluble, the Arg200Gln mutant also showed no detectable activity. Unsurprisingly, the mutant that combines these two, Ser199Glu+Arg200Gln, was also inactive. Of the three remaining proteins, the activity of Arg200Glu was only measurable when substrate concentrations were increased 5-fold (to 15 mM) and enzyme concentration was increased 6-fold (to 180 nM).

Figure 3:
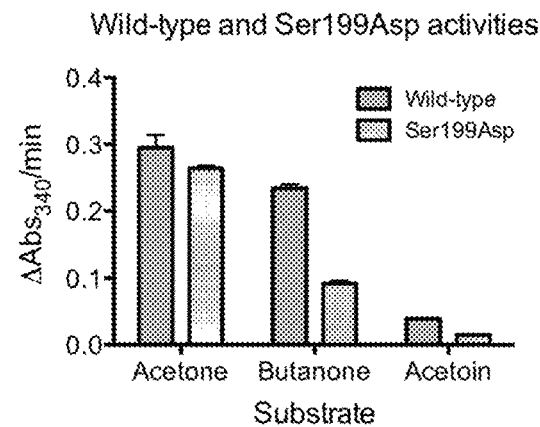
FIG. 3: shows the activity of wild-type protein and the Ser199Asp mutant. The Ser199Asp mutant was nearly as active as wild-type with acetone.
Figure 4:
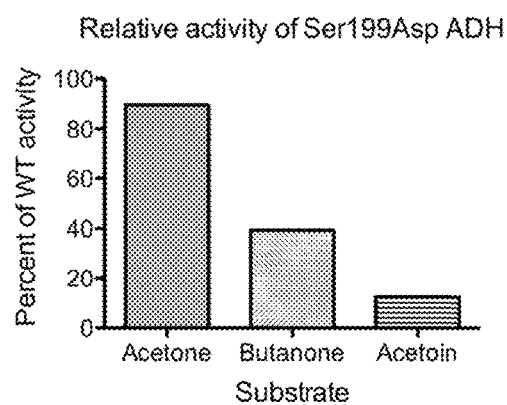
FIG. 4: shows the relative activity of the Ser199Asp mutant.

On the other hand, the Ser199Asp mutant was nearly as active as wild-type with acetone (FIG. 3). Most interestingly, the Ser199Asp mutant is more specific for acetone (FIG. 4). This indicates that replacing wild-type ADH with the Ser199Asp mutant may lead to increased isopropanol production. This mutant was the basis for further substitutions as described in Example 2.

Example 2

Change of Substrate and Co-Factor Specificity with Multiple Amino Acid Substitutions Based on the results from Example 1, the inventors generated and studied the activity of a further 8 alcohol dehydrogenase mutants with 1 to 4 amino acid substitutions:

| Name | Mutation(s) |
| --- | --- |
| Mutant 2 | S199E |
| Mutant 7 | G198D, S199V, P201E |
| Mutant 8 | G198E, S199V, P201E |
| Mutant 9 | G198D, S199L, P201E |
| Mutant 10 | G198D, S199V, P201E, Y218F |
| Mutant 11 | G198D, S199V, P201E, Y218A |
| Mutant 12 | G198D, S199D, P201E |
| Mutant 13 | Y218A |

Materials
Primers

TABLE 5

Oligonucleotides used for Quikchange mutagenesis.

| Primer name | Primer sequence (5'-3') | SEQ ID No. |
| --- | --- | --- |
| Mutant8_for | GCATTATTGGCGTTGAGGTTCGTGAGGTCTGCG | 23 |
| Mutant8_rev | CGCAGACCTCACGAACCTCAACGCCAATAATGC | 24 |
| Mutant9_for | GGGTCGCATTATTGGCGTTGATCTTCGTGAGGTCT | 25 |
| Mutant9_rev | AGACCTCACGAAGATCAACGCCAATAATGCGACCC | 26 |
| Mutant10_for | CCACGGACATCGTCAATTTCAAAAATGGCGACATTGT | 27 |
| Mutant10_rev | ACAATGTCGCCATTTTTGAAATTGACGATGTCCGTGG | 28 |
| Mutant11_for | GTGCCACGGACATCGTCAATGCCAAAAATGGCGACATTGTTG | 29 |
| Mutant11_rev | CAACAATGTCGCCATTTTTGGCATTGACGATGTCCGTGGCAC | 30 |
| Mutant12_for | CATTATTGGCGTTGATGATCGTGAGGTCTGCGTCG | 31 |
| Mutant12_rev | CGACGCAGACCTCACGATCATCAACGCCAATAATG | 32 |
| Mutant13_for | ATGGAGCAACTGATATTGTAAATGCTAAAAATGGTGATATAGTTGAAC | 33 |
| Mutant13_rev | GTTCAACTATATCACCATTTTTAGCATTTACAATATCAGTTGCTCCAT | 34 |

Plasmids

The gene sequence for Mutant 7 was synthesized by DNA 2.0. The sequence was codon optimized for expression of the protein in E. coli. The synthesized gene was provided in the plasmid pJ201. This sequence included HindIII and KpnI restriction sites for subcloning the Mutant 7 ADH gene into the expression vector pBAD(KpnI)-ADH.

Methods
Construction of the Expression Plasmid for Mutant 7

The pBAD backbone was prepared by digesting pBAD (KpnI)-ADH with the restriction enzymes KpnI-HF and HindIII-HF.

The Mutant 7 gene was similarly digested from the pJ201 vector with the restriction enzymes Kpn-HF and HindIII-HF.

The digested products were separated on a 1% agarose gel stained with SYBRsafe (Invitrogen). The bands corresponding to the digested vector and insert were excised and the DNA was recovered using a gel clean-up kit (Omega Bio-Tek).

The purified insert and vector DNA were ligated using a 3:1 molar ratio of insert to vector, using T4 DNA ligase (NEB) according to the manufacturer's standard protocol.

The ligation mixture was used to transform E. coli MC1061 cells by electroporation. Aliquots of the transformed cells were spread on LB-ampicillin and incubated at 37° C. overnight. A single colony was picked. The resulting expression plasmid was purified, and the sequence of the Mutant 7 gene was confirmed by DNA sequencing. A freezer stock was made of the successful clone.

Quikchange Mutagenesis of ADH

The template DNA used for the construction of Mutants 8, 9, 10, 11 and 12 was pBAD(KpnI)-Mutant 7 ADH. The template DNA used for the construction of Mutant 13 was pBAD(KpnI)-ADH. Aside from the different template DNA, and the corresponding mutagenic primers, the protocol for constructing Mutants 8-13 was the same. Each mutant was constructed using the Quikchange II Site-Directed Mutagenesis Kit from Stratagene, using their standard recommended protocol. The forward and reverse primers used for the construction of each mutant are listed in Table 5.

The products of the Quikchange mutagenesis reaction were used to transform chemically-competent E. coli XL1-Blue cells by heat shock. Single colonies were picked. The resulting expression plasmids were purified, and the sequence of each mutant gene was confirmed by DNA sequencing. A freezer stock was made of each successful clone.

Protein Expression and Purification

The expression vectors for Mutants 2, 7, 10, 11 were used to transform E. coli LMG194 that had previously been transformed with plasmid pGro7 (Takara Bio, Inc.). This plasmid facilitates arabinose-inducible expression of the GroEL/ES chaperone proteins. The expression vector for Mutant 13 was used to transform E. coli LMG194.

Expression of each ADH mutant was induced in mid-log phase cultures ($OD_{600}$ z 0.5), by adding L-arabinose to a final concentration of 0.2% (w/v). The cultures were incubated at 28° C. for an additional 5 h. Cells were harvested by centrifugation and the pellets were stored at −80° C. Each pellet was resuspended in 10 mL of lysis buffer (50 mM potassium phosphate, 300 mM NaCl, pH 7.0). Protease inhibitor cocktail (150 µL), Benzonase nuclease (37.5 U) and lysozyme (0.2 mg·mL$^{-1}$, final concentration) were added. After 20 minutes incubation at 4° C., cells were lysed by sonication on ice, and the lysates were clarified by centrifugation (21,000 g, 4° C., 30 minutes). The clarified lysate was mixed with 500 µL Talon metal affinity resin (50% w/v slurry) and the mixture was gently agitated at 4° C. for 1 h to allow the His$_6$-tagged ADH protein to bind the resin. The resin was washed multiple times with lysis buffer, before being transferred to a gravity flow column. For the purification of Mutants 7, 8, 9, 10 and 12, 5 mM ATP/MgCl$_2$ was included in this wash step to facilitate removal of chaperone proteins. After further washes with 10 bed volumes of lysis buffer containing 5 mM imidazole and 10 mM imidazole, respectively, each purified protein was eluted with 5 bed volumes of elution buffer (50 mM potassium phosphate, 300 mM NaCl, 150 mM imidazole, pH 7.0). Amicon Ultra centrifugal filter units (10 kDa molecular weight cut-off; Merck Millipore, Billerica, Mass.) were used to exchange the purified protein into storage buffer (50 mM potassium phosphate, 150 mM NaCl, 10% (v/v) glycerol, pH 7.5). Aggregates were removed by filtration through a sterile 0.22 m filter (Millex-GV; Millipore). Each protein was judged to be >95% pure by SDS-PAGE. ADH concentrations were quantified by measuring A$_{280}$ (using extinction coefficients calculated according to (Pace, Vajdos et al. 1995). Aliquots of the purified protein were stored at −80° C. Activity assays verified that these storage conditions, combined with a freeze/thaw cycle, did not lead to any loss of activity.

As shown in FIG. 5, Mutants 2, 7 and 11 were all highly soluble when expressed in *E. coli* with the pGro7 plasmid. The yield soluble protein for Mutant 10 was lower than the other variants. Mutants 8, 9 and 12 were completely insoluble, even when co-expressed with pGro7. Mutant 13 was highly soluble, and could be produced in high quantities under the same conditions as the wild-type ADH protein.

Activity Assays

Wild-type and mutant ADH activities were measured using a spectrophotometric assay, based on a method described previously (Ismaiel, Zhu et al. 1993). Activity was quantified by monitoring the decrease in absorbance at 340 nm associated with the oxidation of NADPH or NADH ($\epsilon_{340}$=6,220 M$^{-1}$·cm$^{-1}$). Steady-state kinetic parameters were measured at 25° C. using a Cary 100 UV-Vis spectrophotometer with a Peltier temperature controller. The standard assay mixture contained 50 mM Tris-HCl, 1 mM DTT, pH 7.5 with either cofactor (NADPH or NADH) present at 0.2 mM. Initial reaction rates were measured with a substrate concentration of 5 mM. Measurements were made in triplicate and corrected for background. Co-factors NADH and NADPH and substrates acetone, acetoin, MEK were sourced from Sigma-Aldrich. D-Acetoin was purified as described below as there is no commercial source.

Overall, Mutant 11 has the highest activity using NADH as the cofactor (FIG. 6). The cofactor usage for Mutant 11 has completely switched (compared to wild-type ADH); Mutant 11 had no detectable activity with NADPH.

Mutant 11 has four mutations (G198D, S199V, P201E, Y218A). All four mutations are required for the observed switch in cofactor usage. The addition of the Y218A mutation was required for activity with NADH, but this mutation alone (i.e. Mutant 13) had no effect on cofactor preference. This could have important advantages in fermentation pathways to Isopropnaol, 2,3-butanediol, 2-butanol, and ethanol as shown in FIG. 14

Figure 7:
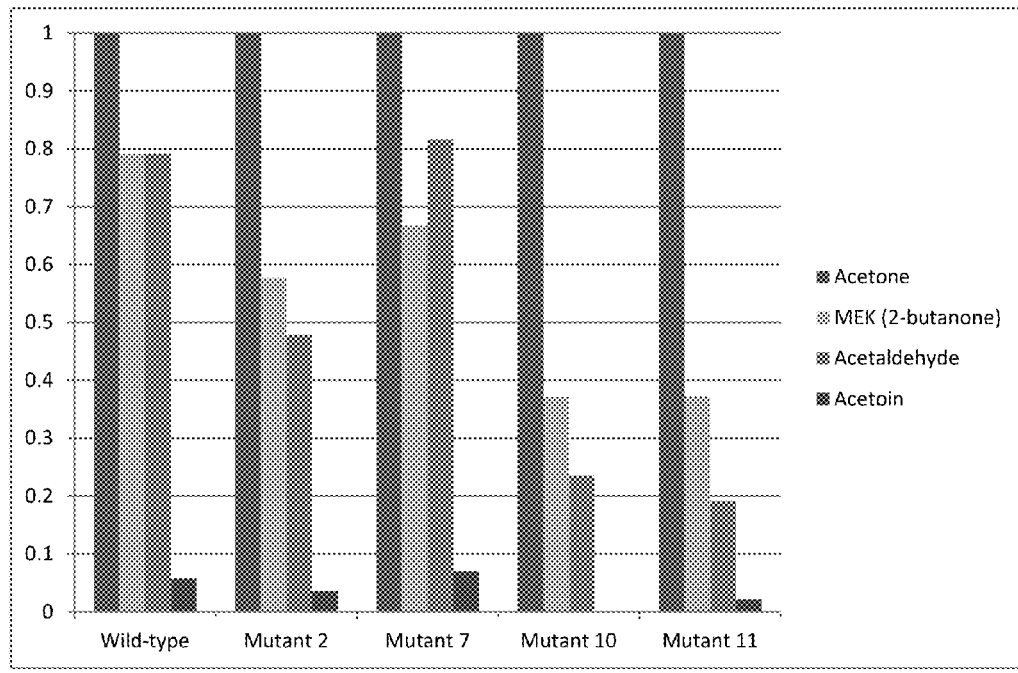
FIG. 7: shows the specific activity of the wild-type and mutant ADH enzymes with different substrates normalized to acetone (acetone set=1). For each enzyme, the preferred cofactor was used (i.e. NADPH for wild-type ADH, Mutant 2 and Mutant 7; NADH for Mutant 10 and Mutant 11).

As shown in FIG. 7 some mutants are also more specific for acetone, over either a larger substrate (acetoin and MEK) or a smaller substrate (acetaldehyde). All mutants (2, 7, 10 and 11) have an increased substrate specificity of acetone over MEK. Mutants 2, 10 and 11 have an increased substrate specificity of acetone over acetaldehyde and over acetoin.

Figure 8:
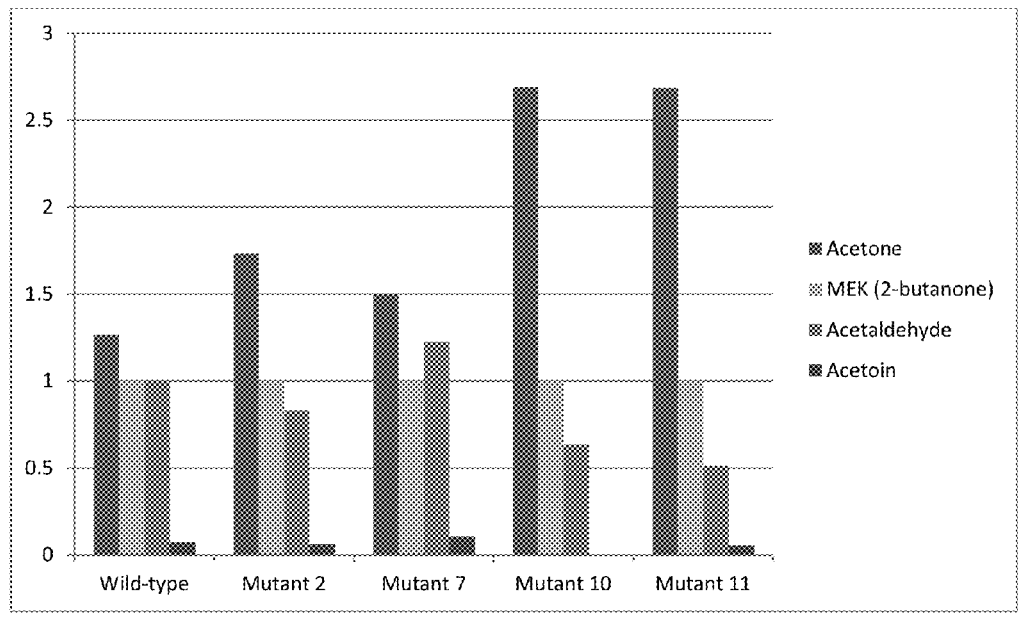
FIG. 8: shows the specific activity of the wild-type and mutant ADH enzymes with different substrates normalized to MEK (2-butanone) (MEK set=1). For each enzyme, the preferred cofactor was used (i.e. NADPH for wild-type ADH, Mutant 2 and Mutant 7; NADH for Mutant 10 and Mutant 11).

As shown in FIG. 8 some mutants are also more specific for MEK, over either a larger substrate (acetoin) or a smaller substrate (acetaldehyde). Mutant 2, 10 and 11 have an increased substrate specificity of MEK over acetaldehyde and over acetoin.

As shown in FIG. 9 some mutants are also more specific for acetaldehyde over a larger substrate (acetone, acetoin and MEK). Mutant 7 has an increased substrate specificity of acetaldehyde over acetone and over MEK. Mutants 2, 7 and 10 have an increased substrate specificity of acetaldehyde over acetoin.

Figure 10:
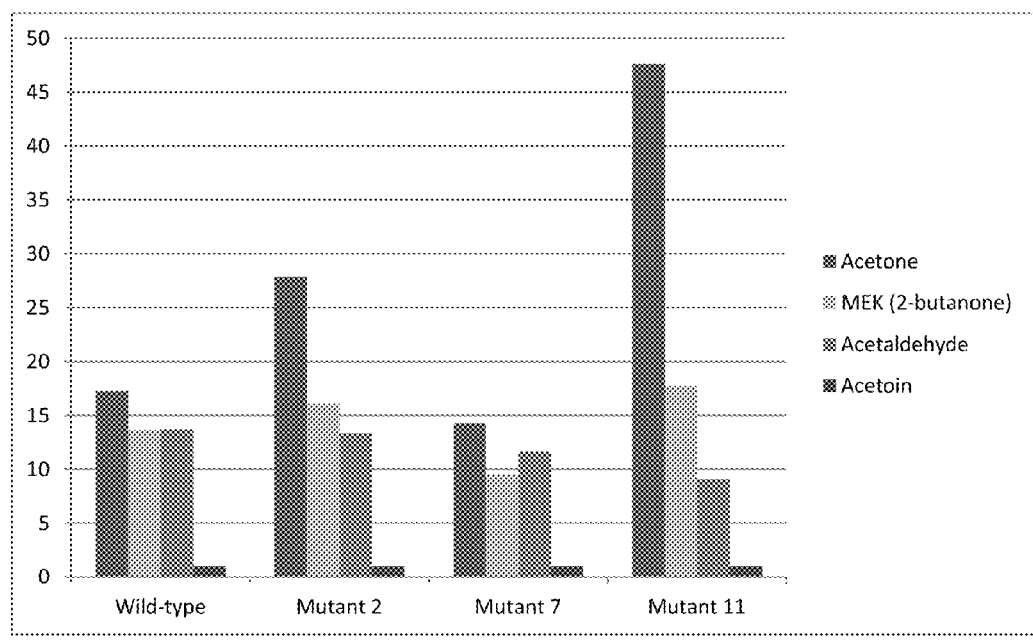
FIG. 10: shows the specific activity of the wild-type and mutant ADH enzymes with different substrates normalized to acetoin (acetoin set=1). For each enzyme, the preferred cofactor was used (i.e. NADPH for wild-type ADH, Mutant 2 and Mutant 7; NADH for Mutant 10 and Mutant 11).

As shown in FIG. 10 some mutants are also more specific for acetoin over a smaller substrate (acetone, acetoin and MEK). Mutant 7 has an increased substrate specificity of acetoin over acetone and over MEK. Mutants 7 and 11 have an increased substrate specificity of acetoin over acetaldehyde. Mutant 10 lost the activity with acetoin, while still having activity with the other substrates acetone, MEK and acetaldehyde.

In summary, the results, as depicted in FIGS. 7-10, show that:

mutant 2 has an increased substrate specificity for 1) acetone over MEK, acetaldehyde and acetoin, 2) MEK over acetaldehyde and acetoin;

mutant 7 has an increased substrate specificity for 1) acetone over MEK, 2) acetaldehyde over MEK, acetone and acetoin, 3) acetoin over acetoneand MEK;

mutant 11 has an increased substrate specificity for 1) acetone over MEK, acetaldehyde and acetoin, 2) MEK over acetaldehyde and acetoin, 3) acetoin over acetaldehyde; and, mutant 10 has an increased substrate specificity for 1) acetone over MEK, acetaldehyde and acetoin, and 2) MEK over acetaldehyde and acetoin, 3) acetalydehyde over acetoin. This could have important advantages in fermentation pathways to Isopropnaol, 2,3-butanediol, 2-butanol, and ethanol shown in FIG. 14.

Purification of D-acetoin

Enantioselective synthesis of D-acetoin (or (S)-acetoin):: D-Acetoin was synthesized as described via the regioselectively-controlled monooxidation of D-(−)-2,3-butanediol (D'Accoloti et al. 1993 *J. Org. Chem.* 58: 3600-1) The requisite dimethyldioxirane (DMDO)-acetone solution was freshly prepared according to a modification of a previously reported procedure and subsequently titrated by iodometry.

Generation of DMDO-acetone solution: A 1000 mL 3-neck round bottom flask was fitted with a gas adaptor and a double distillation head, to which was attached a vacuum adapted receiver. The final joint was stoppered and intended for reagent additions. A round-bottom flask was fastened to the receiving end and cooled to −78° C. in an acetone-dry ice bath. In line with the vacuum was a Buchi® cold finger condenser cooled to −20° C. using salted-ice, followed by connection to a −196° C. liquid nitrogen cold finger trap.

The reaction vessel was charged with a large oval stirring bar, water (220 mL), acetone (160 mL) and sodium bicarbonate (120.063 g). Vigorous stirring was initiated at 0° C. whilst purging with nitrogen, which was continued during addition of solid oxone (250.047 g) in 5 portions at 3 minute intervals. Strong effervescence was exhibited and the rate of oxone addition was controlled to manage this accordingly. After addition of the second portion of oxone, the colourless solution above the white slurry took on a pink colour. Stirring was continued for 15 minutes upon complete addition of oxone. At the subsidence of effervescence, a slight vacuum (900 mbar) was applied, which was slowly increased to about 450 mbar whilst monitoring effervescence. During progressive application of vacuum, a pale yellow solution collected in the cooled receiver. Once about 100 mL of DMDO-acetone solution was collected the reaction was quenched with saturated $Na_2S_2O_3$ solution and the product brought to room temperature.

Iodometric titration of DMDO: The freshly distilled solution of DMDO in acetone (1.00 mL) was pipetted into an acetic acid-acetone solution (2 mL, 3:2). Saturated aqueous potassium iodide solution (2.0 mL) was then added, together with dry ice to de-aerate the solution. This was allowed to mix whilst stored in the dark at room temperature for 10 minutes. The mixture was diluted with water (5 mL) and titrated against aqueous $Na_2S_2O_3$ (0.00099 mol/L) solution using 1% starch solution as the endpoint indicator, yielding a concentration of 29.9 mM. The flask was then, sealed and stored at −18° C.

DMDO Oxidation of (R,R)-2,3-butanediol.

The monooxidation of D-(−)-2,3-butanediol to (R)-3-hydroxybutanone was conducted as per method reported in the literature (D'Accoloti et al. 1993 *J. Org. Chem.* 58: 3600-1).

Example 3

Preferential Production of 2,3-butanediol Over Ethanol in Carboxydotrophes Using Optimized Alcohol Dehydrogenase Carboxydotropic organism *C. autoethanogenum* was shown to produce both ethanol and 2,3-butanediol from CO (Köpke et al., 2011) (FIG. 14). As demonstrated in example 1, an alcohol dehydrogenase is present in *C. autoethanogenum* that catalyses the last step in both the ethanol and the 2,3-butanediol pathway, the reactions of acetaldehyde to ethanol respectively acetoin to 2,3-butanediol (FIG. 14). The activity of this wild-type enzyme with acetaldehyde is higher than with acetoin (FIG. 12), which leads to ethanol being the dominant product over 2,3-butanediol in fermentations with *C. autoethanogenum* DSM 10061 (Köpke et al., 2011). In example 2, an alcohol dehydrogenase mutant (mutant 7) was generated with amino acid substitutions G198E, S199V, P201E that has an improved substrate specificity for acetoin over acetaldehyde (FIG. 7). This enzyme that preferentially uses acetoin over acetaldehyde compared to the wild-type enzyme can be used to increase the 2,3-butanediol production over ethanol production compared to the wild-type strain.

The gene (Seq. ID 41) of a mutant alcohol dehydrogenase is cloned into a pMTL85353 shuttle vector (Heap, Pennington, Cartman, & Minton, 2009) carrying a ferredoxin promoter using sites NdeI and EcoRI. The construct is then methylated and transformed into *C. autoethanogenum* by electroporation as described (US 2012/0252083, WO/2012/115527). Thiamphenicol resistant colonies are picked and grown in 5 mL liquid media. The transformed culture is verified by PCR and a fermentation experiment is carried out. When comparing the metabolic end products to the wild-type of *C. autoethanogenum*, the strain carrying the mutant alcohol dehydrogenase will have an increased 2,3-butanediol:ethanol ratio.

In analogy to this, other acetogenic strains such as *C. ljungdahlii* can be modified with the alcohol dehydrogenase mutant, using the same plasmid. Electroporation has been described for several carboxydotrophic acetogens such as *C. ljungdahlii* (Köpke et al. 2010, Proc. Nat. Acad. Sci. U.S.A. 107: 13087-92; (Leang, Ueki, & Lovley, 2011) PCT/NZ2011/000203; WO2012/053905), *Acetobacterium woodii* (Straetz et al., 1994, Appl. Environ. Microbiol. 60:1033-37) and *Moorella thermoacetica* (Kita et al., 2012). *C. autoethanogenum*, *C. ljungdahlii* and other acetogenic strains are able to produce ethanol and 2,3-butanediol (Köpke et al., 2011). By expressing the mutant alcohol dehydrogenase, this ratio can be improved in favour of 2,3-butanediol.

Example 4

Preferential Production of Ethanol Over 2,3-butanediol in Carboxydotrophes Using Optimized Alcohol Dehydrogenase As described in example 3, *C. autoethanogenum* is able to produce both ethanol and 2,3-butanediol from CO (FIG. 14). For some processes it may however be favourable to produce only a single product in order to keep the costs (e.g separation) of the process low. Typically this can be achieved by inactivating an enzyme in the pathway of one of the pathways. However, in case of a multifunctional enzyme that catalyzes reaction in multiple pathways, this strategy can't be applied, which is the case for the alcohol dehydrogenase of *C. autoethanogenum* that catalyzes both the reduction of acetaldehyde to ethanol and acetoin to 2,3-butanediol. The current invention gives an alternative means to achieve, for example, production of ethanol with reduced levels or without 2,3-butanediol. In example 2, an alcohol dehydrogenase mutant (mutant 10) was generated with amino acid substitutions G198D, S199V, P201E, Y218F that lost the ability to reduce acetoin, but still has activity with acetaldehyde (FIG. 7). The gene (Seq. ID 47) of this mutant alcohol dehydrogenase is cloned into a vector along with the flanking regions of the alcohol dehydrogenase to allow a double homologous crossover integration (replacing the wild-type with the mutant alcohol dehydrogense). 1 kb 5' (Seq. ID. 55) and 3' (Seq. ID. 56) homology arms of SecAdh genes are PCR amplified using *C. autoethanogenum* DSM23693 genomic DNA. Primers Sec5f (attcatcctgcag-gACAGTTAAAAAGCATATCTAACAGT (SEQ ID 57))/Sec5r (gactgcggccgcTAAATATATAAGCAAATGTTGT-GCC (SEQ ID 58)) and Sec3f (atatgctagCGTATTTTTAATTGCGAACTTAAGA (SEQ ID 59))/Sec3r (gactggcgcgcCAGTTAAAGTTAGACATC-CGATTAT (SEQ ID 60)) are used to amplify the 5' and 3' homology arms, respectively. The two PCR products are cloned into pMTL85151 plasmids between the SbfI/NotI and NheI/AscI sites to get pMTL85151-SecAdh-KO. The vector is transformed as described above. Following selection on thiamphenicol plates the transformants are screened for swap out of the wild-type alcohol dehydrogenase with the mutant alcohol dehydrogenase using the primers SecOf (TTGGAATTTTAGCTGTAGATAACAA (SEQ ID 61)) and SecOr (TAAGTGATTTTCAATGGACTTTACT (SEQ ID 62)) that flank the homology arms. After sequencing conformation, a fermentation experiment is carried out, confirming production of ethanol with reduced or no 2,3- butanediol production. In *C. autoethanogenum*, a second enzyme with activity towards butanediol is present which can be knocked-out for complete removal of 2,3-butanediol production under certain conditions.

In analogy to this, other acetogenic 2,3-butanediol producing strains such as *C. ljungdahlii* and *C. ragsdalei* can be modified with the alcohol dehydrogenase mutant, using the same plasmid. Electroporation as well as a method for double homologous crossover has been described for *C. ljungdahlii* (Köpke et al. 2010, *Proc. Nat. Acad. Sci. U.S.A.* 107: 13087-92; (Leang et al., 2011).

Example 5

Production of Isopropanol in Carboxydotrophes Using Optimized Alcohol Dehydrogenase

*C. autoethanogenum* has been modified for isopropanol production from CO by introducing acetone biosynthesis genes, relying on the wild-type alcohol dehydrogenase (US 2012/0252083, WO/2012/115527). To improve the production, a highly acetone specific mutant alcohol dehydrogenase (mutant 11) with substitutions G198D, S199V, P201E, Y218A generated in example 2 can be introduced. The mutant alcohol dehydrogenase gene (Seq. ID 53) is cloned into acetone biosynthesis plasmid (Seq. ID 40) by SalI/XhoI restriction sites. The plasmid is then transformed in *C. autoethanogenum* as described above. Fermentation experiments with the transformed culture will show an increased isopropanol production in which all acetone is converted to isopropanol. In addition to having an increased specificity towards acetone, the organism will use NADPH and NADH for isopropanol synthesis, allowing to tap into both pools.

In analogy to this, other acetogenic strains such as *C. ljungdahlii* can be modified with the alcohol dehydrogenase mutant, using the same plasmid. Electroporation has been described for several carboxydotrophic acetogens as *C. ljungdahlii* (Köpke et al. 2010, Proc. Nat. Acad. Sci. U.S.A. 107: 13087-92; (Leang et al., 2011) PCT/NZ2011/000203; WO2012/053905), *Acetobacterium woodii* (Straetz et al., 1994, Appl. Environ. Microbiol. 60:1033-37) or *Moorella thermoacetica* (Kita et al., 2012). As *C. autoethanogenum*, *C. ljungdahlii* and other acetogenic strains are able to produce ethanol and 2,3-butanediol (Köpke et al., 2011). By expressing the mutant alcohol dehydrogenase, this ratio can be improved in favour of 2,3-butanediol.

Example 6

Production of Isopropanol in ABE Organism Using Optimized Alcohol Dehydrogenase

It has been shown that *C. acetobutylicum* can be metabolically engineered for isopropanol production using a secondary alcohol dehydrogenase from *C. beijerinckii*, but the reported results show only low isopropanol levels with residual acetone that hasen't been converted through to isopropanol [Lee et al, 2012: Metabolic engineering of *Clostridium acetobutylicum* ATCC824 for isopropanol-butanol-ethanol fermentation, *Appl. Environ. Microbiol.* 78: 1416-1423]. To improve this process an optimized alcohol dehydrogenase is required to overcome this limitation.

In example 2 an optimized mutant alcohol dehydrogenase (mutant 11) was generated with substitutions G198D, S199V, P201E, Y218A that has high specificity towards acetoin and is also able to use NADH, which is more abundant than NADPH in *C. acetobutylicum*. The mutant alcohol dehydrogenase gene (Seq. ID 53) is cloned into a pMTL85354 shuttle vector (Heap et al., 2009) carrying the strong *C. acetobutylicum* thiolase promoter using sites NdeI and EcoRI. The plasmid is then in vivo methylated using a *Bacillus subtilis* phage methyltrasnferase and transformed in *C. acetobutylicum* as described (Mermelstein & Papoutsakis, 1993). In a fermentation carried out with the transformed culture all acetoin is converted to isopropanol with high specificity.

Example 7

Production of Isopropanol in *E. Coli* Using Optimized Alcohol Dehydrogenase

*E. coli* has been a target for isopropanol production in several studies [Hanai T et al (2007) Engineered synthetic pathway for isopropanol production in *Escherichia coli*. *Applied and environmental microbiology* 73:7814-8; Inokuma K et al (2010) Improvement of isopropanol production by metabolically engineered *Escherichia coli* using gas stripping. *Journal of bioscience and bioengineering* 110: 696-701; Jojima T et al (2008) Production of isopropanol by metabolically engineered *Escherichia coli*. *Applied microbiology and biotechnology* 77:1219-24]. However all studies use the very same non-optimized alcohol dehydrogenase from *C. beijerinckii*, limiting isopropanol production due to the enzyme's low specificity and NADPH dependency. This becomes evident as in all studies acetone accumulates as by-product as it is not effectively enough reduced to isopropanol. In *E. coli*, the pool of NADH pool is several times bigger than the NADPH pool (Bennett & San, 2009).

In example 2 an optimized mutant alcohol dehydrogenase (mutant 11) was generated with substitutions G198D, S199V, P201E, Y218A that has high specificity towards acetoin and is also able to use NADH. *E. coli* can be engineered to include this mutant alcohol dehydrogenase using standard techniques used in the art. The recombinant *E. coli* will have increased isopropanol production compared to a wild type organism.

Example 8

Production of 2-butanol in Yeast *S. Cerevisiae* Using Optimized Alcohol Dehydrogenase Some strains of yeast *Saccharomyces cerevisiae* are able to produce high levels of acetoin (Romano, Suzzi, Mortimer, & Polsinelli, 1995) beside ethanol. D-Acetoin (or (S)-Acetoin) can be converted to meso-2,3-butanediol by action of the alcohol dehydrogenase of *C. autoethanogenum* described in example 1. Conversion of meso-2,3-Butanediol to MEK has been described with diol dehydratase enzyme of for example *A. aerogenes* (Toraya T, Shirakashi T, Kosuga T, 1976) or *Klebsiella pneumonia* (Bachovchin, Eagar, Moore, & Richards, 1977). MEK can then again be converted to 2-butanol with the alcohol dehydrogenase of *C. autoethanogenum* described in example 1 (FIG. 14). As the alcohol dehydrogenase however also has activity towards ethanol it is desirable to have an enzyme with only low activity with acetaldehyde to ethanol but relatively higher activity with acetoin to 2,3-butanediol and MEK to 2-butanol. Mutant 11 of example 2 has exactly these properties and uses NADH as co-factor which is favourable in yeasts.

Codon optimized gene for Mutant 11 (Seq. ID 50) and codon optimized genes for diol dehydratase from *Klebsiella pneumonia* (YP_002236782; YP_002236783;

YP_002236784) are cloned under inducible yeast promoter GAL 1/10 into an appropriate vector as described (Steen et al., 2008). Transformation of all *S. cerevisiae* strains is performed using the lithium acetate method as described (Gietz R W: RA Guide to Yeast Genetics and Molecular and Cell Biology. Part B. San Diego, Calif.: Academic Press Inc; 2002:87-96). After successful transformation and verification a fermentation with *S. cerevisiae* in rich YPD medium at 30° C. is carried out with 2-butanol and low levels of ethanol as product.

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

REFERENCES

Abrini, J., Naveau, H., & Nyns, E. J. (1994). *Clostridium autoethanogenum*, sp. nov., an anaerobic bacterium that produces ethanol from carbon monoxide. *Archives of microbiology*, 161(4), 345-351. Retrieved from http://www.springerlink.com/index/v143151w30423660.pdf Bachovchin, W. W., Eagar, R. G., Moore, K. W., & Richards, J. H. (1977). Mechanism of action of adenosylcobalamin: glycerol and other substrate analogues as substrates and inactivators for propanediol dehydratase—kinetics, stereospecificity, and mechanism. *Biochemistry*, 16(6), 1082-92. Retrieved from http://www.ncbi.nlm.nih.gov/pubmed/321014

Bennett, G. N., & San, K. (2009). Systems Biology and Biotechnology of *Escherichia coli*. In S. Y. Lee (Ed.), *Systems Biology and Biotechnology of Escherichia coli* (pp. 351-376). Dordrecht: Springer Netherlands. doi: 10.1007/978-1-4020-9394-4

Berzin, V., Kiriukhin, M., & Tyurin, M. (2012). Selective production of acetone during continuous synthesis gas fermentation by engineered biocatalyst *Clostridium* sp. MAceT113. *Letters in applied microbiology*. doi:10.1111/j. 1472-765X.2012.03272.x Collins, M. D., Lawson, P. A., Willems, A., Cordoba, J. J., Fernandez-Garayzabal, J., Garcia, P., Cai, J., et al. (1994). The phylogeny of the genus *Clostridium*: proposal of five new genera and eleven new species combinations. *International journal of systematic bacteriology*, 44(4), 812-26. Retrieved from http://www.ncbi.nlm.nih.gov/pubmed/7981107

Drake, H. L., Küsel, K., Matthies, C., Wood, H. G., & Ljungdahl, L. G. (2006). Acetogenic Prokaryotes. In M. Dworkin, S. Falkow, E. Rosenberg, K.-H. Schleifer, & E. Stackebrandt (Eds.), *The Prokaryotes* (3rd Editio., pp. 354-420). New York, N.Y.: Springer. doi:10.1007/0-387-30742-7

Heap, J. T., Pennington, O. J., Cartman, S. T., & Minton, N. P. (2009). A modular system for *Clostridium* shuttle plasmids. *Journal of microbiological methods*, 78(1), 79-85. doi:10.1016/j.mimet. 2009.05.004

Ismaiel, a a, Zhu, C. X., Colby, G. D., & Chen, J. S. (1993). Purification and characterization of a primary-secondary alcohol dehydrogenase from two strains of *Clostridium beijerinckii*. Journal of bacteriology, 175(16), 5097-105. Retrieved from http://www.pubmedcentral.nih.gov/articlerender.fcgi?artid=204976&tool=pmcentrez&rendertype=abs tract Keis, S., Shaheen, R., & Jones, D. T. (2001). Emended descriptions of *Clostridium acetobutylicum* and *Clostridium beijerinckii*, and descriptions of *Clostridium saccharoperbutylacetonicum* sp. nov. and. *International journal of systematic and evolutionary microbiology*, 2095-2103.

Kita, A., Iwasaki, Y., Sakai, S., Okuto, S., Takaoka, K., Suzuki, T., Yano, S., et al. (2012). Development of genetic transformation and heterologous expression system in carboxydotrophic thermophilic acetogen *Moorella thermoacetica*. *Journal of Bioscience and Bioengineering*, xx(xx), 1-6. doi:10.1016/j.jbiosc. 2012.10.013

Köpke, M., & Dürre, P. (2011). Biochemical production of biobutanol. In R. Luque, J. Campelo, & J. H. Clark (Eds.), *Handbook of biofuels production: processes and technologies* (pp. 221-257). Camebridge, UK: Woodhead Publishing Ltd. Retrieved from http://www.woodhead-publishing.com/en/book.aspx?bookID=1643

Köpke, M., Held, C., Hujer, S., Liesegang, H., Wiezer, A., Wollherr, A., Ehrenreich, A., et al. (2010). *Clostridium ljungdahlii* represents a microbial production platform based on syngas. *Proceedings of the National Academy of Sciences of the United States of America*, 107(29), 13087-92. doi: 10.1073/pnas. 1004716107

Köpke, M., Mihalcea, C., Liew, F., Tizard, J. H., Ali, M. S., Conolly, J. J., Al-Sinawi, B., et al. (2011). 2,3-Butanediol Production By Acetogenic Bacteria, an Alternative Route To Chemical Synthesis, Using Industrial Waste Gas. *Applied and environmental microbiology*, 77(15), 5467-75. doi:10.1128/AEM. 00355-11

Leang, C., Ueki, T., & Lovley, D. R. (2011). *Development of Genetic Systems for Clostridium* ljungdahlii. Poster.

Mermelstein, L. D., & Papoutsakis, E. T. (1993). In vivo methylation in *Escherichia coli* by the *Bacillus subtilis* phage phi 3T I methyltransferase to protect plasmids from restriction upon transformation of *Clostridium acetobutylicum* ATCC 824. *Applied and environmental microbiology*, 59(4), 1077-81. Retrieved from http://www.pubmedcentral.nih.gov/articlerender.fcgi?artid=202241&tool=pmcentrez&rendertype=abs tract Perez, J. M., Richter, H., Loftus, S. E., & Angenent, L. T. (2012). Biocatalytic reduction of short-chain carboxylic acids into their corresponding alcohols with syngas fermentation. *Biotechnology and bioengineering*, 1-30. doi: 10.1002/bit. 24786

Romano, P., Suzzi, G., Mortimer, R., & Polsinelli, M. (1995). Production of high levels of acetoin in *Saccharomyces cerevisiae* wine yeasts is a recessive trait. *The Journal of applied bacteriology*, 78(2), 169-74. Retrieved from http://www.ncbi.nlm.nih.gov/pubmed/7698951

Steen, E. J., Chan, R., Prasad, N., Myers, S., Petzold, C. J., Redding, A., Ouellet, M., et al. (2008). Metabolic engineering of *Saccharomyces cerevisiae* for the production of n-butanol. *Microbial cell factories*, 7, 36. doi:10.1186/1475-2859-7-36

Tanner, R. S., Miller, L. M., & Yang, D. (1993). *Clostridium ljungdahlii* sp. nov., an acetogenic species in clostridial rRNA homology group I. *International journal of systematic bacteriology*, 43(2), 232. Retrieved from http://ijs.sgmjournals.org/content/43/2/232.short Toraya T, Shirakashi T, Kosuga T, F. S. (1976). Substrate Specificity Of Coenzyme B12-Dependent Diol Dehydratase. *Biochemical and biophysical research communications*, 69(2), 475-480.

Tyurin, M., & Kiriukhin, M. (2012). Electrofusion of cells of Acetogen *Clostridium* sp. MT 351 with erm (B) or cat in the chromosome. *Journal of Biotech*, 1-12. Retrieved from http://lu38361.web.officelive.com/Documents/2012v4p 1-12.pdf Ismaiel, A. A., C. X. Zhu, et al. (1993). "Purification and characterization of a primary-secondary alcohol dehydrogenase from two strains of *Clostridium beijerinckii*." J. Bacteriol. 175(16): 5097-5105.

Pace, C. N., F. Vajdos, et al. (1995). How to measure and predict the molar absorption coefficient of a protein. Protein Sci. 4(11): 2411-2423.

The invention claimed is:

1. An alcohol dehydrogenase comprising the amino acid sequence of SEQ ID NO: 36, with the exception of at least one amino acid substitution selected from the group consisting of Gly198Ile, Gly198Val, Ser199Asp, Ser199Glu, Ser199Leu, Ser199Val, Arg200Glu, Pro201 Asp, Pro201Glu, Tyr218Ala, Tyr218Gly, Tyr218Ser, and Tyr218Val, wherein amino acid numbering is relative to the amino acid sequence of SEQ ID NO: 36, and wherein said alcohol dehydrogenase has alcohol dehydrogenase activity.

2. The alcohol dehydrogenase of claim 1, wherein said alcohol dehydrogenase comprises:
 a Ser199Asp amino acid substitution;
 a Ser199Glu amino acid substitution;
 a combination of said amino acid substitutions Gly198Asp, Ser199Val, and Pro201Glu;
 a combination of said amino acid substitutions Gly198Asp, Ser199Val, Pro201Glu, and Tyr218Ala;
 a combination of said amino acid substitutions Gly198Asp, Ser199Val, Pro201Glu, and Tyr218Phe;
 a combination of said amino acid substitutions Gly198Asp, Ser199Val, Pro201Glu, and Tyr218Val;
 a combination of said amino acid substitutions Gly198Asp, Ser199Val, Pro201Glu, and Tyr218Gy; or
 a combination of said amino acid substitutions Gly198Asp, Ser199Val, Pro201Glu, and Tyr218Ser.

3. The alcohol dehydrogenase of claim 1, wherein said alcohol dehydrogenase has increased specificity for at least one first substrate over at least one second substrate wherein:
 said first substrate is acetone and said second substrate is methyl ethyl ketone (MEK);
 said first substrate is acetone and said second substrate is acetaldehyde;
 said first substrate is acetone and said second substrate is acetoin;
 said first substrate is MEK and said second substrate is acetaldehyde;
 said first substrate is MEK and said second substrate is acetoin;
 said first substrate is acetoin and said second substrate is acetone;
 said first substrate is acetoin and said second substrate is MEK;
 said first substrate is acetoin and said second substrate is acetaldehyde;

said first substrate is acetaldehyde and said second substrate is acetone;
said first substrate is acetaldehyde and said second substrate is acetoin; or
said first substrate is acetaldehyde and said second substrate is MEK.

4. The alcohol dehydrogenase of claim 1, wherein said alcohol dehydrogenase uses NADH as a co-factor or has increased specificity for an NADH co-factor over an NADPH co-factor.

5. A microorganism comprising said alcohol dehydrogenase of claim 1.

6. The microorganism of claim 5, wherein said alcohol dehydrogenase comprises:
a Ser199Asp amino acid substitution;
a Ser199Glu amino acid substitution;
a combination of said amino acid substitutions Gly198Asp, Ser199Val, and Pro201Glu;
a combination of said amino acid substitutions Gly198Asp, Ser199Val, Pro201Glu, and Tyr218Ala;
a combination of said amino acid substitutions Gly198Asp, Ser199Val, Pro201Glu, and Tyr218Phe;
a combination of said amino acid substitutions Gly198Asp, Ser199Val, Pro201Glu, and Tyr218Val;
a combination of said amino acid substitutions Gly198Asp, Ser199Val, Pro201Glu, and Tyr218Gy; or
a combination of said amino acid substitutions Gly198Asp, Ser199Val, Pro201Glu, and Tyr218Ser.

7. The microorganism of claim 5, wherein said alcohol dehydrogenase has increased specificity for at least one first substrate over at least one second substrate wherein:
said first substrate is acetone and said second substrate is methyl ethyl ketone (MEK);
said first substrate is acetone and said second substrate is acetaldehyde;
said first substrate is acetone and said second substrate is acetoin;
said first substrate is MEK and said second substrate is acetaldehyde;
said first substrate is MEK and said second substrate is acetoin;
said first substrate is acetoin and said second substrate is acetone;
said first substrate is acetoin and said second substrate is MEK;
said first substrate is acetoin and said second substrate is acetaldehyde;
said first substrate is acetaldehyde and said second substrate is acetone;
said first substrate is acetaldehyde and said second substrate is acetoin; or
said first substrate is acetaldehyde and said second substrate is MEK.

8. The microorganism of claim 5, wherein said alcohol dehydrogenase uses NADH as a co-factor or has increased specificity for an NADH co-factor over an NADH co-factor.

9. The microorganism of claim 5, wherein said microorganism is selected from the group consisting of *Acetobacterium woodii, Clostridium* acetobutylicum, *Clostridium* autoethanogenum, *Clostridium* ljungdahlii, *Clostridium ragsdalei, Escherichia coli, Moorella thermoacetica*, and *Saccharomyces cerevisiae*.

10. The microorganism of claim 9, wherein said microorganism is *Clostridium* autoethanogenum.

11. The microorganism of claim 5, wherein said microorganism produces a product selected from the group consisting of isopropanol, ethanol, 2,3-butanediol, 2-butanol, acetoin, MEK, acetaldehyde, and acetone.

12. A method of producing a product comprising culturing a microorganism comprising the alcohol dehydrogenase of claim 1, wherein said microorganism produces said product.

13. The method of claim 12, wherein said alcohol dehydrogenase comprises:
a Ser199Asp amino acid substitution;
a Ser199Glu amino acid substitution;
a combination of said amino acid substitutions Gly198Asp, Ser199Val, and Pro201Glu;
a combination of said amino acid substitutions Gly198Asp, Ser199Val, Pro201Glu, and Tyr218Ala;
a combination of said amino acid substitutions Gly198Asp, Ser199Val, Pro201Glu, and Tyr218Phe;
a combination of said amino acid substitutions Gly198Asp, Ser199Val, Pro201Glu, and Tyr218Val;
a combination of said amino acid substitutions Gly198Asp, Ser199Val, Pro201Glu, and Tyr218Gy; or
a combination of said amino acid substitutions Gly198Asp, Ser199Val, Pro201Glu, and Tyr218Ser.

14. The method of claim 12, wherein said alcohol dehydrogenase has increased specificity for at least one first substrate over at least one second substrate wherein:
said first substrate is acetone and said second substrate is methyl ethyl ketone (MEK);
said first substrate is acetone and said second substrate is acetaldehyde;
said first substrate is acetone and said second substrate is acetoin;
said first substrate is MEK and said second substrate is acetaldehyde;
said first substrate is MEK and said second substrate is acetoin;
said first substrate is acetoin and said second substrate is acetone;
said first substrate is acetoin and said second substrate is MEK;
said first substrate is acetoin and said second substrate is acetaldehyde;
said first substrate is acetaldehyde and said second substrate is acetone;
said first substrate is acetaldehyde and said second substrate is acetoin; or
said first substrate is acetaldehyde and said second substrate is MEK.

15. The method of claim 12, wherein said alcohol dehydrogenase uses NADH as a co-factor or has increased specificity for an NADH co-factor over an NADH co-factor.

16. The method of claim 12, wherein said microorganism is selected from the group consisting of *Acetobacterium woodii, Clostridium* acetobutylicum, *Clostridium* autoethanogenum, *Clostridium* ljungdahlii, *Clostridium ragsdalei, Escherichia coli, Moorella thermoacetica*, and *Saccharomyces cerevisiae*.

17. The microorganism of claim 12, wherein said microorganism is *Clostridium* autoethanogenum.

18. The method of claim 12, wherein said product is selected from the group consisting of isopropanol, ethanol, 2,3-butanediol, 2-butanol, acetoin, MEK, acetaldehyde, and acetone.

19. The alcohol dehydrogenase of claim 1, wherein said alcohol dehydrogenase further comprises at least one amino acid substitution selected from the group consisting of Gly198Asp and Tyr218Phe.

20. The microorganism of claim 5, wherein said alcohol dehydrogenase further comprises at least one amino acid substitution selected from the group consisting of Gly198Asp and Tyr218Phe.

21. The method of claim 12, wherein said alcohol dehydrogenase further comprises at least one amino acid substitution selected from the group consisting of Gly198Asp and Tyr218Phe.

* * * * *